US007919246B2

(12) United States Patent
Lai et al.

(10) Patent No.: US 7,919,246 B2
(45) Date of Patent: Apr. 5, 2011

(54) SEMA4D IN CANCER DIAGNOSIS, DETECTION AND TREATMENT

(75) Inventors: Albert Lai, Davis, CA (US); Abdallah Fanidi, Fair Oaks, CA (US); Robert Booher, Davis, CA (US); Christin Tse, Libertyville, IL (US); Xie Xu, Carlsbad, CA (US); Guoying Yu, Kensington, CA (US); Edward Moler, Walnut Creek, CA (US); Michael Rowe, Oakland, CA (US)

(73) Assignees: Novartis Vaccines and Diagnostics, Inc., Emeryville, CA (US); Sagres Discovery, Inc., Emeryville, CA (US)

( * ) Notice: Subject to any disclaimer, the term of this patent is extended or adjusted under 35 U.S.C. 154(b) by 0 days.

(21) Appl. No.: 11/918,179

(22) PCT Filed: Apr. 7, 2006

(86) PCT No.: PCT/US2006/013174
§ 371 (c)(1),
(2), (4) Date: Nov. 19, 2008

(87) PCT Pub. No.: WO2006/110594
PCT Pub. Date: Oct. 19, 2006

(65) Prior Publication Data
US 2009/0104193 A1 Apr. 23, 2009

Related U.S. Application Data

(60) Provisional application No. 60/669,855, filed on Apr. 7, 2005.

(51) Int. Cl.
*C12Q 1/68* (2006.01)
*G01N 33/53* (2006.01)
(52) U.S. Cl. .......................................... 435/6; 435/7.1
(58) Field of Classification Search .................. None
See application file for complete search history.

(56) References Cited

U.S. PATENT DOCUMENTS
7,171,311 B2 * 1/2007 Dai et al. ...................... 702/19

FOREIGN PATENT DOCUMENTS
WO 97/17368 5/1997
WO 03/057146 7/2003
WO 2005/031001 4/2005

OTHER PUBLICATIONS

Hall et al (PNAS, Oct. 1996, 93: 11780-11785) teaches.*
Tockman et al (Cancer Res., 1992, 52:2711s-2718s).*
Alberts et al. (Molecular Biology of the Cell, 3rd edition, 1994, p. 465).*
Greenbaum et al. (Genome Biology, 2003, vol. 4, Issue 9, pp. 117.1-117.8).*
Dorfman et al (American Journal of Pathology, Jul. 1998, 153(1): 255-262).*

Basile et al., "Class IV semaphorins promote anglogenesls by stimulating Rho-initiated pathways through piexin-B." *Cancer Res* 64(15):5212-5224 (2004).
Basile et al., "Semaphorin 4D provides a link between axon guidance processes and tumor-induced angiogenesis." *Proc. Natl. Acad. Sci. U.S.A.* 103(24):9017-9022 (2006).
Conrotto et al., "Interplay between scatter factor receptors and B plexins controls invasive growth." *Oncogene* 23(30):5131-5137 (2004).
Deaglio et al., "CD38 and CD100 lead a network of surface receptors relaying positive signals for B-CLL growth and survival." *Blood* 105(8): 3042-3050 (2005).
Dorfman et al., "The leukocyte semaphorin CD100 is expressed in most T-cell, but few B-cell, non-Hodgkin's lymphomas." *Am. J. Pathol* 153(1):255-262 (1998).
Elhabazi et al., "Biological activity of soluble CD100. I. The extracellular region of CD100 is released from the furface of T lymphocytes by regulated proteopysis." *J. Immunol* 166(7):4341-4347 (2001).
Glordano et al., "The semaphorin 4D receptor controls invasive growth by coupling with Met." *Nat. Cell. Biol.* 4(9):720-724 (2002).
Granziero et al., "CD100/Plexin-B1 interactions sustain proliferation and survival of normal and leukemic CD5+ B lymphocytes." *Blood* 101(5):1962-1969 (2003).
Hansen et al., "Genetic profile of insertion mutations in mouse leukemias and lymphomas." *Genome Res.* 10(2):237-243 (2000).
Herold et al., "Activation signals are delivered through two distinct epitopes of CD100, a unique 150 kDa human lymphocyte surface structure previously defined by BB18 mAb." *Int. Immunol.* 7(1):1-8 (1995).
Joosten et al., "Phenotyping of Evi1. Evi11/Cb2, and Evi12 transformed leukemias isolated from a novel panel of cas-Br-M murine leukemia virus-infected mice." *Virology* 268(2):308-318 (2000).
Kim et al., "Genome-based identification of cancer genes by proviral tagging in mouse retrovirus-induced T-cell lymphomas." *J. Virol.* 77(3):2056-2062 (2003).
Kumanogoh et al., "Identification of CD72 as a lymphocyte receptor for the class IV semaphorin CD100: a novel mechanism for regulating B cell signaling." *Immunity* 13(5):621-631 (2000).
Li et al., "Leukaermia disease genes: large-scale cloning and pathway predictions," *Nat. Genet.* 23(3):348-353 (1999).
Mikkers and Berns, "Retroviral Insertional mutagenesis: lagging cancer pathways." *Adv. Cancer Res* 88:53-99 (2003).
Sørensen et al., "Amplification and sequence analysis of DNA flanking integrated proviruses by a simple two-step polymerase chain reaction method." *J. Virol.* 67(12):7118-7124 (1993).
Sørensen et al., "Sequence tags of provirus integration sites in DNAs of tumors induced by the murine retrovirus SL3-3." *J. Virol.* 70(6):4063-4070 (1996).
Sørensen et al., "Sint1, a common integration site in SL3-3-induced T-cell lymphomas, harbors a putative proto-oncogene with homology to the septin gene family." *J. Virol.* 74(5):2161-2166 (2000).

(Continued)

*Primary Examiner* — Sean E Aeder
(74) *Attorney, Agent, or Firm* — David A. Carpenter

(57) ABSTRACT

This invention is in the field of cancer-related genes. Specifically it relates to methods for detecting cancer or the likelihood of developing cancer based on the presence or absence of the SEM A4D gene or proteins encoded by this gene. The invention also provides methods and molecules for upregulating or downregulating the SEMA4D gene.

4 Claims, 7 Drawing Sheets

OTHER PUBLICATIONS

Vikis et al., "The semaphorin receptor plexin-B1 specifically interacts with active Rac in a ligand-dependent manner." *Proc. Natl. Acad. Sci.* U.S.A. 97(23):12457-12462 (2000).
Yamada et al., "Identification of semaphorin E as a non-MDR drug resistance gene of human cancers." *Proc. Natl. Acad. Sci.* U.S.A. 26(94):14713-14718 (1997).
Accession No. AAC50810, Nov. 29, 2010.
Accession No. AAH54500, Nov. 29, 2010.
Accession No. BCO54500, Nov. 29, 2010.
Accession No. BX648216, Nov. 29, 2010.
Accession No. NM_006378, Nov. 29, 2010.
Accession No. NP_006369, Nov. 29, 2010.
Accession No. Q92854, Nov. 29, 2010.
Accession No. U60800, Nov. 29, 2010.

* cited by examiner

| Species | Tissue | Normal # | Tumor # |
|---|---|---|---|
| Human | Bladder | 3 | 4 |
| Human | Breast | 6 | 8 |
| Non-human Primate | Brain | 2 | n/a |
| Human | Colon | 4 | 4 |
| Non-human Primate | Heart | 2 | n/a |
| Human | Kidney | 4 | 4 |
| Human | Liver | 1 | 1 |
| Human | Lung | 4 | 3 |
| Human | Lymphoid | 1 | 5 |
| Human | Ovary | 1 | 8 |
| Human | Pancreas | 3 | 7 |
| Human | Prostate | 3 | 3 |
| Human | Skin | 4 | 4 |

FIG. 3

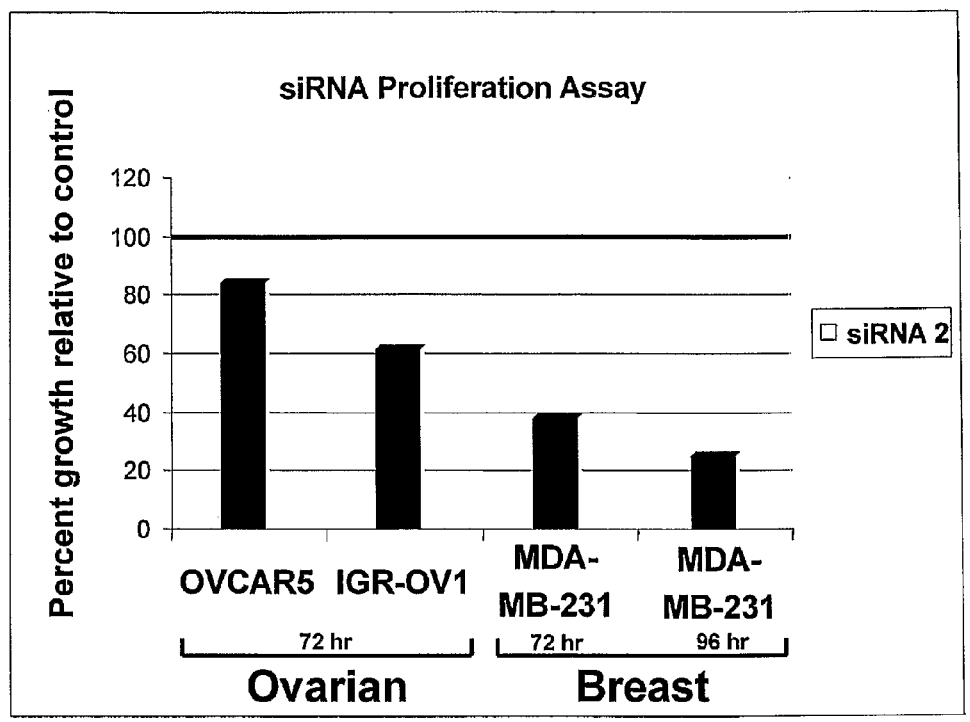
FIG. 4A
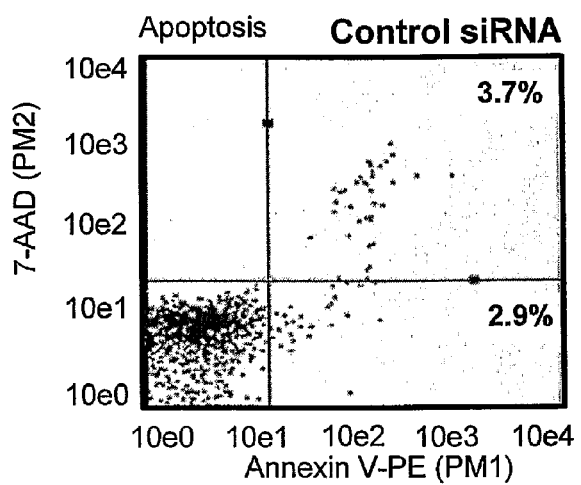
FIG. 4B
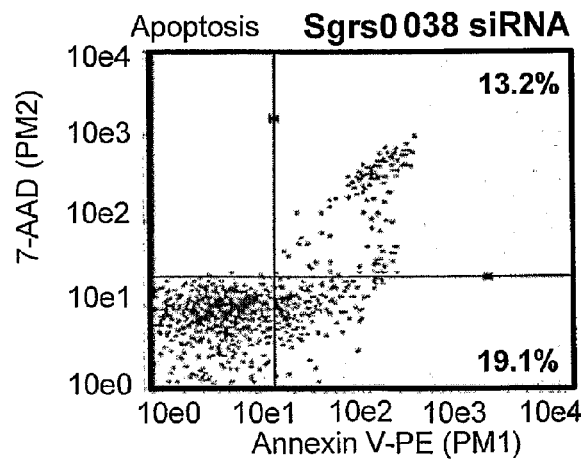

SEMA4D IN CANCER DIAGNOSIS, DETECTION AND TREATMENT

CROSS REFERENCE TO RELATED APPLICATIONS

The present application claims priority of U.S. Ser. No. 60/669,855, filed Apr. 7, 2005, which is hereby incorporated by reference in its entirety.

FIELD OF THE INVENTION

This invention is in the field of cancer-associated genes. Specifically it relates to methods for detecting cancer or the likelihood of developing cancer based on the presence of differential expression of SEMA4D or SEMA4D gene products. The invention also provides methods and molecules for detecting, diagnosing and treating cancer by modulating SEMA4D or SEMA4D gene products.

BACKGROUND OF THE INVENTION

Oncogenes are genes that can cause cancer. Carcinogenesis can occur by a wide variety of mechanisms, including infection of cells by viruses containing oncogenes, activation of protooncogenes (normal genes that have the potential to become an oncogene) in the host genome, and mutations of protooncogenes and tumour suppressor genes. Carcinogenesis is fundamentally driven by somatic cell evolution (i.e. mutation and natural selection of variants with progressive loss of growth control). The genes that serve as targets for these somatic mutations are classified as either protooncogenes or tumour suppressor genes, depending on whether their mutant phenotypes are dominant or recessive, respectively.

There are a number of viruses known to be involved in human as well as animal cancer. Of particular interest here are viruses that do not contain oncogenes themselves; these are slow-transforming retroviruses. Such viruses induce tumours by integrating into the host genome and affecting neighboring protooncogenes in a variety of ways. Provirus insertion mutation is a normal consequence of the retroviral life cycle. In infected cells, a DNA copy of the retrovirus genome (called a provirus) is integrated into the host genome. A newly integrated provirus can affect gene expression in cis at or near the integration site by one of two mechanisms. Type I insertion mutations up-regulate transcription of proximal genes as a consequence of regulatory sequences (enhancers and/or promoters) within the proviral long terminal repeats (LTRs). Type II insertion mutations located within the intron or exon of a gene can up-regulate transcription of said gene as a consequence of regulatory sequences (enhancers and/or promoters) within the proviral long terminal repeats (LTRs). Additionally, type II insertion mutations can cause truncation of coding regions due to either integration directly within an open reading frame or integration within an intron flanked on both sides by coding sequences, which could lead to a truncated or an unstable transcript/protein product. The analysis of sequences at or near the insertion sites has led to the identification of a number of new protooncogenes.

With respect to lymphoma and leukemia, retroviruses such as AKV murine leukemia virus (MLV) or SL3-3 MLV, are potent inducers of tumours when inoculated into susceptible newborn mice, or when carried in the germline. A number of sequences have been identified as relevant in the induction of lymphoma and leukemia by analyzing the insertion sites; see Sorensen et al., J. Virology 74:2161 (2000); Hansen et al., Genome Res. 10(2):237-43 (2000); Sorensen et al., J. Virology 70:4063 (1996); Sorensen et al., J. Virology 67:7118 (1993); Joosten et al., Virology 268:308 (2000); and Li et al., Nature Genetics 23:348 (1999); all of which are expressly incorporated by reference herein. With respect to cancers, especially breast cancer, prostate cancer and cancers with epithelial origin, the mammalian retrovirus, mouse mammary tumour virus (MMTV) is a potent inducer of tumours when inoculated into susceptible newborn mice, or when carried in the germ line. *Mammary Tumours in the Mouse*, edited by J. Hilgers and M. Sluyser; Elsevier/North-Holland Biomedical Press; New York, N.Y.

The pattern of gene expression in a particular living cell is characteristic of its current state. Nearly all differences in the state or type of a cell are reflected in the differences in RNA levels of one or more genes. Comparing expression patterns of uncharacterized genes may provide clues to their function. High throughput analysis of expression of hundreds or thousands of genes can help in (a) identification of complex genetic diseases, (b) analysis of differential gene expression over time, between tissues and disease states, and (c) drug discovery and toxicology studies. Increase or decrease in the levels of expression of certain genes correlate with cancer biology. For example, oncogenes are positive regulators of tumorigenesis, while tumour suppressor genes are negative regulators of tumorigenesis. (Marshall, Cell, 64: 313-326 (1991); Weinberg, Science, 254: 1138-1146 (1991)).

Immunotherapy, or the use of antibodies for therapeutic purposes has been used in recent years to treat cancer. Passive immunotherapy involves the use of monoclonal antibodies in cancer treatments. See for example, Cancer: Principles and Practice of Oncology, 6th Edition (2001) Chapt. 20 pp. 495-508. Inherent therapeutic biological activity of these antibodies include direct inhibition of tumour cell growth or survival, and the ability to recruit the natural cell killing activity of the body's immune system. These agents are administered alone or in conjunction with radiation or chemotherapeutic agents. Rituxan® and Herceptin®, approved for treatment of lymphoma and breast cancer, respectively, are two examples of such therapeutics. Alternatively, antibodies are used to make antibody conjugates where the antibody is linked to a toxic agent and directs that agent to the tumour by specifically binding to the tumour. Mylotarg® is an example of an approved antibody conjugate used for the treatment of leukemia. However, these antibodies target the tumour itself rather than the cause.

An additional approach for anti-cancer therapy is to target the protooncogenes that can cause cancer. Genes identified as causing cancer can be monitored to detect the onset of cancer and can then be targeted to treat cancer.

SEMA4D is a 150 kDa surface antigen that belongs to the semaphorin family (Herold C. et al., (1995) Int Immunol; 7(1):1-8). The membrane bound form of SEMA4D has an N-terminal signal sequence followed by a Sema domain, an Ig-like domain, a lysine rich region, a hydrophobic transmembrane domain and a cytoplasmic tail (Hall K T et al., (1998) PNAS, 93(21):11780-5). The extracellular domain conatind putative N-linked glycosylation sites. The cytoplasmic domain contains a site for tyrosine phosphorylation and multiple sites for serine phosphorylation. SEMA4D forms homodimers, C647 in the Sema domain is required for dimerisation. Shedding of the extracellular domain is metalloprotease dependent, and is regulated by phosphorylation (Elhabazi A. (2001) J Immunol; 166(7):4341-70). Receptors for SEMA4D include Plexin-B1 (Vikis H G (2000) PNAS 97(23):12457-62 and CD72 (Kumanogoh A (2000) Immunity, 13(5):621-31).

Members of the semaphorin family are involved in axonal guidance, and SEMA4D is thought to have a role in the regulation of the humoral and cellular immune response. SEMA4D knock-out mice show defects in the immune system. It has been suggested that, given its role in of the immune response, SEMA4D could be used to stimulate T-cells and B-cells in cancer patients (JP2001048803 and WO 97/17368). SEMA4D is also involved in angiogenesis (Basile J R (2004) Cancer Res; 64(15):5212-24), and may have a role in invasive cell growth (Conrotto P et al., (2004) Oncogene; 23(30):5131-7 and Giordano S. et al., (2002) Nat Cell Biol; 4(9):720-4). SEMA4D has also been implicated in T-cell, but not B-cell, non-Hodgkin's lymphoma (Dorfman D M et al., (1998) Am J Pathol; 153(1):255-62).

SUMMARY OF THE INVENTION

In some aspects, the present invention provides methods for treating cancer in a patient comprising modulating the level of an expression product of SEMA4D. In some embodiments the cancer is lymphoma, melanoma, breast cancer, colon cancer, kidney cancer, liver cancer, lung cancer, ovary cancer, pancreatic cancer, prostate cancer, uterine cancer, cervical cancer, bladder cancer, stomach cancer or skin cancer.

In some aspects, the present invention provides methods of treating a cancer in a patient characterized by overexpression of SEMA4D relative to a control. In some embodiments the method comprises modulating SEMA4D gene expression in the patient.

In some aspects, the present invention provides methods treating cancer in a patient comprising modulating an SEMA4D-activity. In some embodiments the SEMA4D activity is selected from the group consisting of cell proliferation, cell growth, cell motility, metastasis, cell migration, cell survival, and tumorigenicity.

In some aspects, the present invention provides methods for diagnosing cancer comprising detecting evidence of differential expression in a patient sample of SEMA4D. In some embodiments evidence of differential expression of SEMA4D is diagnostic of cancer.

In some aspects, the present invention provides methods for detecting a cancerous cell in a patient sample comprising detecting evidence of an expression product of SEMA4D. In some embodiments evidence of expression of SEMA4D in the sample indicates that a cell in the sample is cancerous.

In some aspects, the present invention provides methods for assessing the progression of cancer in a patient comprising comparing the level of an expression product of SEMA4D in a biological sample at a first time point to a level of the same expression product at a second time point. In some embodiments a change in the level of the expression product at the second time point relative to the first time point is indicative of the progression of the cancer.

In some aspects, the present invention provides methods of diagnosing cancer comprising:
(a) measuring a level of mRNA of SEMA4D in a first sample, said first sample comprising a first tissue type of a first individual; and
(b) comparing the level of mRNA in (a) to:
(1) a level of the mRNA in a second sample, said second sample comprising a normal tissue type of said first individual, or
(2) a level of the mRNA in a third sample, said third sample comprising a normal tissue type from an unaffected individual. In some embodiments at least a two fold difference between the level of mRNA in (a) and the level of the mRNA in the second sample or the third sample indicates that the first individual has or is predisposed to cancer.

In some aspects, the present invention provides of screening for anti-cancer activity comprising:
(a) contacting a cell that expresses SEMA4D with a candidate anti-cancer agent; and
(b) detecting at least a two fold difference between the level of SEMA4D expression in the cell in the presence and in the absence of the candidate anti-cancer agent. In some embodiments at least a two fold difference between the level of SEMA4D expression in the cell in the presence and in the absence of the candidate anti-cancer agent indicates that the candidate anti-cancer agent has anti-cancer activity.

In some aspects, the present invention provides methods for identifying a patient as susceptible to treatment with an antibody that binds to an expression product of SEMA4D comprising measuring the level of the expression product of the gene in a biological sample from that patient.

In some aspects, the present invention provides kit for the diagnosis or detection of cancer in a mammal. In some embodiments the kit comprises an antibody or fragment thereof, or an immunoconjugate or fragment thereof, according to any one of the proceeding embodiments. In some embodiments the antibody or fragment specifically binds an SEMA4D tumor cell antigen; one or more reagents for detecting a binding reaction between said antibody and said SEMA4D tumor cell antigen. In some embodiments the kits comprise instructions for using the kit.

In some aspects, the present invention provides kits for diagnosing cancer comprising a nucleic acid probe that hybridises under stringent conditions to an SEMA4D gene; primers for amplifying the SEMA4D gene. In some embodiments the kits comprise instructions for using the kit.

In some aspects, the present invention provides compositions comprising one or more antibodies or oligonucleotides specific for an expression product of SEMA4D.

These and other aspects of the present invention will be elucidated in the following detailed description of the invention.

BRIEF DESCRIPTION OF THE FIGURES

FIG. 3 depicts the distribution of SEMA4D in cancerous and non-cancerous tissues, detected by IHC with an anti-SEMA4D antibody.

FIGS. 4A and 4B depict the effect of silencing SEMA4D expression using RNAi.

DETAILED DESCRIPTION

Figure 1:
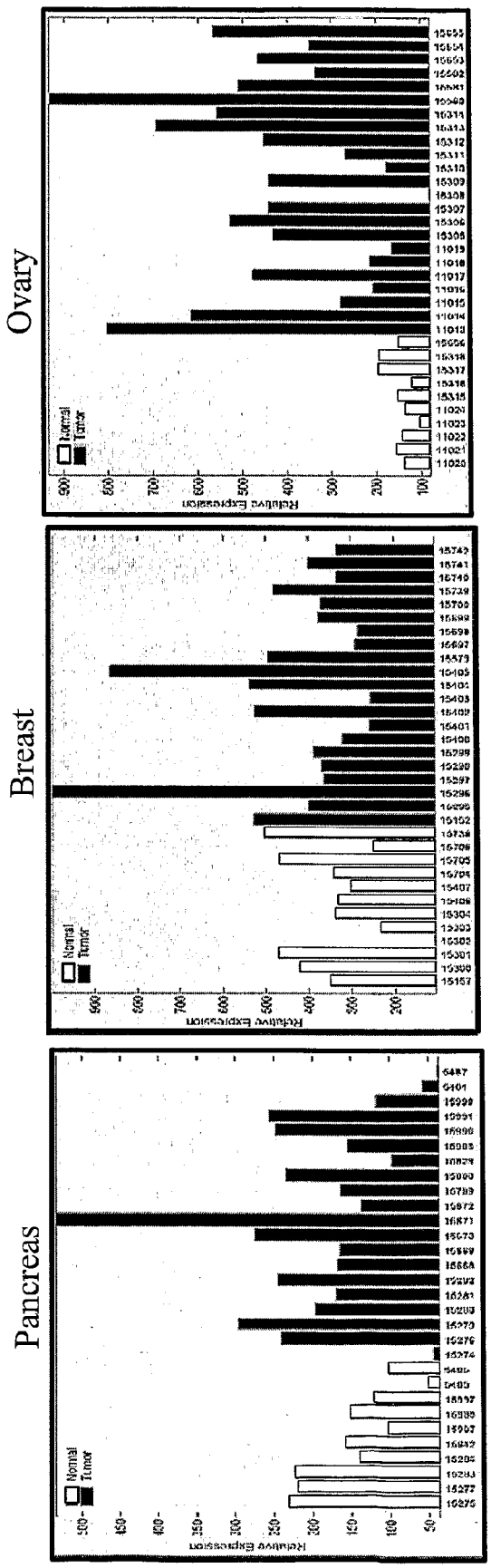
FIG. 1 depicts results for Q-PCR experiments and demonstrates SEMA4D disregulation in breast, liver, lung, lymphoid, ovary, pancreas, prostate, skin and uterine cancer tissue.
Figure 2:
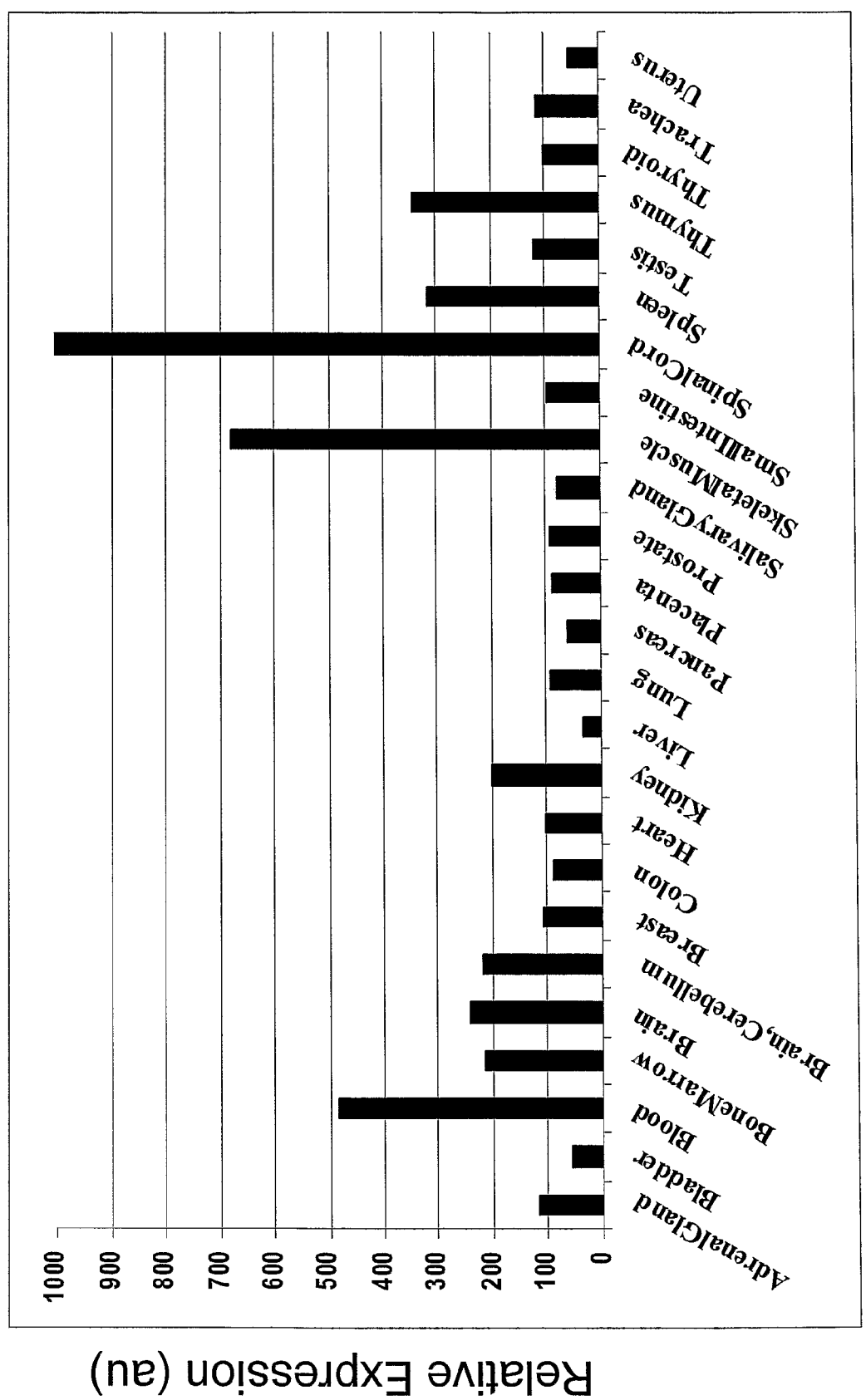
FIG. 2 depicts Gene Expression Profiling in Normal Tissues

The present invention provides methods and compositions for the treatment, diagnosis and imaging of cancer, in particular for the treatment, diagnosis and imaging of SEMA4D-related cancer.

Protooncogenes have been identified in humans using a process known as "provirus tagging", in which slow-transforming retroviruses that act by an insertion mutation mechanism are used to isolate protooncogenes using mouse models. In some models, uninfected animals have low cancer rates, and infected animals have high cancer rates. It is known that many of the retroviruses involved do not carry transduced host protooncogenes or pathogenic trans-acting viral genes, and thus the cancer incidence must therefore be a direct consequence of proviral integration effects into host protooncogenes. Since proviral integration is random, rare integrants will "activate" host protooncogenes that provide a selective growth advantage, and these rare events result in new proviruses at clonal stoichiometries in tumors. In contrast to mutations caused by chemicals, radiation, or spontaneous errors, protooncogene insertion mutations can be easily located by virtue of the fact that a convenient-sized genetic marker of known sequence (the provirus) is present at the site of mutation. Host sequences that flank clonally integrated proviruses can be cloned using a variety of strategies. Once these sequences are in hand, the tagged protooncogenes can be subsequently identified. The presence of provirus at the same locus in two or more independent tumors is prima facie evidence that a protooncogene is present at or very near the provirus integration sites (Kim et al, Journal of Virology, 2003, 77:2056-2062; Mikkers, H and Berns, A, Advances in Cancer Research, 2003, 88:53-99; Keoko et al. Nucleic Acids Research, 2004, 32:D523-D527). This is because the genome is too large for random integrations to result in observable clustering. Any clustering that is detected is unequivocal evidence for biological selection (i.e. the tumor phenotype). Moreover, the pattern of proviral integrants (including orientations) provides compelling positional information that makes localization of the target gene at each cluster relatively simple. The three mammalian retroviruses that are known to cause cancer by an insertion mutation mechanism are FeLV (leukemia/lymphoma in cats), MLV (leukemia/lymphoma in mice and rats), and MMTV (mammary cancer in mice). Once protooncogenes have been identified in mouse models, the human orthologs can be annotated as protooncogenes and further investigations carried out.

Thus, the use of oncogenic retroviruses, whose sequences insert into the genome of the host organism resulting in cancer, allows the identification of host genes involved in cancer. These sequences may then be used in a number of different ways, including diagnosis, prognosis, screening for modulators (including both agonists and antagonists), antibody generation (for immunotherapy and imaging), etc. However, as will be appreciated by those in the art, oncogenes that are identified in one type of cancer such as those identified in the present invention, have a strong likelihood of being involved in other types of cancers as well.

The SEMA4D gene has been identified as being a cell membrane associated target for the treatment and diagnosis of breast cancer (adenocarcinoma of breast: lobular and ductal), colon cancer, ovarian cancer (adenocarcinoma of ovary: serous, papillary serous, endometrioid, and clear cell), pancreatic cancer (adenocarcinoma of pancreas, ductal), prostate cancer, lymphoid cancers (acute T cell leukemia, acute lymphoblastic leukaemia, non-Hodgkin's lymphoma, anaplastic lymphoma, large cell lymphoma), and kidney cancer (renal cell adenocarcinoma). The carcinoma cell types correspond to those patient tumor samples that showed overexpression by QPCR analysis. This means that this gene is correlated with breast, colon, lymphoid, ovary, pancreas, prostate, and kidney cancer and is therefore a target for the diagnosis and therapy of these and other cancers.

The invention therefore provides methods for detecting cancerous cells in a biological sample comprising investigating the sequence or expression level of the SEMA4D gene.

The SEMA4D gene underwent type I and II integrations of the MMTV and MLV proviruses and integration was found in 8 cases. This gene was found to be overexpressed at the mRNA level using patients' tumour samples in 33% of breast cancer tissue sampled, 87% of ovarian cancer tissue sampled, 40% of pancreatic cancer tissue sampled. This gene was also found to be overexpressed in colon and prostate tumors sampled (t-test). This means that this gene is correlated with breast, pancreas, ovarian, colon and prostate cancer and is therefore a promising target for the diagnosis and therapy of these diseases.

As used herein, the term "cancer-associated gene" refers to the SEMA4D gene.

These genes have been identified and validated as protooncogenes using the methods described herein.

In some embodiments the methods include measuring the level of expression of one or more (i.e. 1, 2, 3, 4, 5, 6, 7, 8, 9, 10 or more) expression products of the cancer-associated gene, wherein a level of expression that is different to a control level is indicative of disease.

In some embodiments the expression product is a protein, although alternatively mRNA expression products may be detected. If a protein is used, the protein is preferably detected by an antibody which preferably binds specifically to that protein. The term "binds specifically" means that the antibodies have substantially greater affinity for their target polypeptide than their affinity for other related polypeptides. As used herein, the term "antibody" refers to intact molecules as well as to fragments thereof, such as Fab, F(ab')2 and Fv, which are capable of binding to the antigenic determinant in question. By "substantially greater affinity" we mean that there is a measurable increase in the affinity for the target polypeptide of the invention as compared with the affinity for other related polypeptide. In some embodiments, the affinity is at least 1.5-fold, 2-fold, 5-fold 10-fold, 100-fold, $10^3$-fold, $10^4$-fold, $10^5$-fold, $10^6$-fold or greater for the target polypeptide.

In some embodiments, the antibodies bind with high affinity, with a dissociation constant of $10^{-4}$M or less, $10^{-7}$M or less, $10^{-9}$M or less; or subnanomolar affinity (0.9, 0.8, 0.7, 0.6, 0.5, 0.4, 0.3, 0.2, 0.1 nM or even less).

Where mRNA expression product is used, in some embodiments it is detected by contacting a tissue sample with a probe under conditions that allow the formation of a hybrid complex between the mRNA and the probe; and detecting the formation of a complex. In some embodiments stringent hybridization conditions are used.

Cancer associated genes themselves may be detected by contacting a biological sample with a probe under conditions that allow the formation of a hybrid complex between a nucleic acid expression product encoding SEMA4D and the probe; and detecting the formation of a complex between the probe and the nucleic acid from the biological sample. In some embodiments, the absence of the formation of a complex is indicative of a mutation in the sequence of the cancer-associated gene.

Methods include comparing the amount of complex formed with that formed when a control tissue is used, wherein a difference in the amount of complex formed between the control and the sample indicates the presence of cancer. In some embodiments the difference between the amount of complex formed by the test tissue compared to the normal tissue is an increase or decrease. In some embodiments a two-fold increase or decrease in the amount of complex formed is indicative of disease. In some embodiments, a 3-fold, 4-fold, 5-fold, 10-fold, 20-fold, 50-fold or even 100-fold increase or decrease in the amount of complex formed is indicative of disease.

In some embodiments the biological sample used in the methods of the invention is a tissue sample. Any tissue sample may be used. In some embodiments, however, the tissue is selected from breast tissue, lung tissue, liver tissue, lymphoid tissue, ovary tissue, pancreas tissue, prostate tissue, uterine tissue or skin tissue.

The invention also provides methods for assessing the progression of cancer in a patient comprising comparing the expression of SEMA4D in a biological sample at a first time point to the expression of the same expression product at a second time point, wherein an increase or decrease in expression, or in the rate of increase or decrease of expression, at the second time point relative to the first time point is indicative of the progression of the cancer.

The invention also provides kits useful for diagnosing cancer comprising an antibody that binds to a polypeptide expression product of SEMA4D; and a reagent useful for the detection of a binding reaction between said antibody and said polypeptide. In some embodiments, the antibody binds specifically to the polypeptide product of SEMA4D.

Furthermore, the invention provides a kit for diagnosing cancer comprising a nucleic acid probe that hybridises under stringent conditions to a cancer-associated gene; primers useful for amplifying the cancer-associated gene; and, optionally, instructions for using the probe and primers for facilitating the diagnosis of disease.

The invention further provides antibodies, nucleic acids, or proteins suitable for use in modulating the expression of an expression product of SEMA4D for use in treating cancer.

Accordingly, the invention provides methods for treating cancer in a patient, comprising modulating the level of one or more (i.e. 1, 2, 3, 4, 5, 6, 7, 8, 9, 10 or more) expression products of SEMA4D. In some embodiments the methods comprise administering to the patient a therapeutically-effective amount of an antibody, a nucleic acid, or a polypeptide that modulates the level of said expression product.

The invention therefore also provides the use of an antibody, a nucleic acid, or a polypeptide that modulates the level of an expression product of SEMA4D, in the manufacture of a medicament for the treatment, detection or diagnosis of cancer. In some embodiments the level of expression is modulated by action on the gene, mRNA or the encoded protein. In some embodiments the expression is upregulated or downregulated. For example, the change in regulation may be 2-fold, 3-fold, 5-fold, 10-fold, 20-fold, 50-fold, or even 100 fold or more.

Antibodies suitable for use in accordance with the present invention may be specific for cancer-associated proteins as these are expressed on or within cancerous cells. For example, glycosylation patterns in cancer-associated proteins as expressed on cancerous cells may be different to the patterns of glycosylation in these same proteins as these are expressed on non-cancerous cells. In some embodiments antibodies according to the invention are specific for cancer-associated proteins as expressed on cancerous cells only. This is of particular value for therapeutic antibodies. Anti-target antibodies may also bind to splice variants, deletion, addition and/or substitution mutants of the target.

Antibodies suitable for therapeutic use in accordance with the present invention elicit antibody-dependent cellular cytotoxicity (ADCC). ADCC refers to the cell-mediated reaction wherein non-specific cytotoxic cells that express Fc receptors recognize bound antibody on a target cell and subsequently cause lysis of the target cell (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). Antibodies suitable for therapeutic use in accordance with the present invention may elicit antibody-dependent cell-mediated phagocytosis (ADCP). ADCP is the cell-mediated reaction wherein nonspecific cytotoxic cells that express Fc receptors recognize bound antibody on a target cell and subsequently cause phagocytosis. These processes are mediated by natural killer (NK) cells, which possess receptors on their surface for the Fc portion of IgG antibodies. When IgG is made against epitopes on "foreign" membrane-bound cells, including cancer cells, the Fab portions of the antibodies react with the cancerous cell. The NK cells then bind to the Fc portion of the antibody.

In embodiments where it is desirable to modify the antibody of the invention with respect to effector function, e.g. so as to enhance antigen-dependent cell-mediated cyotoxicity (ADCC) and/or complement dependent cytotoxicity (CDC) of the antibody, one or more amino acid substitutions can be introduced into an Fc region of the antibody. Alternatively or additionally, cysteine residue(s) may be introduced in the Fc region, thereby allowing interchain disulfide bond formation in this region (For review: Weiner and Carter (2005) Nature Biotechnology 23(5): 556-557). The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989). Antibodies can be produced with modified glycosylation within the Fc region. For example, lowering the fucose content in the carbohydrate chains may improve the antibody's intrinsic ADCC activity (see for example BioWa's Potillegent™ ADCC Enhancing Technology, described in WO0061739). Alternately, antibodies can be produced in cell lines that add bisected non-fucosylated oligosaccharide chains (see U.S. Pat. No. 6,602,684). Both these technologies produce antibodies with an increased affinity for the FcgammaIIIa receptor on effector cells which results in increased ADCC efficiency. The Fc region can also be engineered to alter the serum half life of the antibodies of the invention. Abdegs are engineered IgGs with an increased affinity for the FcRn salvage receptor, and so have shorter half life than conventional IgGs (see Vaccaro et al, (2005) Nature Biotechnology 23(10): 1283-1288). To increase serum half life, specific mutations can be introduced into the Fc region that appear to decrease the affinity with FcRn (see Hinton et al, (2004) J Biol Chem 297(8): 6213-6216). Antibodies of the invention can also be modified to use other mechanisms to alter serum half life, such as including a serum albumin binding domain (dAb) (see WO05035572 for example). Engineered Fc domains (see for example XMAB™, WO05077981) may also be incorporated into the antibodies of the invention to lead to improved ADCC activity, altered serum half life or increased antibody protein stability.

In some embodiments, antibodies for therapeutic use in accordance with the invention are effective to elicit ADCC, and modulates the survival of cancerous cells by binding to target and having ADCC activity. Antibodies can be engineered to heighten ADCC activity (see, for example, US 20050054832A1, Xencor Inc. and the documents cited therein).

In some embodiments the nucleic acid type used in such methods is an antisense construct, a ribozyme or RNAi, including, for example, siRNA.

The cancer may be treated by the inhibition of tumour growth or the reduction of tumour volume or, alternatively, by reducing the invasiveness of a cancer cell. In some embodiments, the methods of treatment described above are used in conjunction with one or more of surgery, hormone ablation therapy, radiotherapy or chemotherapy. For example, if a patient is already receiving chemotherapy, a compound of the invention that modulates the level of an expression product as listed above may also be administered. The chemotherapeutic, hormonal and/or radiotherapeutic agent and compound according to the invention may be administered simultaneously, separately or sequentially.

In some embodiments the cancer being detected or treated according to one of the methods described above is selected from breast cancer, colon cancer, kidney cancer, liver cancer, lung cancer, lymphoid cancer, ovary cancer, pancreas cancer, prostate cancer, uterine cancer, cervix cancer or skin cancer.

The invention provides methods for diagnosing cancer comprising detecting evidence of differential expression in a patient sample of SEMA4D. Evidence of differential expression of the gene is diagnostic of cancer. In some embodiments, evidence of differential expression of the gene is detected by measuring the level of an expression product of the gene. In some embodiments the expression product is a protein or mRNA. In some embodiments the level of expression of protein is measured using an antibody which binds specifically to the protein. In some embodiments the antibody is linked to an imaging agent. In some embodiments the level of expression product of the gene in the patient sample is compared to a control. In some embodiments the control is a known normal tissue of the same tissue type as in the patient sample. In some embodiments the level of the expression product in the sample is increased relative to the control.

The invention also provides methods for detecting a cancerous cell in a patient sample comprising detecting evidence of an expression product of SEMA4D. Evidence of expression of the gene in the sample indicates that a cell in the sample is cancerous. In some embodiments the cell is a breast cell, lung cell, liver cell, lymphoid cell, ovary cell, pancreas cell, prostate cell, uterine cell or skin cell. In some embodiments evidence of the expression product is detected using an antibody linked to an imaging agent.

The invention provides methods for assessing the progression of cancer in a patient comprising comparing the level of an expression product of SEMA4D in a biological sample at a first time point to a level of the same expression product at a second time point. A change in the level of the expression product at the second time point relative to the first time point is indicative of the progression of the cancer. In some embodiments the cancer is breast cancer, liver cancer, lung cancer, lymphoid cancer, ovary cancer, pancreas cancer, prostate cancer, uterine cancer or skin cancer.

The invention also provides methods of diagnosing cancer comprising (a) measuring a level of mRNA of SEMA4D in a first sample wherein the first sample comprises a first tissue type of a first individual; and (b) comparing the level of mRNA in (a) to a control. Detection of at least a two fold difference between the level of mRNA in (a) and the level of the mRNA in the second sample or the third sample indicates that the first individual has or is predisposed to cancer. In some embodiments the control sample comprises a normal tissue type of the first individual. In some embodiments the control sample comprises a normal tissue type from an unaffected individual. In some embodiments, at least a three fold difference between the level of mRNA in the first sample and the control indicates that the first individual has or is predisposed to cancer.

The invention provides methods of screening for anti-cancer activity comprising (a) contacting a cell that expresses SEMA4D with a candidate anti-cancer agent; and (b) detecting at least a two fold difference between the level of gene expression in the cell in the presence and in the absence of the candidate anti-cancer agent. At least a two fold difference between the level of gene expression in the cell in the presence compared to the level level of gene expression in the cell in the absence of the candidate anti-cancer agent indicates that the candidate anti-cancer agent has anti-cancer activity. In some embodiments at least a three fold difference between the level of gene expression in the cell in the presence and in the absence of the candidate anti-cancer agent indicates that the candidate anti-cancer agent has anti-cancer activity. In some embodiments the candidate anti-cancer agent is an antibody, small organic compound, small inorganic compound, or polynucleotide. In some embodiments the candidate anti-cancer agent is a monoclonal antibody. In some embodiments the candidate anti-cancer agent is a human or humanized antibody. In some embodiments the polynucleotide is an antisense oligonucleotide. In some embodiments the polynucleotide is an oligonucleotide having a sequence of SEQ ID NO:7.

The invention also provides kits for the diagnosis or detection of cancer in a mammal. In some embodiments the kit comprises an antibody or fragment thereof, or an immunoconjugate or fragment thereof. In some embodiments the antibody or fragment is capable of specifically binding an SEMA4D tumor cell antigen. The kits further comprise one or more reagents for detecting a binding reaction between the antibody and the tumor cell antigen. In some embodiments the kit comprises instructions for using the kit.

The invention also provides kits for diagnosing cancer. In some embodiments the kis comprise a nucleic acid probe that hybridises under stringent conditions to SEMA4D. The kits also comprise primers for amplifying the cancer-associated gene. In some embodiments the kits comprise instructions for using the kit.

The invention provides methods for treating cancer in a patient. In some embodiments the methods comprises modulating the level of an expression product of SEMA4D. In some embodiments the methods comprise administering to the patient an antibody, a nucleic acid, or a polypeptide that modulates the level of the expression product. In some embodiments the level of the expression product is upregulated or downregulated by at least a 2-fold change. In some embodiments the cancer is treated by the inhibition of tumour growth or the reduction of tumour volume. In some embodiments the cancer is treated by reducing the invasiveness of a cancer cell. In some embodiments the expression product is a protein or mRNA. In some embodiments the expression level of the expression product at a first time point is compared to the expression level of the same expression product at a second time point, wherein an increase or decrease in expression at the second time point relative to the first time point is indicative of the progression of cancer.

The invention also provides methods for treating cancer in a patient comprising modulating an SEMA4D-activity. In some embodiments the SEMA4D activity is cell proliferation, cell growth, cell motility, metastasis, cell migration, cell survival, or tumorigenicity. In some embodiments the methods comprise administering to the patient an antibody, a nucleic acid, or a polypeptide that inhibits the SEMA4D-activity. In some embodiments the antibody is a neutralizing antibody. In some embodiments the antibody is a monoclonal antibody. In some embodiments the monoclonal antibody binds to an SEMA4D polypeptide with an affinity of at least $1\times10^8$ Ka. In some embodiments the monoclonal antibody inhibits one or more of cancer cell growth, tumor formation, cell survival and cancer cell proliferation. In some embodiments the antibody is a monoclonal antibody, a polyclonal antibody, a chimeric antibody, a human antibody, a humanized antibody, a single-chain antibody, a bi-specific antibody, a multi-specific antibody, or a Fab fragment.

The invention also provides methods of treating a cancer in a patient characterized by overexpression of SEMA4D relative to a control. In some embodiments the methods comprise modulating an SEMA4D activity in the patient. In some embodiments the SEMA4D activity is selected from the group consisting of cell proliferation, cell growth, cell motility, metastasis, cell migration, cell survival, gene expression and tumorigenicity. In some embodiments the cancer is selected from the group consisting of cervical cancer, kidney cancer, ovarian cancer, pancreatic cancer and skin cancer. In some embodiments the methods comprise administering to the patient an antibody, a nucleic acid, or a polypeptide that inhibits the SEMA4D-activity.

The present invention also provides methods for identifying a patient as susceptible to treatment with an antibody that binds to an expression product of SEMA4, comprising measuring the level of the expression product of the gene in a biological sample from that patient.

The invention also provides compositions for treating, diagnosing or detecting cancer. In some embodiments the compositions comprise an antibody or oligonucleotide specific for an expression product of SEMA4D. In some embodiments the compositions further comprise a conventional cancer medicament. In some embodiments the compositions are pharmaceutical compositions. In some embodiments the compositions are sterile injectables.

The invention further provides assays for identifying a candidate agent that modulates the growth of a cancerous cell, comprising a) detecting the level of expression of one or more (i.e. 1, 2, 3, 4, 5, 6, 7, 8, 9, 10, or more) expression products of SEMA4D in the presence of the candidate agent; and b) comparing that level of expression with the level of expression in the absence of the candidate agent, wherein a difference in expression indicates that the candidate agent modulates the level of expression of the expression product of the cancer-associated gene.

The invention also provides methods for identifying an agent that modifies the expression level of SEMA4D, comprising: a) contacting a cell expressing SEMA4D as listed in any of the above-described embodiments of the invention with a candidate agent, and b) determining the effect of the candidate agent on the cell, wherein a change in expression level indicates that the candidate agent is able to modulate expression.

In some embodiments the candidate agent is a polynucleotide, a polypeptide, an antibody or a small organic molecule.

The invention also provides methods for detecting cancer in a biological sample comprising determining the sequence or expression level of SEMA4D which, as described herein, is correlated to lymphoma, leukemia, melanoma, breast cancer, colon cancer, kidney cancer, liver cancer, lung cancer, ovary cancer, pancreatic cancer, prostate cancer, uterine cancer, cervical cancer, bladder cancer, stomach cancer or skin cancer.

DEFINITIONS

The present invention identifies that SEMA4D is implicated in the incidence of cancer. This gene is therefore referred to as "SEMA4D gene".

By "SEMA4D" we mean the gene "semaphorin 4D" referred to by gene locus ID 10507 in the NCBI public database, having an mRNA referred to under accession number NM_006378 (SEQ ID NO: 1) and encoding the polypeptide referred to under accession number NP_006369 (SEQ ID NO: 2). Related sequences include BC054500 (SEQ ID NO:3=nucleotide sequence; SEQ ID NO:4=amino acid sequence), AAH54500 (SEQ ID NO: 5), BX648216 (SEQ ID NO: 6), U60800 (SEQ ID NO:7=nucleotide sequence; SEQ ID NO:8=amino acid sequence), AAC50810 (SEQ ID NO: 9) and Q92854 (SEQ ID NO: 10). SEMA4D is a membrane bound protein.

Thus, SEMA4D polypeptides encoded by this gene are referred to as "cancer-associated polypeptides" or "cancer-associated proteins". Nucleic acid sequences that encode these cancer-associated polypeptides are referred to as "cancer-associated polynucleotides". Cells which encode and/or express the SEMA4D gene are referred to as "cancer-associated cells". Cells which encode the SEMA4D gene are said to have a "cancer-associated genotype". Cells which express a cancer-associated protein are said to have a "cancer-associated phenotype". "Cancer-associated sequences" refers to both polypeptide and polynucleotide sequences derived from SEMA4D gene. "Cancer-associated nucleic acids" includes the DNA comprising the SEMA4D gene, as well as mRNA and cDNA derived from that gene.

"Associated" in this context means that the SEMA4D nucleotide or protein sequences are differentially expressed, activated, inactivated or altered in cancers as compared to normal tissue. As outlined below, cancer-associated sequences include those that are up-regulated (i.e. expressed at a higher level), as well as those that are down-regulated (i.e. expressed at a lower level), in cancers. Cancer-associated sequences also include sequences that have been altered (i.e., truncated sequences or sequences with substitutions, deletions or insertions, including point mutations) and show either the same expression profile or an altered profile. Generally, the cancer-associated sequences are from humans; however, as will be appreciated by those in the art, cancer-associated sequences from other organisms may be useful in animal models of disease and drug evaluation; thus, other cancer-associated sequences may be identified, from vertebrates, including mammals, including rodents (rats, mice, hamsters, guinea pigs, etc.), primates, and farm animals (including sheep, goats, pigs, cows, horses, etc). In some cases, prokaryotic cancer-associated sequences may be useful. Cancer-associated sequences from other organisms may be obtained using the techniques outlined below.

Cancer-associated sequences include recombinant nucleic acids. By the term "recombinant nucleic acid" herein is meant nucleic acid, originally formed in vitro, in general, by the manipulation of nucleic acid by polymerases and endonucleases, in a form not normally found in nature. Thus a recombinant nucleic acid is also an isolated nucleic acid, in a linear form, or cloned in a vector formed in vitro by ligating DNA molecules that are not normally joined, are both considered recombinant for the purposes of this invention. It is understood that once a recombinant nucleic acid is made and reintroduced into a host cell or organism, it will replicate using the in vivo cellular machinery of the host cell rather than in vitro manipulations; however, such nucleic acids, once produced recombinantly, although subsequently replicated in vivo, are still considered recombinant or isolated for the purposes of the invention. As used herein a "polynucleotide" or "nucleic acid" is a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., phosphorothioates, phosphorodithioates, etc.), those containing pendant moieties, such as, for example proteins (including e.g., nucleases, toxins, antibodies, signal peptides, poly-L-lysine, etc.), those with intercalators (e.g., acridine, psoralen, etc.), those containing chelators (e.g., metals, radioactive metals, etc.), those containing alkylators, those with modified linkages (e.g., alpha anomeric nucleic acids, etc.), as well as unmodified forms of the polynucleotide.

As used herein, a polynucleotide "derived from" a designated sequence refers to a polynucleotide sequence which is comprised of a sequence of approximately at least about 6 nucleotides, at least about 8 nucleotides, at least about 10-12 nucleotides, and at least about 15-20 nucleotides corresponding to a region of the designated nucleotide sequence. "Corresponding" means homologous to or complementary to the designated sequence. In some embodiments, the sequence of the region from which the polynucleotide is derived is homologous to or complementary to a sequence that is unique to a cancer-associated gene.

A "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, constituting at least about 0.5%, or at least about 5% by weight of the total protein in a given sample. A substantially pure protein comprises about 50-75%, at least about 80%, or at least about 90% by weight of the total protein. The definition includes the production of a cancer-associated protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

As used herein, the term "tag," "sequence tag" or "primer tag sequence" refers to an oligonucleotide with specific nucleic acid sequence that serves to identify a batch of polynucleotides bearing such tags therein. Polynucleotides from the same biological source are covalently tagged with a specific sequence tag so that in subsequent analysis the polynucleotide can be identified according to its source of origin. The sequence tags also serve as primers for nucleic acid amplification reactions.

A "microarray" is a linear or two-dimensional array of preferably discrete regions, each having a defined area, formed on the surface of a solid support. The density of the discrete regions on a microarray is determined by the total numbers of target polynucleotides to be detected on the surface of a single solid phase support, preferably at least about $50/cm^2$, more preferably at least about $100/cm^2$, even more preferably at least about $500/cm^2$, and still more preferably at least about $1,000/cm^2$. As used herein, a DNA microarray is an array of oligonucleotide primers placed on a chip or other surfaces used to amplify or clone target polynucleotides. Since the position of each particular group of primers in the array is known, the identities of the target polynucleotides can be determined based on their binding to a particular position in the microarray.

A "linker" is a synthetic oligodeoxyribonucleotide that contains a restriction site. A linker may be blunt end-ligated onto the ends of DNA fragments to create restriction sites that can be used in the subsequent cloning of the fragment into a vector molecule.

The term "label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical, chemical, or any other appropriate means. The term "label" is used to refer to any chemical group or moiety having a detectable physical property or any compound capable of causing a chemical group or moiety to exhibit a detectable physical property, such as an enzyme that catalyzes conversion of a substrate into a detectable product. The term "label" also encompasses compounds that inhibit the expression of a particular physical property. The label may also be a compound that is a member of a binding pair, the other member of which bears a detectable physical property.

The term "support" refers to conventional supports such as beads, particles, dipsticks, fibers, filters, membranes, and silane or silicate supports such as glass slides.

The term "amplify" is used in the broad sense to mean creating an amplification product which may include, for example, additional target molecules, or target-like molecules or molecules complementary to the target molecule, which molecules are created by virtue of the presence of the target molecule in the sample. In the situation where the target is a nucleic acid, an amplification product can be made enzymatically with DNA or RNA polymerases or reverse transcriptases.

As used herein, a "biological sample" refers to a sample of tissue or fluid isolated from an individual, including but not limited to, for example, blood, plasma, serum, spinal fluid, lymph fluid, skin, respiratory, intestinal and genitourinary tracts, tears, saliva, milk, cells (including but not limited to blood cells), tumors, organs, and also samples of in vitro cell culture constituents.

The term "biological sources" as used herein refers to the sources from which the target polynucleotides are derived. The source can be of any form of "sample" as described above, including but not limited to, cell, tissue or fluid. "Different biological sources" can refer to different cells/tissues/organs of the same individual, or cells/tissues/organs from different individuals of the same species, or cells/tissues/organs from different species.

Cancer-Associated Genes

SEMA4D is a membrane bound protein. This gene underwent type I and II integrations of the MMTV and MLV proviruses and integration was found in 8 cases. This gene was found to be overexpressed at the mRNA level using patients' tumour samples in 33% of breast cancer tissue sampled, 87% of ovarian cancer tissue sampled, 40% of pancreatic cancer tissue sampled. This gene was also found to be overexpressed in colon and prostate tumors sampled (t-test). This means that this gene is correlated with breast, pancreas, ovarian, colon and prostate cancer and is therefore a promising target for the diagnosis and therapy of these diseases.

The expression of this gene alone may be sufficient to cause cancer. Alternatively an increase in expression of this gene may be sufficient to cause cancer. In a further alternative, cancer may be induced when the expression of this gene reaches or exceeds a threshold level. The threshold level may be represented as a percentage increase or decrease in expression of the gene when compared with that in a "normal" control level of expression. In any event, changes in expression levels of SEMA4D are correlated with cancer.

The invention also allows the use of homologs, fragments, and functional equivalents of the above-referenced cancer-associated genes. Homology can be based on the full gene sequence referenced above and is generally determined as outlined below, using homology programs or hybridization conditions. A homolog of a cancer-associated gene has preferably greater than about 75% (i.e. at least 80, at least 85, at least 90, at least 92, at least 94, at least 95, at least 96, at least 97, at least 98, at least 99% or more) homology with the cancer-associated gene. Such homologs may include splice variants, deletion, addition and/or substitution mutants and generally have functional similarity.

Homology in this context means sequence similarity or identity. One comparison for homology purposes is to compare the sequence containing sequencing errors to the correct sequence. This homology will be determined using standard techniques known in the art, including, but not limited to, the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387-395 (1984), in some embodiments using the default settings, or by inspection.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989). Useful PILEUP parameters include a default gap weight of 3.00, a default gap length weight of 0.10, and weighted end gaps.

Another example of a useful algorithm is the BLAST (Basic Local Alignment Search Tool) algorithm, described in Altschul et al., J. Mol. Biol. 215, 403-410, (1990) and Karlin et al., PNAS USA 90:5873-5787 (1993). A particularly useful BLAST program is the WU-BLAST-2 program which was obtained from Altschul et al., Methods in Enzymology, 266: 460-480 (1996); http://blast.wustl.edu/]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A percent amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment may include the introduction of gaps in the sequences to be aligned. In addition, for sequences which contain either more or fewer nucleotides than those of the cancer-associated genes, it is understood that the percentage of homology will be determined based on the number of homologous nucleosides in relation to the total number of nucleosides. Thus homology of sequences shorter than those of the sequences identified herein will be determined using the number of nucleosides in the shorter sequence.

In some embodiments of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC ("saline sodium citrate"; 9 mM NaCl, 0.9 mM sodium citrate), 0.5% SDS, 1.0 mM EDTA (pH 8.0); hybridizing at 50-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in some embodiments, suitable highly stringent hybridization conditions include those described above, with the exception that the temperature of hybridization is increased, e.g., to 60-65° C., or 65-70° C. Stringent conditions may also be achieved with the addition of destabilizing agents such as formamide.

Thus nucleic acids that hybridize under high stringency to the nucleic acids identified throughout the present application and sequence listing, or their complements, are considered cancer-associated sequences. High stringency conditions are known in the art; see for example Maniatis et al., Molecular Cloning: A Laboratory Manual, 2nd Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for longer probes (e.g. greater than 50 nucleotides). In another embodiment, less stringent hybridization conditions are used; for example, moderate or low stringency conditions may be used, as are known in the art; see Maniatis and Ausubel, supra, and Tijssen, supra.

Detection of Cancer-Associated Gene Expression

The cancer-associated gene may be cloned and, if necessary, its constituent parts recombined to form the entire cancer-associated nucleic acid. Once isolated from its natural source, e.g., contained within a plasmid or other vector or excised therefrom as a linear nucleic acid segment, the recombinant cancer-associated nucleic acid can be further used as a probe to identify and isolate other cancer-associated nucleic acids, for example additional coding regions. It can also be used as a "precursor" nucleic acid to make modified or variant cancer-associated nucleic acids and proteins. The nucleotide sequence of the cancer-associated gene can also be used to design probes specific for the cancer-associated gene.

The cancer-associated nucleic acids may be used in several ways. Nucleic acid probes hybridizable to cancer-associated nucleic acids can be made and attached to biochips to be used in screening and diagnostic methods, or for gene therapy and/or antisense applications. Alternatively, the cancer-associated nucleic acids that include coding regions of cancer-associated proteins can be put into expression vectors for the expression of cancer-associated proteins, again either for screening purposes or for administration to a patient.

One such system for quantifying gene expression is kinetic polymerase chain reaction (PCR). Kinetic PCR allows for the simultaneous amplification and quantification of specific nucleic acid sequences. The specificity is derived from synthetic oligonucleotide primers designed to preferentially adhere to single-stranded nucleic acid sequences bracketing the target site. This pair of oligonucleotide primers forms specific, non-covalently bound complexes on each strand of the target sequence. These complexes facilitate in vitro transcription of double-stranded DNA in opposite orientations. Temperature cycling of the reaction mixture creates a continuous cycle of primer binding, transcription, and re-melting of the nucleic acid to individual strands. The result is an exponential increase of the target dsDNA product. This product can be quantified in real time either through the use of an intercalating dye or a sequence specific probe. SYBR® Greene I, is an example of an intercalating dye, that preferentially binds to dsDNA resulting in a concomitant increase in the fluorescent signal. Sequence specific probes, such as used with TaqMan® technology, consist of a fluorochrome and a quenching molecule covalently bound to opposite ends of an oligonucleotide. The probe is designed to selectively bind the target DNA sequence between the two primers. When the DNA strands are synthesized during the PCR reaction, the fluorochrome is cleaved from the probe by the exonuclease activity of the polymerase resulting in signal dequenching. The probe signaling method can be more specific than the intercalating dye method, but in each case, signal strength is proportional to the dsDNA product produced. Each type of quantification method can be used in multi-well liquid phase arrays with each well representing primers and/or probes specific to nucleic acid sequences of interest. When used with messenger RNA preparations of tissues or cell lines, an array of probe/primer reactions can simultaneously quantify the expression of multiple gene products of interest. See Germer, S., et al., Genome Res. 10:258-266 (2000); Heid, C. A., et al., Genome Res. 6, 986-994 (1996).

Recent developments in DNA microarray technology make it possible to conduct a large scale assay of a plurality of target cancer-associated nucleic acid molecules on a single solid phase support. U.S. Pat. No. 5,837,832 (Chee et al.) and related patent applications describe immobilizing an array of oligonucleotide probes for hybridization and detection of specific nucleic acid sequences in a sample. Target polynucleotides of interest isolated from a tissue of interest are hybridized to the DNA chip and the specific sequences detected based on the target polynucleotides' preference and degree of hybridization at discrete probe locations. One important use of arrays is in the analysis of differential gene expression, where the profile of expression of genes in different cells, often a cell of interest and a control cell, is compared and any differences in gene expression among the respective cells are identified. Such information is useful for the identification of the types of genes expressed in a particular cell or tissue type and diagnosis of cancer conditions based on the expression profile.

Typically, RNA from the sample of interest is subjected to reverse transcription to obtain labeled cDNA. See U.S. Pat. No. 6,410,229 (Lockhart et al.) The cDNA is then hybridized to oligonucleotides or cDNAs of known sequence arrayed on a chip or other surface in a known order. The location of the oligonucleotide to which the labeled cDNA hybridizes provides sequence information on the cDNA, while the amount of labeled hybridized RNA or cDNA provides an estimate of the relative representation of the RNA or cDNA of interest. See Schena, et al. Science 270:467-470 (1995). For example, use of a cDNA microarray to analyze gene expression patterns in human cancer is described by DeRisi, et al. (Nature Genetics 14:457-460 (1996)).

Nucleic acid probes corresponding to cancer-associated nucleic acids may be made. Typically, these probes are synthesized based on the disclosed cancer-associated genes. The nucleic acid probes attached to the biochip are designed to be substantially complementary to the cancer-associated nucleic acids, i.e. the target sequence (either the target sequence of the sample or to other probe sequences, for example in sandwich assays), such that specific hybridization of the target sequence and the probes of the present invention occurs. As outlined below, this complementarity need not be perfect, in that there may be any number of base pair mismatches that will interfere with hybridization between the target sequence and the single stranded nucleic acids of the present invention. It is expected that the overall homology of the genes at the nucleotide level will be about 40% or greater, about 60% or greater, or about 80% or greater; and in addition that there will be corresponding contiguous sequences of about 8-12 nucleotides or longer. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein. Whether or not a sequence is unique to a cancer-associated gene according to this invention can be determined by techniques known to those of skill in the art. For example, the sequence can be compared to sequences in databanks, e.g., GeneBank, to determine whether it is present in the uninfected host or other organisms. The sequence can also be compared to the known sequences of other viral agents, including those that are known to induce cancer.

In some embodiments, probes suitable for the detection of SEMA4D expression are specific for a non-conserved region of SEMA4D. 'Non-conserved region' refers to a region of lower than average homology with other members of the SEMAPHORIN family. Preferably, similarity to other SEMAPHORIN family members in these non-conserved regions is lower than 50%.

Suitable primers and probes for the detection of SEMA4D using Q-PCR are a) GGTGCCTGTGTTCTATGCACTCT SEQ ID NO:1, b) GACAGGTTGTAGGCGCACACT SEQ ID NO:2; and c) ACCCCACAGCTGAACAACGTGGG SEQ ID NO:3.

A nucleic acid probe is generally single stranded but can be partly single and partly double stranded. The strandedness of the probe is dictated by the structure, composition, and properties of the target sequence. In general, the oligonucleotide probes range from about 6, 8, 10, 12, 15, 20, 30 to about 100 bases long, from about 10 to about 80 bases, or from about 30 to about 50 bases. In some embodiments entire genes are used as probes. In some embodiments, much longer nucleic acids can be used, up to hundreds of bases. The probes are sufficiently specific to hybridize to complementary template sequence under conditions known by those of skill in the art. The number of mismatches between the probes sequences and their complementary template (target) sequences to which they hybridize during hybridization generally do not exceed 15%, 10% or 5%, as determined by FASTA (default settings).

Oligonucleotide probes can include the naturally-occurring heterocyclic bases normally found in nucleic acids (uracil, cytosine, thymine, adenine and guanine), as well as modified bases and base analogues. Any modified base or base analogue compatible with hybridization of the probe to a target sequence is useful in the practice of the invention. The sugar or glycoside portion of the probe can comprise deoxyribose, ribose, and/or modified forms of these sugars, such as, for example, 2'-O-alkyl ribose. In some embodiments, the sugar moiety is 2'-deoxyribose; however, any sugar moiety that is compatible with the ability of the probe to hybridize to a target sequence can be used.

The nucleoside units of the probe may be linked by a phosphodiester backbone, as is well known in the art. In some embodiments, internucleotide linkages can include any linkage known to one of skill in the art that is compatible with specific hybridization of the probe including, but not limited to phosphorothioate, methylphosphonate, sulfamate (e.g., U.S. Pat. No. 5,470,967) and polyamide (i.e., peptide nucleic acids). Peptide nucleic acids are described in Nielsen et al. (1991) Science 254: 1497-1500, U.S. Pat. No. 5,714,331, and Nielsen (1999) Curr. Opin. Biotechnol. 10:71-75.

The probe can be a chimeric molecule; i.e., can comprise more than one type of base or sugar subunit, and/or the linkages can be of more than one type within the same primer. The probe can comprise a moiety to facilitate hybridization to its target sequence, as are known in the art, for example, intercalators and/or minor groove binders. Variations of the bases, sugars, and internucleoside backbone, as well as the presence of any pendant group on the probe, will be compatible with the ability of the probe to bind, in a sequence-specific fashion, with its target sequence. A large number of structural modifications, both known and to be developed, are possible within these bounds. Advantageously, the probes according to the present invention may have structural characteristics such that they allow the signal amplification, such structural characteristics being, for example, branched DNA probes as those described by Urdea et al. (Nucleic Acids Symp. Ser., 24:197-200 (1991)) or in the European Patent No. EP-0225,807. Moreover, synthetic methods for preparing the various heterocyclic bases, sugars, nucleosides and nucleotides that form the probe, and preparation of oligonucleotides of specific predetermined sequence, are well-developed and known in the art. A method for oligonucleotide synthesis incorporates the teaching of U.S. Pat. No. 5,419,966.

Multiple probes may be designed for a particular target nucleic acid to account for polymorphism and/or secondary structure in the target nucleic acid, redundancy of data and the like. In some embodiments, where more than one probe per sequence is used, either overlapping probes or probes to different sections of a single target cancer-associated gene are used. That is, two, three, four or more probes, with three being preferred, are used to build in a redundancy for a particular target. The probes can be overlapping (i.e. have some sequence in common), or specific for distinct sequences of SEMA4D. When multiple target polynucleotides are to be detected according to the present invention, each probe or probe group corresponding to a particular target polynucleotide is situated in a discrete area of the microarray.

Probes may be in solution, such as in wells or on the surface of a micro-array, or attached to a solid support. Examples of solid support materials that can be used include a plastic, a ceramic, a metal, a resin, a gel and a membrane. Useful types of solid supports include plates, beads, magnetic material, microbeads, hybridization chips, membranes, crystals, ceramics and self-assembling monolayers. Some embodiments comprise a two-dimensional or three-dimensional matrix, such as a gel or hybridization chip with multiple probe binding sites (Pevzner et al., J. Biomol. Struc. & Dyn. 9:399-410, 1991; Maskos and Southern, Nuc. Acids Res. 20:1679-84, 1992). Hybridization chips can be used to construct very large probe arrays that are subsequently hybridized with a target nucleic acid. Analysis of the hybridization pattern of the chip can assist in the identification of the target nucleotide sequence. Patterns can be manually or computer analyzed, but it is clear that positional sequencing by hybridization lends itself to computer analysis and automation. Algorithms and software, which have been developed for sequence reconstruction, are applicable to the methods described herein (R. Drmanac et al., J. Biomol. Struc. & Dyn. 5:1085-1102, 1991; P. A. Pevzner, J. Biomol. Struc. & Dyn. 7:63-73, 1989).

As will be appreciated by those in the art, nucleic acids can be attached or immobilized to a solid support in a wide variety of ways. By "immobilized" herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as streptavidin, to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

Nucleic acid probes may be attached to the solid support by covalent binding such as by conjugation with a coupling agent or by, covalent or non-covalent binding such as electrostatic interactions, hydrogen bonds or antibody-antigen coupling, or by combinations thereof. Typical coupling agents include biotin/avidin, biotin/streptavidin, *Staphylo-*

*coccus aureus* protein A/IgG antibody Fc fragment, and streptavidin/protein A chimeras (T. Sano and C. R. Cantor, Bio/Technology 9:1378-81 (1991)), or derivatives or combinations of these agents. Nucleic acids may be attached to the solid support by a photocleavable bond, an electrostatic bond, a disulfide bond, a peptide bond, a diester bond or a combination of these sorts of bonds. The array may also be attached to the solid support by a selectively releasable bond such as 4,4'-dimethoxytrityl or its derivative. Derivatives which have been found to be useful include 3 or 4 [bis-(4-methoxyphenyl)]-methyl-benzoic acid, N-succinimidyl-3 or 4 [bis-(4-methoxyphenyl)]-methyl-benzoic acid, N-succinimidyl-3 or 4 [bis-(4-methoxyphenyl)]-hydroxymethyl-benzoic acid, N-succinimidyl-3 or 4 [bis-(4-methoxyphenyl)]-chloromethyl-benzoic acid, and salts of these acids.

Probes may be attached to biochips in a wide variety of ways, as will be appreciated by those in the art. As described herein, the nucleic acids can either be synthesized first, with subsequent attachment to the biochip, or can be directly synthesized on the biochip.

Biochips comprise a suitable solid substrate. By "substrate" or "solid support" or other grammatical equivalents herein is meant any material that can be modified to contain discrete individual sites appropriate for the attachment or association of the nucleic acid probes and is amenable to at least one detection method. The solid phase support of the present invention can be of any solid materials and structures suitable for supporting nucleotide hybridization and synthesis. Preferably, the solid phase support comprises at least one substantially rigid surface on which the primers can be immobilized and the reverse transcriptase reaction performed. The substrates with which the polynucleotide microarray elements are stably associated may be fabricated from a variety of materials, including plastics, ceramics, metals, acrylamide, cellulose, nitrocellulose, glass, polystyrene, polyethylene vinyl acetate, polypropylene, polymethacrylate, polyethylene, polyethylene oxide, polysilicates, polycarbonates, Teflon®, fluorocarbons, nylon, silicon rubber, polyanhydrides, polyglycolic acid, polylactic acid, polyorthoesters, polypropylfumerate, collagen, glycosaminoglycans, and polyamino acids. Substrates may be two-dimensional or three-dimensional in form, such as gels, membranes, thin films, glasses, plates, cylinders, beads, magnetic beads, optical fibers, woven fibers, etc. One form of array is a three-dimensional array. One type of three-dimensional array is a collection of tagged beads. Each tagged bead has different primers attached to it. Tags are detectable by signaling means such as color (Luminex, Illumina) and electromagnetic field (Pharmaseq) and signals on tagged beads can even be remotely detected (e.g., using optical fibers). The size of the solid support can be any of the standard microarray sizes, useful for DNA microarray technology, and the size may be tailored to fit the particular machine being used to conduct a reaction of the invention. In general, the substrates allow optical detection and do not appreciably fluoresce.

The surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference). In addition, in some cases, additional linkers, such as alkyl groups (including substituted and heteroalkyl groups) may be used.

The oligonucleotides may be synthesized as is known in the art, and then attached to the surface of the solid support. As will be appreciated by those skilled in the art, either the 5' or 3' terminus may be attached to the solid support, or attachment may be via an internal nucleoside. In an additional embodiment, the immobilization to the solid support may be very strong, yet non-covalent. For example, biotinylated oligonucleotides can be made, which bind to surfaces covalently coated with streptavidin, resulting in attachment.

Arrays may be produced according to any convenient methodology, such as preforming the polynucleotide microarray elements and then stably associating them with the surface. Alternatively, the oligonucleotides may be synthesized on the surface, as is known in the art. A number of different array configurations and methods for their production are known to those of skill in the art and disclosed in WO 95/25116 and WO 95/35505 (photolithographic techniques), U.S. Pat. No. 5,445,934 (in situ synthesis by photolithography), U.S. Pat. No. 5,384,261 (in situ synthesis by mechanically directed flow paths); and U.S. Pat. No. 5,700,637 (synthesis by spotting, printing or coupling); the disclosure of which are herein incorporated in their entirety by reference. Another method for coupling DNA to beads uses specific ligands attached to the end of the DNA to link to ligand-binding molecules attached to a bead. Possible ligand-binding partner pairs include biotin-avidin/streptavidin, or various antibody/antigen pairs such as digoxygenin-antidigoxygenin antibody (Smith et al., "Direct Mechanical Measurements of the Elasticity of Single DNA Molecules by Using Magnetic Beads," Science 258:1122-1126 (1992)). Covalent chemical attachment of DNA to the support can be accomplished by using standard coupling agents to link the 5'-phosphate on the DNA to coated microspheres through a phosphoamidate bond. Methods for immobilization of oligonucleotides to solid-state substrates are well established. See Pease et al., Proc. Natl. Acad. Sci. USA 91(11):5022-5026 (1994). One method of attaching oligonucleotides to solid-state substrates is described by Guo et al., Nucleic Acids Res. 22:5456-5465 (1994). Immobilization can be accomplished either by in situ DNA synthesis (Maskos and Southern, Nucleic Acids Research, 20:1679-1684 (1992) or by covalent attachment of chemically synthesized oligonucleotides (Guo et al., supra) in combination with robotic arraying technologies.

Expression Products

The term "expression products" as used herein refers to both nucleic acids, including, for example, mRNA, and polypeptide products produced by transcription and/or translation of the SEMA4D gene.

The polypeptides may be in the form of a mature protein or may be a pre-, pro- or prepro-protein that can be activated by cleavage of the pre-, pro- or prepro-portion to produce an active mature polypeptide. In such polypeptides, the pre-, pro- or prepro-sequence may be a leader or secretory sequence or may be a sequence that is employed for purification of the mature polypeptide sequence. Such polypeptides are referred to as "cancer-associated polypeptides".

The term "cancer-associated polypeptides" also includes variants such as fragments, homologs, fusions and mutants. Homologous polypeptides have at least 80% or more (i.e. at least 85, at least 90, at least 91, at least 92, at least 93, at least 94, at least 95, at least 96, at least 97, at least 98, at least 99%) sequence identity with a cancer-associated polypeptide as referred to above, as determined by the Smith-Waterman homology search algorithm using an affine gap search with a gap open penalty of 12 and a gap extension penalty of 2, BLOSUM matrix of 62. The Smith-Waterman homology search algorithm is taught in Smith and Waterman, Adv. Appl. Math. (1981) 2: 482-489. The variant polypeptides can be naturally or non-naturally glycosylated, i.e., the polypeptide has a glycosylation pattern that differs from the glycosylation pattern found in the corresponding naturally occurring protein.

Mutants can include amino acid substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Conservative amino acid substitutions are those that preserve the general charge, hydrophobicity/hydrophilicity, and/or steric bulk of the amino acid substituted. Variants of these products can be designed so as to retain or have enhanced biological activity of a particular region of the protein (e.g., a functional domain and/or, where the polypeptide is a member of a protein family, a region associated with a consensus sequence). Such variants may then be used in methods of detection or treatment. Selection of amino acid alterations for production of variants can be based upon the accessibility (interior vs. exterior) of the amino acid (see, e.g., Go et al, Int. J. Peptide Protein Res. (1980) 15:211), the thermostability of the variant polypeptide (see, e.g., Querol et al., Prot. Eng. (1996) 9:265), desired glycosylation sites (see, e.g., Olsen and Thomsen, J. Gen. Microbiol. (1991) 137:579), desired disulfide bridges (see, e.g., Clarke et al., Biochemistry (1993) 32:4322; and Wakarchuk et al., Protein Eng. (1994) 7:1379), desired metal binding sites (see, e.g., Toma et al., Biochemistry (1991) 30:97, and Haezerbrouck et al., Protein Eng. (1993) 6:643), and desired substitutions within proline loops (see, e.g., Masul et al., Appl. Env. Microbiol. (1994) 60:3579). Cysteine-depleted muteins can be produced as disclosed in U.S. Pat. No. 4,959,314.

Variants also include fragments of the polypeptides disclosed herein, particularly biologically active fragments and/or fragments corresponding to functional domains. Fragments of interest will typically be at least about 8 amino acids (aa) 10 aa, 15 aa, 20 aa, 25 aa, 30 aa, 35 aa, 40 aa, to at least about 45 aa in length, usually at least about 50 aa in length, at least about 75 aa, at least about 100 aa, at least about 125 aa, at least about 150 aa in length, at least about 200 aa, at least about 300 aa, at least about 400 aa and can be as long as 500 aa in length or longer, but will usually not exceed about 1000 aa in length, where the fragment will have a stretch of amino acids that is identical to a polypeptide encoded by a polynucleotide having a sequence of any one of the polynucleotide sequences provided herein, or a homolog thereof. The protein variants described herein are encoded by polynucleotides that are within the scope of the invention. The genetic code can be used to select the appropriate codons to construct the corresponding variants.

Altered levels of expression of the SEMA4D gene may indicate that the gene and its products play a role in cancers. In some embodiments, a two-fold increase or decrease in the amount of complex formed is indicative of disease. In some embodiments, a 3-fold, 4-fold, 5-fold, 10-fold, 20-fold, 50-fold or even 100-fold increase or decrease in the amount of complex formed is indicative of disease.

Cancer-associated polypeptides may be shorter or longer than the wild type amino acid sequences, and the equivalent coding mRNAs may be similarly modified as compared to the wild type mRNA. Thus, included within the definition of cancer-associated polypeptides are portions or fragments of the wild type sequences herein. In addition, as outlined above, the cancer-associated genes may be used to obtain additional coding regions, and thus additional protein sequence, using techniques known in the art.

In some embodiments, the cancer-associated polypeptides are derivative or variant cancer-associated polypeptides as compared to the wild-type sequence. That is, as outlined more fully below, the derivative cancer-associated polypeptides will contain at least one amino acid substitution, deletion or insertion. The amino acid substitution, insertion or deletion may occur at any residue within the cancer-associated polypeptides.

Also included are amino acid sequence variants of cancer-associated polypeptides. These variants fall into one or more of three classes: substitutional, insertional or deletional variants. These variants ordinarily are prepared by site-specific mutagenesis of nucleotides in the DNA encoding the cancer associated protein, using cassette or PCR mutagenesis or other techniques well known in the art, to produce DNA encoding the variant, and thereafter expressing the DNA in recombinant cell culture as outlined above. However, variant cancer-associated polypeptide fragments having up to about 100-150 residues may be prepared by in vitro synthesis using established techniques. Amino acid sequence variants are characterized by the predetermined nature of the variation, a feature that sets them apart from naturally occurring allelic or interspecies variation of the cancer-associated polypeptide amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed cancer-associated polypeptide variants screened for the optimal combination of desired activity. Techniques for making substitution mutations at predetermined sites in DNA having a known sequence are well known, for example, M13 primer mutagenesis and LAR mutagenesis. Screening of the mutants is done using assays of cancer-associated protein activities.

Amino acid substitutions are typically of single residues, though, of course may be of multiple residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the cancer-associated polypeptide are desired, substitutions are generally made in accordance with the following table:

TABLE 1

| Original Residue | Exemplary Substitutions |
| --- | --- |
| Ala | Ser |
| Arg | Lys |

TABLE 1-continued

| Original Residue | Exemplary Substitutions |
|---|---|
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity occur when substitutions are less conservative than those shown in Table 1. For example, substitutions may be made full length to more significantly affect one or more of the following: the structure of the polypeptide backbone in the area of the alteration (e.g., the alpha-helical or beta-sheet structure); the charge or hydrophobicity of the molecule at the target site; and the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants may also have modified characteristics.

The cancer-associated polypeptides may be themselves expressed and used in methods of detection and treatment. They may be further modified in order to assist with their use in such methods.

Covalent modifications of cancer-associated polypeptides may be utilised, for example in screening. One type of covalent modification includes reacting targeted amino acid residues of a cancer-associated polypeptide with an organic derivatizing agent that is capable of reacting with selected side chains or the N- or C-terminal residues of a cancer-associated polypeptide. Derivatization with bifunctional agents is useful, for instance, for crosslinking cancer-associated polypeptides to a water-insoluble support matrix or surface for use in the method for purifying anti-cancer-associated antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl, threonyl or tyrosyl residues, methylation of the a-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification of the SEMA4D polypeptide included within the scope of this invention comprises altering the native glycosylation pattern of the polypeptide. "Altering the native glycosylation pattern" is intended for purposes herein to mean deleting one or more carbohydrate moieties found in native sequence cancer-associated polypeptide, and/or adding one or more glycosylation sites that are not present in the native sequence cancer-associated polypeptide.

Addition of glycosylation sites to cancer-associated polypeptides may be accomplished by altering the amino acid sequence thereof. The alteration may be made, for example, by the addition of, or substitution by, one or more serine or threonine residues to the native sequence cancer-associated polypeptide (for O-linked glycosylation sites). The cancer-associated amino acid sequence may optionally be altered through changes at the DNA level, particularly by mutating the DNA encoding the cancer-associated polypeptide at preselected bases such that codons are generated that will translate into the desired amino acids.

Another means of increasing the number of carbohydrate moieties on the cancer-associated polypeptide is by chemical or enzymatic coupling of glycosides to the polypeptide. Such methods are described in the art, e.g., in WO 87/05330 published 11 Sep. 1987, and in Aplin and Wriston, LA Crit. Rev. Biochem., pp. 259-306 (1981).

Removal of carbohydrate moieties present on the cancer-associated polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Another type of covalent modification of cancer-associated comprises linking the cancer-associated polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Cancer-associated polypeptides may also be modified in a way to form chimeric molecules comprising a cancer-associated polypeptide fused to another, heterologous polypeptide or amino acid sequence. In some embodiments, such a chimeric molecule comprises a fusion of a cancer-associated polypeptide with a tag polypeptide that provides an epitope to which an anti-tag antibody can selectively bind. The epitope tag is generally placed at the amino- or carboxyl-terminus of the cancer-associated polypeptide, although internal fusions may also be tolerated in some instances. The presence of such epitope-tagged forms of a cancer-associated polypeptide can be detected using an antibody against the tag polypeptide. Also, provision of the epitope tag enables the cancer-associated polypeptide to be readily purified by affinity purification using an anti-tag antibody or another type of affinity matrix that binds to the epitope tag. In an alternative embodiment, the chimeric molecule may comprise a fusion of a cancer-associated polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). Other tag polypeptides include the Flag-peptide (Hopp et al., BioTechnology, 6:1204-1210 (1988)); the KT3 epitope peptide (Martin et al., Science, 255:192-194 (1992)); tubulin epitope peptide (Skinner et al., J. Biol. Chem., 266: 15163-15166 (1991)); and the T7 gene 10 protein peptide tag (Lutz-Freyermuth et al., Proc. Natl. Acad. Sci. USA, 87:6393-6397 (1990)).

Alternatively, other cancer-associated proteins of the cancer-associated protein family, and cancer-associated proteins from other organisms, may be cloned and expressed as outlined below. Thus, probe or degenerate polymerase chain reaction (PCR) primer sequences may be used to find other related cancer-associated proteins from humans or other organisms. As will be appreciated by those in the art, particularly useful probe and/or PCR primer sequences include the unique areas of the cancer-associated nucleic acid sequence. As is generally known in the art, PCR primers may be from about 15 to about 35 or from about 20 to about 30 nucleotides in length, and may contain inosine as needed. The conditions for the PCR reaction are well known in the art.

In addition, as is outlined herein, cancer-associated proteins can be made that are longer than those encoded by SEMA4D gene, for example, by the elucidation of additional sequences, the addition of epitope or purification tags, the addition of other fusion sequences, etc.

Cancer-associated proteins may also be identified as being encoded by cancer-associated nucleic acids. Thus, cancer-associated proteins are encoded by nucleic acids that will hybridize to the SEMA4D gene listed above, or their complements, as outlined herein.

Expression of Cancer Associated Polypeptides

Nucleic acids derived from SEMA4D may be used to make a variety of expression vectors to express cancer-associated proteins which can then be used in screening assays, as mentioned above. The expression vectors may be either self-replicating extrachromosomal vectors or vectors which integrate into a host genome. Generally, these expression vectors include transcriptional and translational regulatory nucleic acid operably linked to the nucleic acid encoding the cancer-associated protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice. The transcriptional and translational regulatory nucleic acid will generally be appropriate to the host cell used to express the cancer-associated protein; for example, transcriptional and translational regulatory nucleic acid sequences from *Bacillus* are preferably used to express the cancer-associated protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In some embodiments, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences that flank the expression construct. The integrating vector may be directed to a specific locus in the host cell by selecting the appropriate homologous sequence for inclusion in the vector. Constructs for integrating vectors are well known in the art.

In some embodiments, the expression vector contains a selectable marker gene to allow the selection of transformed host cells. Selection genes, including antibiotic resistance genes are well known in the art and will vary depending on the host cell used.

The SEMA4D proteins may be produced by culturing a host cell transformed with an expression vector containing nucleic acid encoding a cancer-associated protein, under the appropriate conditions to induce or cause expression of the cancer-associated protein. The conditions appropriate for cancer-associated protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect, plant and animal cells, including mammalian cells. Of particular interest are *Drosophila melano-* gaster cells, *Saccharomyces cerevisiae* and other yeasts, *E. coli, Bacillus subtilis*, Sf9 cells, C129 cells, 293 cells, Neurospora, BHK, CHO, COS, HeLa cells, THP1 cell line (a macrophage cell line) and human cells and cell lines.

In some embodiments SEMA4D proteins are expressed in mammalian cells. Mammalian expression systems are also known in the art, and include retroviral systems. A preferred expression vector system is a retroviral vector system such as is generally described in WO97/27212 (PCT/US97/01019) and WO97/27213 (PCT/US97/01048), both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenylation signals include those derived form SV40.

The methods of introducing exogenous nucleic acid into mammalian hosts, as well as other hosts, are well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In some embodiments, cancer-associated proteins are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the cancer-associated protein in bacteria. The protein is either secreted into the growth media (Gram-positive bacteria) or into the periplasmic space, located between the inner and outer membrane of the cell (Gram-negative bacteria). The bacterial expression vector may also include a selectable marker gene to allow for the selection of bacterial strains that have been transformed. Suitable selection genes include genes that render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris*, and *Streptococcus lividans*, among others. The bacterial expression vectors are transformed into bacterial host cells using techniques well known in the art, such as calcium chloride treatment, electroporation, and others.

Cancer-associated proteins may be produced in insect cells. Expression vectors for the transformation of insect cells, and in particular, baculovirus-based expression vectors, are well known in the art.

In some embodiments, cancer-associated proteins may be produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*.

The SEMA4D protein may also be made as a fusion protein, using techniques well known in the art. Thus, for example, for the creation of monoclonal antibodies. If the desired epitope is small, the cancer-associated protein may be fused to a carrier protein to form an immunogen. Alternatively, the cancer-associated protein may be made as a fusion protein to increase expression, or for other reasons. For example, when the cancer-associated protein is a cancer-associated peptide, the nucleic acid encoding the peptide may be linked to other nucleic acid for expression purposes.

Cancer

In some embodiments, a cancer detected, diagnosed or treated by the methods of the present invention include, but are not limited to, breast cancer (adenocarcinoma of breast: lobular and ductal), colon cancer, ovarian cancer (adenocarcinoma of ovary: serous, papillary serous, endometrioid, and clear cell), pancreatic cancer (adenocarcinoma of pancreas, ductal), prostate cancer, lymphoid cancers (acute T cell leukemia, acute lymphoblastic leukemia), and kidney cancer (renal cell adenocarcinoma).

Antibodies

In some embodiments the invention uses antibodies that specifically bind to SEMA4D polypeptides. The term "specifically binds" means that the antibodies have substantially greater affinity for SEMA4D polypeptide than their affinity for other related polypeptides. As used herein, the term "antibody" refers to intact molecules as well as to fragments thereof, such as Fab, F(ab')2 and Fv, which are capable of binding to the antigenic determinant in question. By "substantially greater affinity" we mean that there is a measurable increase in the affinity for the target cancer-associated polypeptide of the invention as compared with the affinity for other related polypeptide. In some embodiments, the affinity is at least 1.5-fold, 2-fold, 5-fold 10-fold, 100-fold, $10^3$-fold, $10^4$-fold, $10^5$-fold, $10^6$-fold or greater for the target cancer-associated polypeptide.

In some embodiments, the antibodies bind with high affinity with a dissociation constant of $10^{-4}$M or less, $10^{-7}$M or less, $10^{-9}$M or less or with subnanomolar affinity (0.9, 0.8, 0.7, 0.6, 0.5, 0.4, 0.3, 0.2, 0.1 nM or even less). The antibodies may bind specifically to the protease domain.

When SEMA4D polypeptides are to be used to generate antibodies, for example for immunotherapy, in some embodiments the cancer-associated polypeptide should share at least one epitope or determinant with the full-length protein. By "epitope" or "determinant" herein is meant a portion of a protein that will generate and/or bind an antibody or T-cell receptor in the context of MHC. Thus, in some instances, antibodies made to a smaller cancer-associated polypeptide will be able to bind to the full-length protein. In some embodiments, the epitope is unique; that is, antibodies generated to a unique epitope show little or no cross-reactivity.

Polypeptide sequences encoded by SEMA4D may be analyzed to determine certain preferred regions of the polypeptide. Regions of high antigenicity are determined from data by DNASTAR analysis by choosing values that represent regions of the polypeptide that are likely to be exposed on the surface of the polypeptide in an environment in which antigen recognition may occur in the process of initiation of an immune response. For example, the amino acid sequence of a polypeptide encoded by a cancer-associated gene sequence may be analyzed using the default parameters of the DNASTAR computer algorithm (DNASTAR, Inc., Madison, Wis.; see the worldwideweb site at dnastar.com).

In some embodiments, antibodies of the invention are specific for a non-conserved region of SEMA4D. 'Non-conserved region' refers to a region of lower than average homology with other members of the Semaphorin family. In some embodiments similarity to other Semaphorin family members in these non-conserved regions is lower than 50%.

In some embodiments, the antibodies of the present invention bind to orthologs, homologs, paralogs or variants, or combinations and subcombinations thereof, of SEMA4D polypeptides. In some embodiments, the antibodies of the present invention bind to orthologs of SEMA4D polypeptides. In some embodiments, the antibodies of the present invention bind to homologs of SEMA4D polypeptides. In some embodiments, the antibodies of the present invention bind to paralogs of SEMA4D polypeptides. In some embodiments, the antibodies of the present invention bind to variants of SEMA4D polypeptides. In some embodiments, the antibodies of the present invention do not bind to orthologs, homologs, paralogs or variants, or combinations and subcombinations thereof, of SEMA4D polypeptides.

Polypeptide features that may be routinely obtained using the DNASTAR computer algorithm include, but are not limited to, Garnier-Robson alpha-regions, beta-regions, turn-regions, and coil-regions (Garnier et al. J. Mol. Biol., 120: 97 (1978)); Chou-Fasman alpha-regions, beta-regions, and turn-regions (Adv. in Enzymol., 47:45-148 (1978)); Kyte-Doolittle hydrophilic regions and hydrophobic regions (J. Mol. Biol., 157:105-132 (1982)); Eisenberg alpha- and beta-amphipathic regions; Karplus-Schulz flexible regions; Emini surface-forming regions (J. Virol., 55(3):836-839 (1985)); and Jameson-Wolf regions of high antigenic index (CABIOS, 4(1):181-186 (1988)). Kyte-Doolittle hydrophilic regions and hydrophobic regions, Emini surface-forming regions, and Jameson-Wolf regions of high antigenic index (i.e., containing four or more contiguous amino acids having an antigenic index of greater than or equal to 1.5, as identified using the default parameters of the Jameson-Wolf program) can routinely be used to determine polypeptide regions that exhibit a high degree of potential for antigenicity. One approach for preparing antibodies to a protein is the selection and preparation of an amino acid sequence of all or part of the protein, chemically synthesizing the sequence and injecting it into an appropriate animal, typically a rabbit, hamster or a mouse. Oligopeptides can be selected as candidates for the production of an antibody to the cancer-associated protein based upon the oligopeptides lying in hydrophilic regions, which are thus likely to be exposed in the mature protein. Additional oligopeptides can be determined using, for example, the Antigenicity Index, Welling, G. W. et al., FEBS Lett. 188:215-218 (1985), incorporated herein by reference.

The term "antibody" as used herein includes antibody fragments, as are known in the art, including Fab, Fab2, single chain antibodies (Fv for example), chimeric antibodies, etc., either produced by the modification of whole antibodies or those synthesized de novo using recombinant DNA technologies.

The invention also provides antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). The immunization protocol may be selected by one skilled in the art without undue experimentation.

In some embodiments the antibodies are monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a cancer-associated polypeptide, or fragment thereof or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Monoclonal antibody technology is used in implementing research, diagnosis and therapy. Monoclonal antibodies are used in radioimmunoassays, enzyme-linked immunosorbent assays, immunocytopathology, and flow cytometry for in vitro diagnosis, and in vivo for diagnosis and immunotherapy of human disease. Waldmann, T. A. (1991) Science 252:1657-1662. In particular, monoclonal antibodies have been widely applied to the diagnosis and therapy of cancer, wherein it is desirable to target malignant lesions while avoiding normal tissue. See, e.g., U.S. Pat. Nos. 4,753,894 to Frankel, et al.; 4,938,948 to Ring et al.; and 4,956,453 to Bjorn et al.

The monoclonal antibodies to SEMA4D may be used in a method of diagnosis of in breast, colon, lymphoid, ovary, pancreas, prostate, and kidney cancer either alone, or in conjunction with a method for the detection of other cancer associated markers.

The antibodies may be bispecific antibodies. In some embodiments, one of the binding specificities is for a cancer-associated polypeptide, or a fragment thereof, the other one is for any other antigen, and preferably for a cell-surface protein or receptor or receptor subunit, preferably one that is tumor specific. In some embodiments one of the binding specificities is for SEMA4D a protease domain of SEMA4D.

In some embodiments, the antibodies to cancer-associated polypeptides are capable of reducing or eliminating the biological function of cancer-associated polypeptides, as is described below. That is, the addition of anti-cancer-associated polypeptide antibodies (either polyclonal or preferably monoclonal) to cancer-associated polypeptides (or cells containing cancer-associated polypeptides) may reduce or eliminate the cancer-associated polypeptide activity. In some embodiments the antibodies of the present invention cause a decrease in activity of at least 25%, at least about 50%, or at least about 95-100%.

In some embodiments the antibodies to SEMA4D polypeptides are humanized antibodies. "Humanized" antibodies refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Alternatively, a humanized antibody may be derived from a chimeric antibody that retains or substantially retains the antigen-binding properties of the parental, non-human, antibody but which exhibits diminished immunogenicity as compared to the parental antibody when administered to humans. The phrase "chimeric antibody," as used herein, refers to an antibody containing sequence derived from two different antibodies (see, e.g., U.S. Pat. No. 4,816,567) that typically originate from different species. Typically, in these chimeric antibodies, the variable region of both light and heavy chains mimics the variable regions of antibodies derived from one species of mammals, while the constant portions are homologous to the sequences in antibodies derived from another. Most typically, chimeric antibodies comprise human and murine antibody fragments, generally human constant and mouse variable regions. Humanized antibodies are made by replacing the complementarity determining regions (CDRs) of a human antibody (acceptor antibody) with those from a non-human antibody (donor antibody) such as mouse, rat or rabbit having the desired specificity, affinity and capacity. In some instances, Fv framework residues of the human "acceptor" antibody are replaced by corresponding non-human residues from the "donor" antibody. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework residues (FR) regions are those of a human immunoglobulin consensus sequence. The humanized antibody optimally also will comprise at least a portion of an immunoglobulin constant region (Fc), typically that of a human immunoglobulin (Jones et al., Nature, 321: 522-525 (1986); Riechmann et al., Nature, 332:323-329 (1988); and Presta, Curr. Op. Struct. Biol., 2:593-596 (1992)). One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

Because humanized antibodies are less immunogenic in humans than the parental mouse monoclonal antibodies, they can be used for the treatment of humans with far less risk of anaphylaxis. Thus, these antibodies may be preferred in therapeutic applications that involve in vivo administration to a human such as, e.g., use as radiation sensitizers for the treatment of neoplastic disease or use in methods to reduce the side effects of, e.g., cancer therapy. Methods for humanizing non-human antibodies are well known in the art. Generally, a humanized antibody has one or more amino acid residues introduced into it from a source that is non-human. These non-human amino acid residues are often referred to as import residues, which are typically taken from an import variable domain. Humanization can be essentially performed following the method of Winter and co-workers (Jones et al., Nature 321:522-525 (1986); Riechmann et al., Nature 332: 323-327 (1988); Verhoeyen et al., Science 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349: 293-299; Lobuglio et al. (1989) Proc. Nat. Acad. Sci. USA 86:4220-4224; Shaw et al. (1987) J Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992).

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)). Humanized antibodies may be achieved by a variety of methods including, for example: (1) grafting the non-human complementarity determining regions (CDRs) onto a human framework and constant region (a process referred to in the art as "humanizing"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. Similarly, human antibodies can be made by introducing human immunoglobulin loci into transgenic animals, e.g., nice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); Jones et al., Nature 321:522-525 (1986); Morrison et al., Proc. Natl. Acad. Sci, U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31(3):169-217 (1994); and Kettleborough, C. A. et al., Protein Eng. 4(7): 773-83 (1991) each of which is incorporated herein by reference. Antibodies of the present invention can also be produced using human engineering techniques as discussed in U.S. Pat. No. 5,766,886, which is incorporated herein by reference.

The phrase "complementarity determining region" refers to amino acid sequences which together define the binding affinity and specificity of the natural Fv region of a native immunoglobulin binding site. See, e.g., Chothia et al., J. Mol. Biol. 196:901-917 (1987); Kabat et al., U.S. Dept. of Health and Human Services NIH Publication No. 91-3242 (1991). The phrase "constant region" refers to the portion of the antibody molecule that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu. One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region that disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors. See, e.g., U.S. Pat. Nos. 5,530,101 and 5,585,089 which are incorporated herein by reference.

Humanized antibodies to cancer-associated polypeptides can also be produced using transgenic animals that are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody-producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein.

In some embodiments, SEMA4D polypeptides as recited above and variants thereof may be used to immunize a transgenic animal as described above. Monoclonal antibodies are made using methods known in the art, and the specificity of the antibodies is tested using isolated cancer-associated polypeptides. Methods for preparation of the human or primate cancer-associated or an epitope thereof include, but are not limited to chemical synthesis, recombinant DNA techniques or isolation from biological samples. Chemical synthesis of a peptide can be performed, for example, by the classical Merrifeld method of solid phase peptide synthesis (Merrifeld, J. Am. Chem. Soc. 85:2149, 1963 which is incorporated by reference) or the FMOC strategy on a Rapid Automated Multiple Peptide Synthesis system (E. I. du Pont de Nemours Company, Wilmington, Del.) (Caprino and Han, J. Org. Chem. 37:3404, 1972 which is incorporated by reference).

Polyclonal antibodies can be prepared by immunizing rabbits or other animals by injecting antigen followed by subsequent boosts at appropriate intervals. Alternative animals include mice, rats, chickens, guinea pigs, sheep, horses, monkeys, camels and sharks. The animals are bled and sera assayed against purified cancer-associated proteins usually by ELISA or by bioassay based upon the ability to block the action of cancer-associated proteins. When using avian species, e.g., chicken, turkey and the like, the antibody can be isolated from the yolk of the egg. Monoclonal antibodies can be prepared after the method of Milstein and Kohler by fusing splenocytes from immunized mice with continuously replicating tumor cells such as myeloma or lymphoma cells. (Milstein and Kohler, Nature 256:495-497, 1975; Gulfre and Milstein, Methods in Enzymology: Immunochemical Techniques 73:1-46, Langone and Banatis eds., Academic Press, 1981 which are incorporated by reference). The hybridoma cells so formed are then cloned by limiting dilution methods and supernates assayed for antibody production by ELISA, RIA or bioassay.

The unique ability of antibodies to recognize and specifically bind to target proteins provides an approach for treating an overexpression of the protein. Thus, in some embodiments the present invention provides methods for preventing or treating diseases involving overexpression of a cancer-associated polypeptide by treatment of a patient with specific antibodies to the cancer-associated protein.

Specific antibodies, either polyclonal or monoclonal, to the cancer-associated proteins can be produced by any suitable method known in the art as discussed above. For example, murine or human monoclonal antibodies can be produced by hybridoma technology or, alternatively, the cancer-associated proteins, or an immunologically active fragment thereof, or an anti-idiotypic antibody, or fragment thereof can be administered to an animal to elicit the production of antibodies capable of recognizing and binding to the cancer-associated proteins. Such antibodies can be from any class of antibodies including, but not limited to IgG, IgA, IgM, IgD, and IgE or in the case of avian species, IgY and from any subclass of antibodies.

In some embodiments the antibodies of the present invention are neutralizing antibodies. In some embodiments the antibodies are targeting antibodies. In some embodiments, the antibodies are internalized upon binding a target. In some embodiments the antibodies do not become internalized upon binding a target and instead remain on the surface.

The antibodies of the present invention can be screened for the ability to either be rapidly internalized upon binding to the tumor-cell antigen in question, or for the ability to remain on the cell surface following binding. In some embodiments, for example in the construction of some types of immunoconjugates, the ability of an antibody to be internalized may be desired if internalization is required to release the toxin moiety. Alternatively, if the antibody is being used to promote ADCC or CDC, it may be more desirable for the antibody to remain on the cell surface. A screening method can be used to differentiate these type behaviors. For example, a tumor cell antigen bearing cell may be used where the cells are incubated with human IgG1 (control antibody) or one of the antibodies of the invention at a concentration of approximately 1 µg/mL on ice (with 0.1% sodium azide to block internalization) or 37° C. (without sodium azide) for 3 hours. The cells are then washed with cold staining buffer (PBS+1% BSA+0.1% sodium azide), and are stained with goat anti-human IgG-FITC for 30 minutes on ice. Geometric mean fluorescent intensity (MFI) is recorded by FACS Calibur. If no difference in MFI is observed between cells incubated with the antibody of the invention on ice in the presence of sodium azide and cells observed at 37° C. in the absence of sodium azide, the antibody will be suspected to be one that remains bound to the cell surface, rather than being internalized. If however, a decrease in surface stainable antibody is found when the cells are incubated at 37° C. in the absence of sodium azide, the antibody will be suspected to be one which is capable of internalization.

Antibody Conjugates

In some embodiments, the antibodies of the invention are conjugated. In some embodiments, the conjugated antibodies are useful for cancer therapeutics, cancer diagnosis, or imaging of cancerous cells.

For diagnostic applications, the antibody typically will be labeled with a detectable moiety. Numerous labels are available which can be generally grouped into the following categories:

(a) Radionuclides such as those discussed infra. The antibody can be labeled, for example, with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

The antibodies may also be used for in vivo diagnostic assays. In some embodiments, the antibody is labeled with a radionuclide so that the tumor can be localized using immunoscintiography. As a matter of convenience, the antibodies of the present invention can be provided in a kit, i.e., a packaged combination of reagents in predetermined amounts with instructions for performing the diagnostic assay. Where the antibody is labeled with an enzyme, the kit may include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

In some embodiments, antibodies are conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. Cancer Research 52: 127-131 (1992)) to generate a maytansinoid-antibody immunoconjugate. In some embodiments, the conjugate may be the highly potent maytansine derivative DM1 (N2'-deacetyl-N2'-(3-mercapto-1-oxopropyl)-maytansine) (see for example WO02/098883 published Dec. 12, 2002) which has an IC50 of approximately 10-11 M (review, see Payne (2003) Cancer Cell 3:207-212) or DM4 (N2'-deacetyl-N2'(4-methyl-4-mercapto-1-oxopentyl)-maytansine) (see for example WO2004/103272 published Dec. 2, 2004).

In some embodiments the antibody conjugate comprises an anti-tumor cell antigen antibody conjugated to one or more calicheamicin molecules. The calicheamicin family of antibiotics is capable of producing double-stranded DNA breaks at sub-picomolar concentrations. Structural analogues of calicheamicin which may be used include, but are not limited to, gamma₁I, alpha₂I, alpha₃I, N-acetyl-gamma₁I, PSAG and thetaI₁ (Hinman et al. Cancer Research 53: 3336-3342 (1993) and Lode et al. Cancer Research 58: 2925-2928 (1998)). See, also, U.S. Pat. Nos. 5,714,586; 5,712,374; 5,264,586; and 5,773,001, each of which is expressly incorporated herein by reference.

In some embodiments the antibody is conjugated to a prodrug capable of being release in its active form by enzymes overproduced in many cancers. For example, antibody conjugates can be made with a prodrug form of doxorubicin wherein the active component is released from the conjugate by plasmin. Plasmin is known to be over produced in many cancerous tissues (see Decy et al, (2004) FASEB Journal 18(3): 565-567).

In some embodiments the antibodies are conjugated to enzymatically active toxins and fragments thereof. In some embodiments the toxins include, without limitation, diphtheria A chain, nonbinding active fragments of diphtheria toxin, exotoxin A chain (from *Pseudomonas aeruginosa*), Pseudomonas endotoxin, ricin A chain, abrin A chain, modeccin A chain, alpha-sarcin, *Aleurites fordii* proteins, dianthin proteins, *Phytolaca americana* proteins (PAPI, PAPII, and PAP-S), Ribonuclease (Rnase), Deoxyribonuclease (Dnase), pokeweed antiviral protein, *momordica charantia* inhibitor, curcin, crotin, *sapaonaria officinalis* inhibitor, gelonin, mitogellin, restrictocin, phenomycin, neomycin and the tricothecenes. See, for example, WO 93/21232 published Oct. 28, 1993. In some embodiments the toxins have low intrinsic immunogenicity and a mechanism of action (e.g. a cytotoxic mechanism versus a cytostatic mechanism) that reduces the opportunity for the cancerous cells to become resistant to the toxin.

In some embodiments conjugates made between the antibodies of the invention and immunomodulators. For example, in some embodiments immunostimulatory oligonucleotides can be used. These molecules are potent immunogens that can elicit antigen-specific antibody responses (see Datta et al, (2003) Ann N.Y. Acad. Sci. 1002: 105-111). Additional immunomodulatory compounds can include stem cell growth factor such as "S1 factor", lymphotoxins such as tumor necrosis factor (TNF), hematopoietic factor such as an interleukin, colony stimulating factor (CSF) such as granulocyte-colony stimulating factor (G-CSF) or granulocyte macrophage-stimulating factor (GM-CSF), interferon (IFN) such as interferon alpha, beta or gamma, erythropoietin, and thrombopoietin.

In some embodiments radioconjugated antibodies are provided. In some embodiments such antibodies can be made using P-32, P-33, Sc-47, Fe-59, Cu-64, Cu-67, Se-75, As-77, Sr-89, Y-90, Mo-99, Rh-105, Pd-109, Ag—I11, I-125, I-131, Pr-142, Pr-143, Pm-149, Sm-153, Th-161, Ho-166, Er-169, Lu-177, Re-186, Re-188, Re-189, Ir-194, Au-198, Au-199, Pb-211, Pb-212, and Bi-213, Co-58, Ga-67, Br-80m, Tc-99m, Rh-103m, Pt-109, In-i11, Sb-1 19, 1-125, Ho-161, Os-189m, Ir-192, Dy-152, At-211, Bi-212, Ra-223, Rn-219, Po-215, Bi-211, Ac-225, Fr-221, At-217, Bi-213, Fm-255 and combinations and subcombinations thereof. In some embodiments, boron, gadolinium or uranium atoms are conjugated to the antibodies. In some embodiments the boron atom is B-10, the gadolinium atom is Gd-157 and the uranium atom is U-235.

In some embodiments the radionuclide conjugate has a radionuclide with an energy between 20 and 10,000 keV. The radionuclide can be an Auger emitter, with an energy of less than 1000 keV, a P emitter with an energy between 20 and 5000 keV, or an alpha or 'a' emitter with an energy between 2000 and 10,000 keV.

In some embodiments diagnostic radioconjugates are provided which comprise a radionuclide that is a gamma-beta- or positron-emitting isotope. In some embodiments the radionuclide has an energy between 20 and 10,000 keV. In some embodiments the radionuclide is selected from the group of $^{18}$F, $^{5I}$Mn, $^{52m}$Mn, $^{52}$Fe, $^{55}$Co, $^{62}$Cu, $^{64}$Cu, $^{68}$Ga, $^{72}$As, $^{75}$Br, $^{76}$Br, $^{82m}$Rb, $^{83}$Sr, $^{86}$y, $^{89}$Zr, $^{94m}$Tc, $^{51}$Cr, $^{57}$Co, $^{58}$Co, $^{59}$Fe, $^{67}$CU, $^{67}$Ga, $^{75}$Se, $^{97}$Ru, $^{99m}$Tc, $^{114m}$In, $^{123}$I, $^{125}$I, $^{13}$Li and $^{197}$Hg.

In some embodiments the antibodies of the invention are conjugated to diagnostic agents that are photoactive or contrast agents. Photoactive compounds can comprise compounds such as chromogens or dyes. Contrast agents may be, for example a paramagnetic ion, wherein the ion comprises a metal selected from the group of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III). The contrast agent may also be a radio-opaque compound used in X-ray techniques or computed tomography, such as an iodine, iridium, barium, gallium and thallium compound. Radio-opaque compounds may be selected from the group of barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride. In some embodiments, the diagnostic immunoconjugates may contain ultrasound-enhancing agents such as a gas filled liposome that is conjugated to an antibody of the invention. Diagnostic immunoconjugates may be used for a variety of procedures including, but not limited to, intraoperative, endoscopic or intravascular methods of tumor or cancer diagnosis and detection.

In some embodiments antibody conjugates are made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. Cancer Research 52: 127-131 (1992)) may be used. Agents may be additionally be linked to the antibodies of the invention through a carbohydrate moiety.

In some embodiments fusion proteins comprising the antibodies of the invention and cytotoxic agents may be made, e.g. by recombinant techniques or peptide synthesis. In some embodiments such immunoconjugates comprising the anti-tumor antigen antibody conjugated with a cytotoxic agent are administered to the patient. In some embodiments the immunoconjugate and/or tumor cell antigen protein to which it is bound is/are internalized by the cell, resulting in increased therapeutic efficacy of the immunoconjugate in killing the cancer cell to which it binds. In some embodiments, the cytotoxic agent targets or interferes with nucleic acid in the cancer cell. Examples of such cytotoxic agents include maytansinoids, calicheamicins, ribonucleases and DNA endonucleases.

In some embodiments the antibodies are conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

In some embodiments the antibodies are conjugated conjugated to a cytotoxic molecule which is released inside a target cell lysosome. For example, the drug monomethyl auristatin E (MMAE) can be conjugated via a valine-citrulline linkage which will be cleaved by the proteolytic lysozymal enzyme cathepsin B following internalization of the antibody conjugate (see for example WO03/026577 published Apr. 3, 2003). In some embodiments, the MMAE can be attached to the antibody using an acid-labile linker containing a hydrazone functionality as the cleavable moiety (see for example WO02/088172 published Nov. 11, 2002).

Antibody Dependent Enzyme Mediated Prodrug Therapy (ADEPT)

In some embodiments the antibodies of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

In some embodiments the enzyme component of the immunoconjugate useful for ADEPT includes any enzyme capable of acting on a prodrug in such a way so as to covert it into its more active, cytotoxic form.

Enzymes that are useful in ADEPT include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as .beta.-galactosidase and neuraminidase useful for converting glycosylated prodrugs into free drugs; .beta.-lactamase useful for converting drugs derivatized with .beta.-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. In some embodiments antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population.

In some embodiments the ADEPT enzymes can be covalently bound to the antibodies by techniques well known in the art such as the use of the heterobifunctional crosslinking reagents discussed above. In some embodiments, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

In some embodiments identification of an antibody that acts in a cytostatic manner rather than a cytotoxic manner can be accomplished by measuring viability of a treated target cell culture in comparison with a non-treated control culture. Viability can be detected using methods known in the art such as the CellTiter-Blue® Cell Viability Assay or the CellTiter-Glo® Luminescent Cell Viability Assay (Promega, catalog numbers G8080 and G5750 respectively). In some embodiments an antibody is considered as potentially cytostatic if treatment causes a decrease in cell number in comparison to the control culture without any evidence of cell death as measured by the means described above.

In some embodiments an in vitro screening assay can be performed to identify an antibody that promotes ADCC using assays known in the art. One exemplary assay is the In Vitro ADCC Assay. To prepare chromium 51-labeled target cells, tumor cell lines are grown in tissue culture plates and harvested using sterile 10 mM EDTA in PBS. The detached cells are washed twice with cell culture medium. Cells ($5 \times 10^6$) are labeled with 200 µCi of chromium 51 (New England Nuclear/DuPont) at 37° C. for one hour with occasional mixing. Labeled cells were washed three times with cell culture medium, then are resuspended to a concentration of $1 \times 10^5$ cells/mL. Cells are used either without opsonization, or are opsonized prior to the assay by incubation with test antibody at 100 ng/mL and 1.25 ng/mL in PBMC assay or 20 ng/mL and 1 ng/mL in NK assay. Peripheral blood mononuclear cells are prepared by collecting blood on heparin from normal healthy donors and diluted with an equal volume of phosphate buffered saline (PBS). The blood is then layered over LYMPHOCYTE SEPARATION MEDIUM® (LSM: Organon Teknika) and centrifuged according to the manufacturer's instructions. Mononuclear cells are collected from the LSM-plasma interface and are washed three times with PBS. Effector cells are suspended in cell culture medium to a final concentration of $1 \times 10^7$ cells/mL. After purification through LSM, natural killer (NK) cells are isolated from PBMCs by negative selection using an NK cell isolation kit and a magnetic column (Miltenyi Biotech) according to the manufacturer's instructions. Isolated NK cells are collected, washed and resuspended in cell culture medium to a concentration of $2 \times 10^6$ cells/mL. The identity of the NK cells is confirmed by flow cytometric analysis. Varying effector:target ratios are prepared by serially diluting the effector (either PBMC or NK) cells two-fold along the rows of a microtiter plate (100 µL final volume) in cell culture medium. The concentration of effector cells ranges from $1.0 \times 10^7$/mL to $2.0 \times 14$/mL for PBMC and from $2.0 \times 10^6$/mL to $3.9 \times 10^3$/mL for NK. After titration of effector cells, 100 µL of chromium 51-labeled target cells (opsonized or nonoponsonized) at $1 \times 10^5$ cells/mL are added to each well of the plate. This results in an initial effector:target ratio of 100:1 for PBMC and 20:1 for NK cells. All assays are run in duplicate, and each plate contains controls for both spontaneous lysis (no effector cells) and total lysis (target cells plus 100 µL 1% sodium dodecyl sulfate, 1 N sodium hydroxide). The plates are incubated at 37° C. for 18 hours, after which the cell culture supernatants are harvested using a supernatant collection system (Skatron Instrument, Inc.) and counted in a Minaxi auto-gamma 5000 series gamma counter (Packard) for one minute. Results are then expressed as percent cytotoxicity using the formula: % Cytotoxicity=(sample cpm-spontaneous lysis)/(total lysis-spontaneous lysis)×100.

To identify an antibody that promotes CDC, the skilled artisan may perform an assay known in the art. One exemplary assay is the In Vitro CDC assay. In vitro, CDC activity can be measured by incubating tumor cell antigen expressing cells with human (or alternate source) complement-containing serum in the absence or presence of different concentrations of test antibody. Cytotoxicity is then measured by quantifying live cells using ALAMAR BLUE® (Gazzano-Santoro et al., J. Immunol. Methods 202 163-171 (1997)). Control assays are performed without antibody, and with antibody, but using heat inactivated serum and/or using cells which do not express the tumor cell antigen in question. Alternatively, red blood cells can be coated with tumor antigen or peptides derived from tumor antigen, and then CDC may be assayed by observing red cell lysis (see for example Karjalainen and Mantyjarvi, Acta Pathol Microbiol Scand [C]. 1981 October; 89(5):315-9).

To select for antibodies that induce cell death, loss of membrane integrity as indicated by, e.g., PI, trypan blue or 7AAD uptake may be assessed relative to control. One exemplary assay is the PI uptake assay using tumor antigen expressing cells. According to this assay, tumor cell antigen expressing cells are cultured in Dulbecco's Modified Eagle Medium (D-MEM):Ham's F-12 (50:50) supplemented with 10% heat-inactivated FBS (Hyclone) and 2 mM L-glutamine. (Thus, the assay is performed in the absence of complement and immune effector cells). The tumor cells are seeded at a density of 3×10⁶ per dish in 100×20 mm dishes and allowed to attach overnight. The medium is then removed and replaced with fresh medium alone or medium containing 10 μg/mL of the appropriate monoclonal antibody. The cells are incubated for a 3 day time period. Following each treatment, monolayers are washed with PBS and detached by trypsinization. Cells are then centrifuged at 1200 rpm for 5 minutes at 4° C., the pellet resuspended in 3 mL ice cold $Ca^{2+}$ binding buffer (10 mM Hepes, pH 7.4, 140 mM NaCl, 2.5 mM $CaCl_2$) and aliquoted into 35 mm strainer-capped 12×75 tubes (1 mL per tube, 3 tubes per treatment group) for removal of cell clumps. Tubes then receive PI (10 μg/mL). Samples may be analyzed using a FACSCAN™ flow cytometer and FACSCONVERT™ CellQuest software (Becton Dickinson). Those antibodies that induce statistically significant levels of cell death as determined by PI uptake may be selected as cell death-inducing antibodies.

Antibodies can also be screened in vivo for apoptotic activity using $^{18}F$-annexin as a PET imaging agent. In this procedure, Annexin V is radiolabeled with $^{18}F$ and given to the test animal following dosage with the antibody under investigation. One of the earliest events to occur in the apoptotic process in the eversion of phosphatidylserine from the inner side of the cell membrane to the outer cell surface, where it is accessible to annexin. The animals are then subjected to PET imaging (see Yagle et al, J Nucl Med. 2005 April; 46(4):658-66). Animals can also be sacrificed and individual organs or tumors removed and analyzed for apoptotic markers following standard protocols.

While in some embodiments cancer may be characterized by overexpression of a gene expression product, the present application further provides methods for treating cancer which is not considered to be a tumor antigen-overexpressing cancer. To determine tumor antigen expression in the cancer, various diagnostic/prognostic assays are available. In some embodiments, gene expression product overexpression can be analyzed by IHC. Paraffin embedded tissue sections from a tumor biopsy may be subjected to the IHC assay and accorded a tumor antigen protein staining intensity criteria as follows:

Score 0: no staining is observed or membrane staining is observed in less than 10% of tumor cells.

Score 1+: a faint/barely perceptible membrane staining is detected in more than 10% of the tumor cells. The cells are only stained in part of their membrane.

Score 2+: a weak to moderate complete membrane staining is observed in more than 10% of the tumor cells.

Score 3+: a moderate to strong complete membrane staining is observed in more than 10% of the tumor cells.

Those tumors with 0 or 1+ scores for tumor antigen overexpression assessment may be characterized as not overexpressing the tumor antigen, whereas those tumors with 2+ or 3+ scores may be characterized as overexpressing the tumor antigen.

Alternatively, or additionally, FISH assays such as the INFORM™ (sold by Ventana, Ariz.) or PATHVISION™ (Vysis, Ill.) may be carried out on formalin-fixed, paraffin-embedded tumor tissue to determine the extent (if any) of tumor antigen overexpression in the tumor.

Additionally, antibodies can be chemically modified by covalent conjugation to a polymer to increase their circulating half-life, for example. Each antibody molecule may be attached to one or more (i.e. 1, 2, 3, 4, 5 or more) polymer molecules. Polymer molecules are preferably attached to antibodies by linker molecules. The polymer may, in general, be a synthetic or naturally occurring polymer, for example an optionally substituted straight or branched chain polyalkene, polyalkenylene or polyoxyalkylene polymer or a branched or unbranched polysaccharide, e.g. homo- or hetero-polysaccharide. In some embodiments the polymers are polyoxyethylene polyols and polyethylene glycol (PEG). PEG is soluble in water at room temperature and has the general formula: R(O—$CH_2$—$CH_2$)n O—R where R can be hydrogen, or a protective group such as an alkyl or alkanol group. In some embodiments, the protective group has between 1 and 8 carbons. In some embodiments the protective group is methyl. The symbol n is a positive integer, between 1 and 1,000, or 2 and 500. In some embodiments the PEG has an average molecular weight between 1000 and 40,000, between 2000 and 20,000, or between 3,000 and 12, 000. In some embodiments, PEG has at least one hydroxy group. In some embodiments the hydroxy is a terminal hydroxy group. In some embodiments it is this hydroxy group which is activated to react with a free amino group on the inhibitor. However, it will be understood that the type and amount of the reactive groups may be varied to achieve a covalently conjugated PEG/antibody of the present invention. Polymers, and methods to attach them to peptides, are shown in U.S. Pat. Nos. 4,766, 106; 4,179,337; 4,495,285; and 4,609,546 each of which is hereby incorporated by reference in its entirety.

Labelling and Detection

In some embodiments, the cancer-associated nucleic acids, proteins and antibodies of the invention are labeled. It is noted that many of the examples of conjugates discussed supra are also relevant to non-antibodies. To the extent such examples and relevant they are incorporated herein.

By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) coloured or fluorescent dyes. The labels may be incorporated into the cancer-associated nucleic acids, proteins and antibodies at any position. For example, the label should be capable of producing, either directly or indirectly, a detectable signal. The detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the label may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982).

Detection of the expression product of interest can be accomplished using any detection method known to those of skill in the art. "Detecting expression" or "detecting the level of" is intended to mean determining the quantity or presence of a biomarker protein or gene in the biological sample. Thus, "detecting expression" encompasses instances where a biomarker is determined not to be expressed, not to be detectably expressed, expressed at a low level, expressed at a normal level, or overexpressed. In some embodiments, in order to determine the effect of an anti-tumor cell antigen therapeutic, a test biological sample comprising tumor cell antigen-expressing neoplastic cells is contacted with the anti-tumor cell antigen therapeutic agent for a sufficient time to allow the therapeutic agent to exert a cellular response, and then expression level of one or more biomarkers of interest in that test biological sample is compared to the expression level in the control biological sample in the absence of the anti-tumor cell antigen therapeutic agent. In some embodiments, the control biological sample of neoplastic cells is contacted with a neutral substance or negative control. For example, in some embodiments, a non-specific immunoglobulin, for example IgG1, which does not bind to tumor cell antigen serves as the negative control. Detection can occur over a time course to allow for monitoring of changes in expression products over time. Detection can also occur with exposure to different concentrations of the anti-tumor cell antigen therapeutic agent to generate a "dose-response" curve for any given biomarker of interest.

Detection of Cancer Phenotype

Once expressed and, if necessary, purified, the cancer-associated proteins and nucleic acids are useful in a number of applications. In some embodiments, the expression levels of genes are determined for different cellular states in the cancer phenotype; that is, the expression levels of genes in normal tissue and in cancer tissue (and in some cases, for varying severities of lymphoma that relate to prognosis, as outlined below) are evaluated to provide expression profiles. An expression profile of a particular cell state or point of development is essentially a "fingerprint" of the state; while two states may have any particular gene similarly expressed, the evaluation of a number of genes simultaneously allows the generation of a gene expression profile that is unique to the state of the cell. By comparing expression profiles of cells in different states, information regarding which genes are important (including both up- and down-regulation of genes) in each of these states is obtained. Then, diagnosis may be done or confirmed: does tissue from a particular patient have the gene expression profile of normal or cancer tissue.

"Differential expression," or equivalents used herein, refers to both qualitative as well as quantitative differences in the temporal and/or cellular expression patterns of genes, within and among the cells. Thus, a differentially expressed gene can qualitatively have its expression altered, including an activation or inactivation, in, for example, normal versus cancer tissue. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either up-regulated, resulting in an increased amount of transcript, or down-regulated, resulting in a decreased amount of transcript. The degree to which expression differs need only be large enough to quantify via standard characterization techniques as outlined below, such as by use of Affymetrix GeneChip® expression arrays, Lockhart, Nature Biotechnology, 14:1675-1680 (1996), hereby expressly incorporated by reference. Other techniques include, but are not limited to, quantitative reverse transcriptase PCR, Northern analysis and RNase protection. As outlined above, the change in expression (i.e. upregulation or downregulation) is at least about 2-fold, 3-fold, 5-fold, 10-fold, 20-fold, 50-fold, or even 100 fold or more.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the cancer-associated protein and standard immunoassays (ELISAs, etc.) or other techniques, including mass spectroscopy assays, 2D gel electrophoresis assays, etc. Thus, the proteins corresponding to cancer-associated genes, i.e. those identified as being important in a particular cancer phenotype, i.e., lymphoma, can be evaluated in a diagnostic test specific for that cancer.

In some embodiments, gene expression monitoring is performed and a number of genes are monitored simultaneously. However, multiple protein expression monitoring can be done as well to prepare an expression profile. Alternatively, these assays may be done on an individual basis.

In some embodiments, the cancer-associated nucleic acid probes may be attached to biochips as outlined herein for the detection and quantification of cancer-associated sequences in a particular cell. The assays are done as is known in the art. As will be appreciated by those in the art, any number of different cancer-associated sequences may be used as probes, with single sequence assays being used in some cases, and a plurality of the sequences described herein being used in other embodiments. In addition, while solid-phase assays are described, any number of solution based assays may be done as well.

In some embodiments, both solid and solution based assays may be used to detect cancer-associated sequences that are up-regulated or down-regulated in cancers as compared to normal tissue. In instances where the cancer-associated sequence has been altered but shows the same expression profile or an altered expression profile, the protein will be detected as outlined herein.

In some embodiments nucleic acids encoding the cancer-associated protein are detected. Although DNA or RNA encoding the cancer-associated protein may be detected, of particular interest are methods wherein the mRNA encoding a cancer-associated protein is detected. The presence of mRNA in a sample is an indication that the cancer-associated gene has been transcribed to form the mRNA, and suggests that the protein is expressed. Probes to detect the mRNA can be any nucleotide/deoxynucleotide probe that is complementary to and base pairs with the mRNA and includes but is not limited to oligonucleotides, cDNA or RNA. Probes also should contain a detectable label, as defined herein. In one method the mRNA is detected after immobilizing the nucleic acid to be examined on a solid support such as nylon membranes and hybridizing the probe with the sample. Following washing to remove the non-specifically bound probe, the label is detected. In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding a cancer-associated protein is detected by binding the digoxygenin with an anti-digoxygenin secondary antibody and developed with nitro blue tetrazolium and 5-bromo-4-chloro-3-indoyl phosphate.

Any of the three classes of proteins as described herein (secreted, transmembrane or intracellular proteins) may be used in diagnostic assays. The cancer-associated proteins, antibodies, nucleic acids, modified proteins and cells containing cancer-associated sequences are used in diagnostic assays. This can be done on an individual gene or corresponding polypeptide level, or as sets of assays.

As described and defined herein, cancer-associated proteins find use as markers of cancers, including leukemia, breast cancer, colon cancer, kidney cancer, liver cancer, lung cancer, ovary cancer, pancreatic cancer, prostate cancer, uterine cancer, cervical cancer, skin cancer and lymphomas such as, but not limited to, Hodgkin's and non-Hodgkin's lymphoma. Detection of these proteins in putative cancer tissue or patients allows for a determination or diagnosis of the type of cancer. Numerous methods known to those of ordinary skill in the art find use in detecting cancers.

Antibodies may be used to detect cancer-associated proteins. One method separates proteins from a sample or patient by electrophoresis on a gel (typically a denaturing and reducing protein gel, but may be any other type of gel including isoelectric focusing gels and the like). Following separation of proteins, the cancer-associated protein is detected by immunoblotting with antibodies raised against the cancer-associated protein. Methods of immunoblotting are well known to those of ordinary skill in the art. The antibodies used in such methods may be labeled as described above.

In some methods, antibodies to the SEMA4D protein find use in situ imaging techniques. In this method cells are contacted with from one to many antibodies to the cancer-associated protein(s). Following washing to remove non-specific antibody binding, the presence of the antibody or antibodies is detected. In some embodiments the antibody is detected by incubating with a secondary antibody that contains a detectable label. In another method the primary antibody to the cancer-associated protein(s) contains a detectable label. In another method, each one of multiple primary antibodies contains a distinct and detectable label. This method finds particular use in simultaneous screening for a plurality of cancer-associated proteins. As will be appreciated by one of ordinary skill in the art, numerous other histological imaging techniques are useful in the invention.

The label may be detected in a fluorometer that has the ability to detect and distinguish emissions of different wavelengths. In addition, a fluorescence activated cell sorter (FACS) can be used in the method.

Antibodies may be used in diagnosing cancers from blood samples. As previously described, certain cancer-associated proteins are secreted/circulating molecules. Blood samples, therefore, are useful as samples to be probed or tested for the presence of secreted cancer-associated proteins. Antibodies can be used to detect the cancer-associated proteins by any of the previously described immunoassay techniques including ELISA, immunoblotting (Western blotting), immunoprecipitation, BIACORE technology and the like, as will be appreciated by one of ordinary skill in the art.

In situ hybridization of labeled cancer-associated nucleic acid probes to tissue arrays may be carried out. For example, arrays of tissue samples, including cancer-associated tissue and/or normal tissue, are made. In situ hybridization as is known in the art can then be done.

It is understood that when comparing the expression fingerprints between an individual and a standard, the skilled artisan can make a diagnosis as well as a prognosis. It is further understood that the genes that indicate diagnosis may differ from those that indicate prognosis.

As noted above, the cancer-associated proteins, antibodies, nucleic acids, modified proteins and cells containing cancer-associated sequences can be used in prognosis assays. As above, gene expression profiles can be generated that correlate to cancer severity, in terms of long term prognosis. Again, this may be done on either a protein or gene level. As above, the cancer-associated probes may be attached to biochips for the detection and quantification of cancer-associated sequences in a tissue or patient. The assays proceed as outlined for diagnosis.

Screening Assays

Any of the cancer-associated gene sequences as described herein may be used in drug screening assays. The cancer-associated proteins, antibodies, nucleic acids, modified proteins and cells containing cancer-associated gene sequences are used in drug screening assays or by evaluating the effect of drug candidates on a "gene expression profile" or expression profile of polypeptides. In one method, the expression profiles are used, preferably in conjunction with high throughput screening techniques to allow monitoring for expression profile genes after treatment with a candidate agent, Zlokarnik, et al., Science 279, 84-8 (1998), Heid, et al., Genome Res., 6:986-994 (1996).

In some embodiments, the cancer associated proteins, antibodies, nucleic acids, modified proteins and cells containing the native or modified cancer associated proteins are used in screening assays. That is, the present invention provides novel methods for screening for compositions that modulate the cancer phenotype. As above, this can be done by screening for modulators of gene expression or for modulators of protein activity. Similarly, this may be done on an individual gene or protein level or by evaluating the effect of drug candidates on a "gene expression profile". In an embodiment some embodiments, the expression profiles are used, preferably sometimes in conjunction with high throughput screening techniques, to allow monitoring for expression profile genes after treatment with a candidate agent, see Zlokarnik, supra.

A variety of assays to evaluate the effects of agents on gene expression may be performed. In some embodiments, assays may be run on an individual gene or protein level. That is, candidate bioactive agents may be screened to modulate the gene's regulation. "Modulation" thus includes both an increase and a decrease in gene expression or activity. The amount of modulation will depend on the original change of the gene expression in normal versus tumor tissue, with changes of at least 10%, at least 50%, at least 100-300%, and at least 300-1000% or greater. Thus, if a gene exhibits a 4-fold increase in tumor compared to normal tissue, a decrease of about four fold may be desired; a 10-fold decrease in tumor compared to normal tissue gives a 10-fold increase in expression for a candidate agent is desired, etc. Alternatively, where the cancer-associated sequence has been altered but shows the same expression profile or an altered expression profile, the protein will be detected as outlined herein.

As will be appreciated by those in the art, this may be done by evaluation at either the gene or the protein level; that is, the amount of gene expression may be monitored using nucleic acid probes and the quantification of gene expression levels, or, alternatively, the level of the gene product itself can be monitored, for example through the use of antibodies to the cancer-associated protein and standard immunoassays. Alternatively, binding and bioactivity assays with the protein may be done as outlined below.

In some embodiments, a number of genes are monitored simultaneously, i.e. an expression profile is prepared, although multiple protein expression monitoring can be done as well.

In some embodiments, the cancer-associated nucleic acid probes are attached to biochips as outlined herein for the detection and quantification of cancer-associated sequences in a particular cell. The assays are further described below.

In some embodiments a candidate bioactive agent is added to the cells prior to analysis. Moreover, screens are provided to identify a candidate bioactive agent that modulates a particular type of cancer, modulates cancer-associated proteins, binds to a cancer-associated protein, or interferes between the binding of a cancer-associated protein and an antibody.

The term "candidate bioactive agent" or "drug candidate" or grammatical equivalents as used herein describes any molecule, e.g., protein, oligopeptide, small organic or inorganic molecule, polysaccharide, polynucleotide, etc., to be tested for bioactive agents that are capable of directly or indirectly altering either the cancer phenotype, binding to and/or modulating the bioactivity of a cancer-associated protein, or the expression of a cancer-associated sequence, including both nucleic acid sequences and protein sequences. In some embodiments, the candidate agent suppresses a cancer-associated phenotype, for example to a normal tissue fingerprint. Similarly, the candidate agent preferably suppresses a severe cancer-associated phenotype. Generally a plurality of assay mixtures are run in parallel with different agent concentrations to obtain a differential response to the various concentrations. Typically, one of these concentrations serves as a negative control, i.e., at zero concentration or below the level of detection.

In some embodiments a candidate agent will neutralize the effect of an SEMA4D protein. By "neutralize" is meant that activity of a protein is either inhibited or counter acted against so as to have substantially no effect on a cell and hence reduce the severity of cancer, or prevent the incidence of cancer.

Candidate agents encompass numerous chemical classes, though typically they are organic or inorganic molecules, preferably small organic compounds having a molecular weight of more than 100 and less than about 2,500 Daltons. In some embodiments small molecules are less than 2000, less than 1500, less than 1000, or less than 500 Da. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Other SEMA4D antagonists, such as small molecule antagonists, which are suitable for use in the methods of the present invention will be clear to the skilled person. In some embodiments the enhanced specificity of antibodies for a single Semaphorin family member makes antibodies an attractive option. Another consideration is that SEMA4D is expressed on the surface of cells and is therefore a promising candidate for targeting in this fashion.

Candidate agents are obtained from a wide variety of sources including libraries of synthetic or natural compounds. For example, numerous means are available for random and directed synthesis of a wide variety of organic compounds and biomolecules, including expression of randomized oligonucleotides. In some embodiments libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, or amidification to produce structural analogs.

In some embodiments, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In some embodiments, the amino acids are in the (S) or L-configuration. If non-naturally occurring side chains are used, non-amino acid substituents may be used, for example to prevent or retard in vivo degradations.

In some embodiments, the candidate bioactive agents are naturally occurring proteins or fragments of naturally occurring proteins. Thus, for example, cellular extracts containing proteins, or random or directed digests of proteinaceous cellular extracts, may be used. In this way libraries of prokaryotic and eukaryotic proteins may be made for screening in the methods of the invention. In some embodiments the libraries are of bacterial, fungal, viral, and mammalian proteins. In some embodiments the library is a human protein library.

In some embodiments, the candidate bioactive agents are peptides of from about 5 to about 30 amino acids, from about 5 to about 20 amino acids, or from about 7 to about 15 amino acids. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In some embodiments, the library is fully randomized, with no sequence preferences or constants at any position. In some embodiments, the library is biased. That is, some positions within the sequence are either held constant, or are selected from a limited number of possibilities. For example, in some embodiments, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In some embodiments, the candidate bioactive agents are nucleic acids. As described generally for proteins, nucleic acid candidate bioactive agents may be naturally occurring nucleic acids, random nucleic acids, or "biased" random nucleic acids. In another embodiment, the candidate bioactive agents are organic chemical moieties, a wide variety of which are available in the literature.

In assays for testing alteration of the expression profile of the SEMA4D gene, after the candidate agent has been added and the cells incubated for some period of time, a nucleic acid sample containing the target sequences to be analyzed is prepared. The target sequence is prepared using known techniques (e.g., converted from RNA to labeled cDNA, as described above) and added to a suitable microarray. For example, an in vitro reverse transcription with labels covalently attached to the nucleosides is performed. In some embodiments the nucleic acids are labeled with a label as defined herein, especially with biotin-FITC or PE, Cy3 and Cy5.

As will be appreciated by those in the art, these assays can be direct hybridization assays or can comprise "sandwich assays", which include the use of multiple probes, as is generally outlined in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. In some embodiments, the target nucleic acid is prepared as outlined above, and then added to the biochip comprising a plurality of nucleic acid probes, under conditions that allow the formation of a hybridization complex.

A variety of hybridization conditions may be used in the present invention, including high, moderate and low stringency conditions as outlined above. The assays are generally run under stringency conditions that allow formation of the label probe hybridization complex only in the presence of target. Stringency can be controlled by altering a step parameter that is a thermodynamic variable, including, but not limited to, temperature, formamide concentration, salt concentration, chaotropic salt concentration, pH, organic solvent concentration, etc. These parameters may also be used to control non-specific binding, as is generally outlined in U.S. Pat. No. 5,681,697. Thus, in some embodiments certain steps are performed at higher stringency conditions to reduce non-specific binding.

The reactions outlined herein may be accomplished in a variety of ways, as will be appreciated by those in the art. Components of the reaction may be added simultaneously, or sequentially, in any order, with suggested embodiments outlined below. In addition, the reaction may include a variety of other reagents in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target. In addition, either solid phase or solution based (i.e., kinetic PCR) assays may be used.

Once the assay is run, the data are analyzed to determine the expression levels, and changes in expression levels as between states, of individual genes, forming a gene expression profile.

In some embodiments, as for the diagnosis and prognosis applications, having identified SEMA4D as a differentially expressed gene, screens can be run to test for alteration of the expression of SEMA4D individually. That is, screening for modulation of regulation of expression of a single gene can be done. Thus, for example, in the case of target genes whose presence or absence is unique between two states, screening is done for modulators of the target gene expression.

In addition, screens can be done for novel genes that are induced in response to a candidate agent. After identifying a candidate agent based upon its ability to suppress a cancer-associated expression pattern leading to a normal expression pattern, or modulate a single cancer-associated gene expression profile so as to mimic the expression of the gene from normal tissue, a screen as described above can be performed to identify genes that are specifically modulated in response to the agent. Comparing expression profiles between normal tissue and agent treated cancer-associated tissue reveals genes that are not expressed in normal tissue or cancer-associated tissue, but are expressed in agent treated tissue. These agent specific sequences can be identified and used by any of the methods described herein for cancer-associated genes or proteins. In some embodiments these sequences and the proteins they encode find use in marking or identifying agent-treated cells. In addition, antibodies can be raised against the agent-induced proteins and used to target novel therapeutics to the treated cancer-associated tissue sample.

Thus, in some embodiments, a candidate agent is administered to a population of cancer-associated cells that thus have an associated cancer-associated expression profile. By "administration" or "contacting" herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (i.e. a peptide) may be put into a viral construct such as a retroviral construct and added to the cell, such that expression of the peptide agent is accomplished; see PCT US97/01019, hereby expressly incorporated by reference.

Once the candidate agent has been administered to the cells, the cells can be washed if desired and are allowed to incubate under preferably physiological conditions for some period of time. The cells are then harvested and a new gene expression profile is generated, as outlined herein.

Thus, for example, cancer-associated tissue may be screened for agents that reduce or suppress the cancer-associated phenotype. A change in at least one gene of the expression profile indicates that the agent has an effect on cancer-associated activity. By defining such a signature for the cancer-associated phenotype, screens for new drugs that alter the phenotype can be devised. With this approach, the drug target need not be known and need not be represented in the original expression screening platform, nor does the level of transcript for the target protein need to change.

In some embodiments, as outlined above, screens may be done on individual genes and gene expression products. That is, having identified a particular differentially expressed gene as important in a particular state, screening of modulators of either the expression of the gene or the gene product itself can be done. The cancer-associated protein may be a fragment, or alternatively, be the full-length protein to the fragment encoded by the cancer-associated genes recited above. In some embodiments, the sequences are sequence variants as further described above.

In some embodiments the cancer-associated protein is a fragment approximately 14 to 24 amino acids in length. In some embodiments the fragment is a soluble fragment. In some embodiments, the fragment includes a non-transmembrane region. In some embodiments, the fragment has an N-terminal Cys to aid in solubility. In some embodiments, the C-terminus of the fragment is kept as a free acid and the N-terminus is a free amine to aid in coupling, e.g., to a cysteine.

In some embodiments the cancer-associated proteins are conjugated to an immunogenic agent as discussed herein. In some embodiments the cancer-associated protein is conjugated to BSA.

In some embodiments, screening is done to alter the biological function of the expression product of SEMA4D. Again, having identified the importance of a gene in a particular state, screening for agents that bind and/or modulate the biological activity of the gene product can be run as is more fully outlined below.

In some embodiments, screens are designed to first find candidate agents that can bind to cancer-associated proteins, and then these agents may be used in assays that evaluate the ability of the candidate agent to modulate the cancer-associated protein activity and the cancer phenotype. Thus, as will be appreciated by those in the art, there are a number of different assays that may be run; binding assays and activity assays.

In some embodiments, binding assays are done. In general, purified or isolated gene product is used; that is, the gene products of one or more cancer-associated nucleic acids are made. In general, this is done as is known in the art. For example, antibodies are generated to the protein gene products, and standard immunoassays are run to determine the amount of protein present. In some embodiments, cells comprising the cancer-associated proteins can be used in the assays.

Thus, in some embodiments, the methods comprise combining a cancer-associated protein and a candidate bioactive agent, and determining the binding of the candidate agent to the cancer-associated protein. Some embodiments utilize the human or mouse cancer-associated protein, although other mammalian proteins may also be used, for example for the development of animal models of human disease. In some embodiments, as outlined herein, variant or derivative cancer-associated proteins may be used.

In some embodiments of the methods herein, the cancer-associated protein or the candidate agent is non-diffusably bound to an insoluble support having isolated sample receiving areas (e.g. a microtiter plate, an array, etc.). The insoluble support may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon®, etc. Microtiter plates and arrays are especially convenient because a large number of assays can be carried out simultaneously, using small amounts of reagents and samples.

The particular manner of binding of the composition is not crucial so long as it is compatible with the reagents and overall methods of the invention, maintains the activity of the composition and is nondiffusable. Some methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In some embodiments, the cancer-associated protein is bound to the support, and a candidate bioactive agent is added to the assay. In some embodiments, the candidate agent is bound to the support and the cancer-associated protein is added. Novel binding agents include specific antibodies, non-natural binding agents identified in screens of chemical libraries or peptide analogs. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the cancer-associated protein may be done in a number of ways. In some embodiments, the candidate bioactive agent is labeled, and binding determined directly. For example, this may be done by attaching all or a portion of the cancer-associated protein to a solid support, adding a labeled candidate agent (for example a fluorescent label), washing off excess reagent, and determining whether the label is present on the solid support. Various blocking and washing steps may be utilized as is known in the art.

In some embodiments, only one of the components is labeled. For example, the proteins (or proteinaceous candidate agents) may be labeled at tyrosine positions using 125I, or with fluorophores. Alternatively, more than one component may be labeled with different labels; using $^{125}$I for the proteins, for example, and a fluorophore for the candidate agents.

In some embodiments, the binding of the candidate bioactive agent is determined through the use of competitive binding assays. In some embodiments, the competitor is a binding moiety known to bind to the target molecule (i.e. cancer-associated protein), such as an antibody, peptide, binding partner, ligand, etc. Under certain circumstances, there may be competitive binding as between the bioactive agent and the binding moiety, with the binding moiety displacing the bioactive agent.

In some embodiments, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In some embodiments, the competitor is added first, followed by the candidate bioactive agent. Displacement of the competitor is an indication that the candidate bioactive agent is binding to the cancer-associated protein and thus is capable of binding to, and potentially modulating, the activity of the cancer-associated protein. In some embodiments, either component can be labeled. Thus, for example, if the competitor is labeled, the presence of label in the wash solution indicates displacement by the agent. In some embodiments, if the candidate bioactive agent is labeled, the presence of the label on the support indicates displacement.

In some embodiments, the candidate bioactive agent is added first, with incubation and washing, followed by the competitor. The absence of binding by the competitor may indicate that the bioactive agent is bound to the cancer-associated protein with a higher affinity. Thus, if the candidate bioactive agent is labeled, the presence of the label on the support, coupled with a lack of competitor binding, may indicate that the candidate agent is capable of binding to the cancer-associated protein.

In some embodiments, the methods comprise differential screening to identify bioactive agents that are capable of modulating the activity of the cancer-associated proteins. In this embodiment, the methods comprise combining a cancer-associated protein and a competitor in a first sample. A second sample comprises a candidate bioactive agent, a cancer-associated protein and a competitor. The binding of the competitor is determined for both samples, and a change, or difference in binding between the two samples indicates the presence of an agent capable of binding to the cancer-associated protein and potentially modulating its activity. That is, if the binding of the competitor is different in the second sample relative to the first sample, the agent is capable of binding to the cancer-associated protein.

In some embodiments utilizes differential screening to identify drug candidates that bind to the native cancer-associated protein, but cannot bind to modified cancer-associated proteins. The structure of the cancer-associated protein may be modeled, and used in rational drug design to synthesize agents that interact with that site. Drug candidates that affect cancer-associated bioactivity are also identified by screening drugs for the ability to either enhance or reduce the activity of the protein.

Positive controls and negative controls may be used in the assays. In some embodiments all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of cancer-associated proteins may also be done. In some embodiments, methods for screening for a bioactive agent capable of modulating the activity of cancer-associated proteins comprise adding a candidate bioactive agent to a sample of cancer-associated proteins, as above, and determining an alteration in the biological activity of cancer-associated proteins. "Modulating the activity of a cancer-associated protein" includes an increase in activity, a decrease in activity, or a change in the type or kind of activity present. Thus, in some embodiments, the candidate agent should both bind to cancer-associated proteins (although this may not be necessary), and alter its biological or biochemical activity as defined herein. The methods include both in vitro screening methods, as are generally outlined above, and in vivo screening of cells for alterations in the presence, distribution, activity or amount of cancer-associated proteins.

Thus, in some embodiments, the methods comprise combining a cancer-associated sample and a candidate bioactive agent, and evaluating the effect on cancer-associated activity. By "cancer-associated activity" or grammatical equivalents herein is meant one of the cancer-associated protein's biological activities, including, but not limited to, its role in tumorigenesis, including cell division, cell proliferation, tumor growth, cancer cell survival and transformation of cells. In some embodiments, cancer-associated activity includes activation of or by a protein encoded by a nucleic acid derived from a cancer-associated gene as identified above. An inhibitor of cancer-associated activity is the inhibitor of any one or more cancer-associated activities.

In some embodiments, the activity of the cancer-associated protein is increased; in some embodiments, the activity of the cancer-associated protein is decreased. Thus, bioactive agents are antagonists in some embodiments, and bioactive agents are agonists in some embodiments.

In some embodiments, the invention provides methods for screening for bioactive agents capable of modulating the activity of a cancer-associated protein. The methods comprise adding a candidate bioactive agent, as defined above, to a cell comprising cancer-associated proteins. Preferred cell types include almost any cell. The cells contain a recombinant nucleic acid that encodes a cancer-associated protein. In some embodiments, a library of candidate agents is tested on a plurality of cells.

In some embodiments, the assays are evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In some embodiments, the determinations are determined at different stages of the cell cycle process.

In this way, bioactive agents are identified. Compounds with pharmacological activity are able to enhance or interfere with the activity of the cancer-associated protein.

Diagnosis and Treatment of Cancer

Methods of inhibiting cancer cell division are provided by the invention. In some embodiments, methods of inhibiting tumor growth are provided. In some embodiments, methods of treating cells or individuals with cancer are provided.

The methods may comprise the administration of a cancer inhibitor. In some embodiments, the cancer inhibitor is an antisense molecule, a pharmaceutical composition, a therapeutic agent or small molecule, or a monoclonal, polyclonal, chimeric or humanized antibody. In some embodiments, a therapeutic agent is coupled with an antibody. In some embodiments the therapeutic agent is coupled with a monoclonal antibody.

Methods for detection or diagnosis of cancer cells in an individual are also provided. In some embodiments, the diagnostic/detection agent is a small molecule that preferentially binds to a cancer-associated protein according to the invention. In some embodiments, the diagnostic/detection agent is an antibody In some embodiments of the invention, animal models and transgenic animals are provided, which find use in generating animal models of cancers, particularly lymphoma, leukemia, breast cancer, colon cancer, kidney cancer, liver cancer, lung cancer, ovary cancer, pancreatic cancer, prostate cancer, uterine cancer, cervical cancer or skin cancer.

(a) Antisense Molecules

The cancer inhibitor used may be an antisense molecule. Antisense molecules as used herein include antisense or sense oligonucleotides comprising a single-stranded nucleic acid sequence (either RNA or DNA) capable of binding to target mRNA (sense) or DNA (antisense) sequences for cancer molecules. Antisense or sense oligonucleotides, according to the present invention, comprise a fragment generally of from about 14 to about 30 nucleotides. The ability to derive an antisense or a sense oligonucleotide, based upon a cDNA sequence encoding a given protein is described in, for example, Stein and Cohen, Cancer Res. 48:2659, (1988) and van der Krol et al., BioTechniques 6:958, (1988).

Antisense molecules can be modified or unmodified RNA, DNA, or mixed polymer oligonucleotides. These molecules function by specifically binding to matching sequences resulting in inhibition of peptide synthesis (Wu-Pong, November 1994, BioPharm, 20-33) either by steric blocking or by activating an RNase H enzyme. Antisense molecules can also alter protein synthesis by interfering with RNA processing or transport from the nucleus into the cytoplasm (Mukhopadhyay & Roth, 1996, Crit. Rev. in Oncogenesis 7, 151-190). In addition, binding of single stranded DNA to RNA can result in nuclease-mediated degradation of the heteroduplex (Wu-Pong, supra). Backbone modified DNA chemistry which have thus far been shown to act as substrates for RNase H are phosphorothioates, phosphorodithioates, borontrifluoridates, and 2'-arabino and 2'-fluoro arabino-containing oligonucleotides.

Antisense molecules may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. In some embodiments, a sense or an antisense oligonucleotide may be introduced into a cell containing the target nucleic acid sequence by formation of an oligonucleotide-lipid complex, as described in WO 90/10448. It is understood that the use of antisense molecules or knock out and knock in models may also be used in screening assays as discussed above, in addition to methods of treatment.

(b) RNA Interference

RNA interference refers to the process of sequence-specific post transcriptional gene silencing in animals mediated by short interfering RNAs (siRNA) (Fire et al., Nature, 391, 806 (1998)). The corresponding process in plants is referred to as post transcriptional gene silencing or RNA silencing and is also referred to as quelling in fungi. The presence of dsRNA in cells triggers the RNAi response though a mechanism that has yet to be fully characterized. This mechanism appears to be different from the interferon response that results from dsRNA mediated activation of protein kinase PKR and 2',5'-oligoadenylate synthetase resulting in non-specific cleavage of mRNA by ribonuclease L. (reviewed in Sharp, P.A., RNA interference—2001, Genes & Development 15:485-490 (2001)).

Small interfering RNAs (siRNAs) are powerful sequence-specific reagents designed to suppress the expression of genes in cultured mammalian cells through a process known as RNA interference (RNAi). Elbashir, S. M. et al. Nature 411: 494-498 (2001); Caplen, N. J. et al. Proc. Natl. Acad. Sci. USA 98:9742-9747 (2001); Harborth, J. et al. J. Cell Sci. 114:4557-4565 (2001). The term "short interfering RNA" or "siRNA" refers to a double stranded nucleic acid molecule capable of RNA interference "RNAi", (see Kreutzer et al., WO 00/44895; Zernicka-Goetz et al. WO 01/36646; Fire, WO 99/32619; Mello and Fire, WO 01/29058). As used herein, siRNA molecules are limited to RNA molecules but further encompasses chemically modified nucleotides and non-nucleotides. siRNA gene-targeting experiments have been carried out by transient siRNA transfer into cells (achieved by such classic methods as liposome-mediated transfection, electroporation, or microinjection).

Molecules of siRNA are 15- to 30-, 18- to 25-, or 21- to 23-nucleotide RNAs, with characteristic 2- to 3-nucleotide 3'-overhanging ends resembling the RNase III processing products of long double-stranded RNAs (dsRNAs) that normally initiate RNAi. When introduced into a cell, they assemble with yet-to-be-identified proteins of an endonuclease complex (RNA-induced silencing complex), which then guides target mRNA cleavage. As a consequence of degradation of the targeted mRNA, cells with a specific phenotype characteristic of suppression of the corresponding protein product are obtained. The small size of siRNAs, compared with traditional antisense molecules, prevents activation of the dsRNA-inducible interferon system present in mammalian cells. This avoids the nonspecific phenotypes normally produced by dsRNA larger than 30 base pairs in somatic cells.

Intracellular transcription of small RNA molecules is achieved by cloning the siRNA templates into RNA polymerase III (Pol III) transcription units, which normally encode the small nuclear RNA (snRNA) U6 or the human RNase P RNA H1. Two approaches have been developed for expressing siRNAs: in the first, sense and antisense strands constituting the siRNA duplex are transcribed by individual promoters (Lee, N. S. et al. Nat. Biotechnol. 20, 500-505 (2002); Miyagishi, M. & Taira, K. Nat. Biotechnol. 20, 497-500 (2002).); in the second, siRNAs are expressed as foldback stem-loop structures that give rise to siRNAs after intracellular processing (Paul, C. P. et al. Nat. Biotechnol. 20:505-508 (2002)). The endogenous expression of siRNAs from introduced DNA templates is thought to overcome some limitations of exogenous siRNA delivery, in particular the transient loss of phenotype. U6 and H1 RNA promoters are members of the type III class of Pol III promoters. (Paule, M. R. & White, R. J. Nucleic Acids Res. 28, 1283-1298 (2000)).

Co-expression of sense and antisense siRNAs mediate silencing of target genes, whereas expression of sense or antisense siRNA alone do not greatly affect target gene expression. Transfection of plasmid DNA, rather than synthetic siRNAs, may appear advantageous, considering the danger of RNase contamination and the costs of chemically synthesized siRNAs or siRNA transcription kits. Stable expression of siRNAs allows new gene therapy applications, such as treatment of persistent viral infections. Considering the high specificity of siRNAs, the approach also allows the targeting of disease-derived transcripts with point mutations, such as RAS or TP53 oncogene transcripts, without alteration of the remaining wild-type allele. Finally, by high-throughput sequence analysis of the various genomes, the DNA-based methodology may also be a cost-effective alternative for automated genome-wide loss-of-function phenotypic analysis, especially when combined with miniaturized array-based phenotypic screens. (Ziauddin, J. & Sabatini, D. M. Nature 411:107-110 (2001)).

The presence of long dsRNAs in cells stimulates the activity of a ribonuclease III enzyme referred to as dicer. Dicer is involved in the processing of the dsRNA into short pieces of dsRNA known as short interfering RNAs (siRNA) (Berstein et al., 2001, Nature, 409:363 (2001)). Short interfering RNAs derived from dicer activity are typically about 21-23 nucleotides in length and comprise about 19 base pair duplexes. Dicer has also been implicated in the excision of 21 and 22 nucleotide small temporal RNAs (stRNA) from precursor RNA of conserved structure that are implicated in translational control (Hutvagner et al., Science, 293, 834 (2001)). The RNAi response also features an endonuclease complex containing a siRNA, commonly referred to as an RNA-induced silencing complex (RISC), which mediates cleavage of single stranded RNA having sequence homologous to the siRNA. Cleavage of the target RNA takes place in the middle of the region complementary to the guide sequence of the siRNA duplex (Elbashir et al., Genes Dev., 15, 188 (2001)).

The present invention provides expression systems comprising an isolated nucleic acid molecule comprising a sequence capable of specifically hybridizing to the cancer-associated sequences. In some embodiments, the nucleic acid molecule is capable of inhibiting the expression of the cancer-associated protein. A method of inhibiting expression of cancer-associated gene expression inside a cell by a vector-directed expression of a short RNA which short RNA can fold in itself and create a double strand RNA having cancer-associated mRNA sequence identity and able to trigger posttranscriptional gene silencing, or RNA interference (RNAi), of the cancer-associated gene inside the cell. In some embodiments a short double strand RNA having a cancer-associated mRNA sequence identity is delivered inside the cell to trigger posttranscriptional gene silencing, or RNAi, of the cancer-associated gene. In various embodiments, the nucleic acid molecule is at least a 7 mer, at least a 10 mer, or at least a 20 mer. In some embodiments, the sequence is unique. In some embodiments the siRNA oligonucleotides have a sequence of SEQ ID NO:7.

The inventors have found that functional siRNAs against SEMA4D blocked proliferation and cell migration in human tumour cell lines. This supports the aspects of the invention described above.

(c) Pharmaceutical Compositions

Pharmaceutical compositions encompassed by the present invention include as active agent, the polypeptides, polynucleotides, antisense oligonucleotides, or antibodies of the invention disclosed herein in a therapeutically effective amount. An "effective amount" is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

The compositions can be used to treat cancer as well as metastases of primary cancer. In addition, the pharmaceutical compositions can be used in conjunction with conventional methods of cancer treatment, e.g., to sensitize tumors to radiation or conventional chemotherapy. The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

Where the pharmaceutical composition comprises an antibody that specifically binds to a gene product encoded by a differentially expressed polynucleotide, the antibody can be coupled to a drug for delivery to a treatment site or coupled to a detectable label to facilitate imaging of a site comprising cancer cells, such as prostate cancer cells. Methods for coupling antibodies to drugs and detectable labels are well known in the art, as are methods for imaging using detectable labels.

In some embodiments pharmaceutical compositions are provided comprising an antibody according to the present invention and a pharmaceutically suitable carrier, excipient or diluent. In some embodiments, the pharmaceutical composition further comprises a second therapeutic agent. In still another embodiment, the second therapeutic agent is a cancer chemotherapeutic agent.

A "patient" for the purposes of the present invention includes both humans and other animals, particularly mammals, and organisms. Thus the methods are applicable to both human therapy and veterinary applications. In some embodiments the patient is a mammal, and preferably the patient is human. One target patient population includes all patients currently undergoing treatment for cancer, particularly the specific cancer types mentioned herein. Subsets of these patient populations include those who have experienced a relapse of a previously treated cancer of this type in the previous six months and patients with disease progression in the past six months.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. The effective amount for a given situation is determined by routine experimentation and is within the judgment of the clinician. For purposes of the present invention, an effective dose will generally be from about 0.01 mg/kg to about 5 mg/kg, from about 0.01 mg/kg to about 50 mg/kg, or about 0.05 mg/kg to about 10 mg/kg of the compositions of the present invention in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. In some embodiments, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington: The Science and Practice of Pharmacy (1995) Alfonso Gennaro, Lippincott, Williams, & Wilkins.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The pharmaceutical compositions of the present invention comprise a cancer-associated protein in a form suitable for administration to a patient. In some embodiments, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The compounds having the desired pharmacological activity may be administered in a physiologically acceptable carrier to a host, as previously described. The pharmaceutical compositions may be administered in a variety of routes including, but not limited to, intravenous, intramuscular, intra-arterial, intramedullary, intrathecal, intraventricular, transdermal or transcutaneous applications (for example, see WO98/20734), subcutaneous, intraperitoneal, intranasal, enteral, topical, sublingual, intravaginal or rectal means. Depending upon the manner of introduction, the compounds may be formulated in a variety of ways. The concentration of therapeutically active compound in the formulation may vary from about 0.1-100% wgt/vol. Once formulated, the compositions contemplated by the invention can be (1) administered directly to the subject (e.g., as polynucleotide, polypeptides, small molecule agonists or antagonists, and the like); or (2) delivered ex vivo, to cells derived from the subject (e.g., as in ex vivo gene therapy). Direct delivery of the compositions will generally be accomplished by parenteral injection, e.g., subcutaneously, intraperitoneally, intravenously or intramuscularly, intratumoral or to the interstitial space of a tissue. Other modes of administration include oral and pulmonary administration, suppositories, and transdermal applications, needles, and gene guns (see the worldwideweb site at powderject.com) or hyposprays. Dosage treatment can be a single dose schedule or a multiple dose schedule.

Methods for the ex vivo delivery and reimplantation of transformed cells into a subject are known in the art and described in e.g., WO 93/14778. Examples of cells useful in ex vivo applications include, for example, stem cells, particularly hematopoetic, lymph cells, macrophages, dendritic cells, or tumor cells. Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Once differential expression of SEMA4D has been found to correlate with a proliferative disorder, such as neoplasia, dysplasia, and hyperplasia, the disorder can be amenable to treatment by administration of a therapeutic agent based on the provided polynucleotide, corresponding polypeptide or other corresponding molecule (e.g., antisense, ribozyme, etc.). In other embodiments, the disorder can be amenable to treatment by administration of a small molecule drug that, for example, serves as an inhibitor (antagonist) of the function of the encoded gene product of a gene having increased expression in cancerous cells relative to normal cells or as an agonist for gene products that are decreased in expression in cancerous cells (e.g., to promote the activity of gene products that act as tumor suppressors).

The dose and the means of administration of the inventive pharmaceutical compositions are determined based on the specific qualities of the therapeutic composition, the condition, age, and weight of the patient, the progression of the disease, and other relevant factors. For example, administration of polynucleotide therapeutic compositions agents includes local or systemic administration, including injection, oral administration, particle gun or catheterized administration, and topical administration. Preferably, the therapeutic polynucleotide composition contains an expression construct comprising a promoter operably linked to a polynucleotide of at least 12, 22, 25, 30, or 35 contiguous nt of the polynucleotide disclosed herein. Various methods can be used to administer the therapeutic composition directly to a specific site in the body. For example, a small metastatic lesion is located and the therapeutic composition injected several times in several different locations within the body of tumor. Alternatively, arteries that serve a tumor are identified, and the therapeutic composition injected into such an artery, in order to deliver the composition directly into the tumor. A tumor that has a necrotic center is aspirated and the composition injected directly into the now empty center of the tumor. An antisense composition is directly administered to the surface of the tumor, for example, by topical application of the composition. X-ray imaging is used to assist in certain of the above delivery methods.

Targeted delivery of therapeutic compositions containing an antisense polynucleotide, subgenomic polynucleotides, or antibodies to specific tissues can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. (USA) (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. Factors such as method of action (e.g., for enhancing or inhibiting levels of the encoded gene product) and efficacy of transformation and expression are considerations that will affect the dosage required for ultimate efficacy of the antisense subgenomic polynucleotides. Where greater expression is desired over a larger area of tissue, larger amounts of antisense subgenomic polynucleotides or the same amounts re-administered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect.

The therapeutic polynucleotides and polypeptides of the present invention can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP 0 345 242; and WO 91/02805), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:16985); eukaryotic cell delivery vehicles cells (see, e.g., U.S. Pat. No. 5,814,482; WO 95/07994; WO 96/17072; WO 95/30763; and WO 97/42338) and nucleic charge neutralization or fusion with cell membranes. Naked DNA can also be employed. Exemplary naked DNA introduction methods are described in WO 90/11092 and U.S. Pat. No. 5,580,859. Liposomes that can act as gene delivery vehicles are described in U.S. Pat. No. 5,422,120; WO 95/13796; WO 94/23697; WO 91/14445; and EP 0524968. Additional approaches are described in Philip, Mol. Cell. Biol. (1994) 14:2411, and in Woffendin, Proc. Natl. Acad. Sci. (1994) 91:1581.

Further non-viral delivery suitable for use includes mechanical delivery systems such as the approach described in Woffendin et al., Proc. Natl. Acad. Sci. USA (1994) 91(24): 11581. Moreover, the coding sequence and the product of expression of such can be delivered through deposition of photopolymerized hydrogel materials or use of ionizing radiation (see, e.g., U.S. Pat. No. 5,206,152 and WO 92/11033). Other conventional methods for gene delivery that can be used for delivery of the coding sequence include, for example, use of hand-held gene transfer particle gun (see, e.g., U.S. Pat. No. 5,149,655); use of ionizing radiation for activating transferred gene (see, e.g., U.S. Pat. No. 5,206,152 and WO 92/11033).

In some embodiments, cancer-associated proteins and modulators are administered as therapeutic agents, and can be formulated as outlined above. Similarly, cancer-associated genes (including the full-length sequence, partial sequences, or regulatory sequences of the cancer-associated coding regions) can be administered in gene therapy applications, as is known in the art. These cancer-associated genes can include antisense applications, either as gene therapy (i.e. for incorporation into the genome) or as antisense compositions, as will be appreciated by those in the art.

Thus, in some embodiments, methods of modulating cancer-associated SEMA4D activity in cells or organisms are provided. In some embodiments, the methods comprise administering to a cell an anti-cancer-associated antibody that reduces or eliminates the biological activity of an endogenous cancer-associated protein. In some embodiments, the methods comprise administering to a cell or organism a recombinant nucleic acid encoding a cancer-associated protein. As will be appreciated by those in the art, this may be accomplished in any number of ways. In some embodiments, for example when the cancer-associated sequence is down-regulated in cancer, the activity of the cancer-associated expression product is increased by increasing the amount of cancer-associated expression in the cell, for example by overexpressing the endogenous cancer-associated gene or by administering a gene encoding the cancer-associated sequence, using known gene-therapy techniques. In some embodiments, the gene therapy techniques include the incorporation of the exogenous gene using enhanced homologous recombination (EHR), for example as described in PCT/US93/03868, hereby incorporated by reference in its entirety. In some embodiments, for example when the cancer-associated sequence is up-regulated in cancer, the activity of the endogenous cancer-associated gene is decreased, for example by the administration of a cancer-associated antisense nucleic acid.

(d) Vaccines

In some embodiments, cancer-associated genes are administered as DNA vaccines, either single genes or combinations of cancer-associated genes. Naked DNA vaccines are generally known in the art. Brower, Nature Biotechnology, 16:1304-1305 (1998).

In some embodiments, cancer-associated genes of the present invention are used as DNA vaccines. Methods for the use of genes as DNA vaccines are well known to one of ordinary skill in the art, and include placing a cancer-associated gene or portion of a cancer-associated gene under the control of a promoter for expression in a patient with cancer. The cancer-associated gene used for DNA vaccines can encode full-length cancer-associated proteins, but more preferably encodes portions of the cancer-associated proteins including peptides derived from the cancer-associated protein. In some embodiments a patient is immunized with a DNA vaccine comprising a plurality of nucleotide sequences derived from a cancer-associated gene. Similarly, it is possible to immunize a patient with a plurality of cancer-associated genes or portions thereof. Without being bound by theory, expression of the polypeptide encoded by the DNA vaccine, cytotoxic T-cells, helper T-cells and antibodies are induced that recognize and destroy or eliminate cells expressing cancer-associated proteins.

In some embodiments, the DNA vaccines include a gene encoding an adjuvant molecule with the DNA vaccine. Such adjuvant molecules include cytokines that increase the immunogenic response to the cancer-associated polypeptide encoded by the DNA vaccine. Additional or alternative adjuvants are known to those of ordinary skill in the art and find use in the invention.

(e) Antibodies

The cancer-associated antibodies described above find use in a number of applications. For example, the cancer-associated antibodies may be coupled to standard affinity chromatography columns and used to purify cancer-associated proteins. The antibodies may also be used therapeutically as blocking polypeptides, as outlined above, since they will specifically bind to the cancer-associated protein.

The present invention further provides methods for detecting the presence of and/or measuring a level of a polypeptide in a biological sample, which cancer-associated polypeptide is encoded by a cancer-associated polynucleotide that is differentially expressed in a cancer cell, using an antibody specific for the encoded polypeptide. The methods generally comprise: a) contacting the sample with an antibody specific for a polypeptide encoded by a cancer-associated polynucleotide that is differentially expressed in a prostate cancer cell; and b) detecting binding between the antibody and molecules of the sample.

Detection of specific binding of the antibody specific for the encoded SEMA4D polypeptide, when compared to a suitable control is an indication that encoded polypeptide is present in the sample. Suitable controls include a sample known not to contain the encoded cancer-associated polypeptide or known not to contain elevated levels of the polypeptide; such as normal tissue, and a sample contacted with an antibody not specific for the encoded polypeptide, e.g., an anti-idiotype antibody. A variety of methods to detect specific antibody-antigen interactions are known in the art and can be used in the method, including, but not limited to, standard immunohistological methods, immunoprecipitation, an enzyme immunoassay, and a radioimmunoassay. In general, the specific antibody will be detectably labeled, either directly or indirectly. Direct labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. The antibody may be attached (coupled) to an insoluble support, such as a polystyrene plate or a bead. Indirect labels include second antibodies specific for antibodies specific for the encoded polypeptide ("first specific antibody"), wherein the second antibody is labeled as described above; and members of specific binding pairs, e.g., biotin-avidin, and the like. The biological sample may be brought into contact with and immobilized on a solid support or carrier, such as nitrocellulose, that is capable of immobilizing cells, cell particles, or soluble proteins. The support may then be washed with suitable buffers, followed by contacting with a detectably-labeled first specific antibody. Detection methods are known in the art and will be chosen as appropriate to the signal emitted by the detectable label. Detection is generally accomplished in comparison to suitable controls, and to appropriate standards.

In some embodiments, the methods are adapted for use in vivo, e.g., to locate or identify sites where cancer cells are present. In these embodiments, a detectably-labeled moiety, e.g., an antibody, which is specific for a cancer-associated polypeptide is administered to an individual (e.g., by injection), and labeled cells are located using standard imaging techniques, including, but not limited to, magnetic resonance imaging, computed tomography scanning, and the like. In this manner, cancer cells are differentially labeled.

(f) Other methods for the Detection and Diagnosis of Cancers

Without being bound by theory, the SEMA4D sequences disclosed herein appear to be important in cancers. Accordingly, disorders based on mutant or variant cancer-associated genes may be determined. In some embodiments, the invention provides methods for identifying cells containing variant cancer-associated genes comprising determining all or part of the sequence of at least one endogenous cancer-associated genes in a cell. As will be appreciated by those in the art, this may be done using any number of sequencing techniques. In some embodiments, the invention provides methods of identifying the cancer-associated genotype of an individual comprising determining all or part of the sequence of at least one cancer-associated gene of the individual. This is generally done in at least one tissue of the individual, and may include the evaluation of a number of tissues or different samples of the same tissue. The method may include comparing the sequence of the sequenced cancer-associated gene to a known cancer-associated gene, i.e., a wild-type gene. As will be appreciated by those in the art, alterations in the sequence of some cancer-associated genes can be an indication of either the presence of the disease, or propensity to develop the disease, or prognosis evaluations.

The sequence of all or part of the SEMA4D gene can then be compared to the sequence of a known SEMA4D gene to determine if any differences exist. This can be done using any number of known homology programs, such as Bestfit, etc. In some embodiments, the presence of a difference in the sequence between the cancer-associated gene of the patient and the known cancer-associated gene is indicative of a disease state or a propensity for a disease state, as outlined herein.

In some embodiments, the SEMA4D gene is used as a probe to determine the number of copies of the cancer-associated gene in the genome. For example, some cancers exhibit chromosomal deletions or insertions, resulting in an alteration in the copy number of a gene.

In some embodiments, the SEMA4D gene is used as a probe to determine the chromosomal location of the cancer-associated genes. Information such as chromosomal location finds use in providing a diagnosis or prognosis in particular when chromosomal abnormalities such as translocations, and the like are identified in cancer-associated gene loci.

The present invention provides methods of using the polynucleotides described herein for detecting cancer cells, facilitating diagnosis of cancer and the severity of a cancer (e.g., tumor grade, tumor burden, and the like) in a subject, facilitating a determination of the prognosis of a subject, and assessing the responsiveness of the subject to therapy (e.g., by providing a measure of therapeutic effect through, for example, assessing tumor burden during or following a chemotherapeutic regimen). Detection can be based on detection of a polynucleotide that is differentially expressed in a cancer cell, and/or detection of a polypeptide encoded by a polynucleotide that is differentially expressed in a cancer cell. The detection methods of the invention can be conducted in vitro or in vivo, on isolated cells, or in whole tissues or a bodily fluid e.g., blood, plasma, serum, urine, and the like).

In some embodiments, methods are provided for detecting a cancer cell by detecting expression in the cell of a transcript that is differentially expressed in a cancer cell. Any of a variety of known methods can be used for detection, including, but not limited to, detection of a transcript by hybridization with a polynucleotide that hybridizes to a polynucleotide that is differentially expressed in a prostate cancer cell; detection of a transcript by a polymerase chain reaction using specific oligonucleotide primers; in situ hybridization of a cell using as a probe a polynucleotide that hybridizes to a gene that is differentially expressed in a prostate cancer cell. The methods can be used to detect and/or measure mRNA levels of a gene that is differentially expressed in a cancer cell. In some embodiments, the methods comprise: a) contacting a sample with a polynucleotide that corresponds to a differentially expressed gene described herein under conditions that allow hybridization; and b) detecting hybridization, if any.

Detection of differential hybridization, when compared to a suitable control, is an indication of the presence in the sample of a polynucleotide that is differentially expressed in a cancer cell. Appropriate controls include, for example, a sample that is known not to contain a polynucleotide that is differentially expressed in a cancer cell, and use of a labeled polynucleotide of the same "sense" as the polynucleotide that is differentially expressed in the cancer cell. Conditions that allow hybridization are known in the art, and have been described in more detail above. Detection can also be accomplished by any known method, including, but not limited to, in situ hybridization, PCR (polymerase chain reaction), RT-PCR (reverse transcription-PCR), TMA, bDNA, and Nasbau and "Northern" or RNA blotting, or combinations of such techniques, using a suitably labeled polynucleotide. A variety of labels and labeling methods for polynucleotides are known in the art and can be used in the assay methods of the invention. Specificity of hybridization can be determined by comparison to appropriate controls.

Polynucleotides generally comprising at least 10 nt, at least 12 nt or at least 15 contiguous nucleotides of a polynucleotide provided herein, are used for a variety of purposes, such as probes for detection of and/or measurement of, transcription levels of a polynucleotide that is differentially expressed in a prostate cancer cell. As will be readily appreciated by the ordinarily skilled artisan, the probe can be detectably labeled and contacted with, for example, an array comprising immobilized polynucleotides obtained from a test sample (e.g., mRNA). Alternatively, the probe can be immobilized on an array and the test sample detectably labeled. These and other variations of the methods of the invention are well within the skill in the art and are within the scope of the invention.

Nucleotide probes are used to detect expression of a gene corresponding to the provided polynucleotide. In Northern blots, mRNA is separated electrophoretically and contacted with a probe. A probe is detected as hybridizing to an mRNA species of a particular size. The amount of hybridization can be quantitated to determine relative amounts of expression, for example under a particular condition. Probes are used for in situ hybridization to cells to detect expression. Probes can also be used in vivo for diagnostic detection of hybridizing sequences. Probes are typically labeled with a radioactive isotope. Other types of detectable labels can be used such as chromophores, fluorophores, and enzymes. Other examples of nucleotide hybridization assays are described in WO92/02526 and U.S. Pat. No. 5,124,246.

PCR is another means for detecting small amounts of target nucleic acids (see, e.g., Mullis et al., Meth. Enzymol. (1987) 155:335; U.S. Pat. No. 4,683,195; and U.S. Pat. No. 4,683,202). Two primer oligonucleotides that hybridize with the target nucleic acids are used to prime the reaction. The primers can be composed of sequence within or 3' and 5' to the cancer-associated polynucleotides disclosed herein. Alternatively, if the primers are 3' and 5' to these polynucleotides, they need not hybridize to them or the complements. After amplification of the target with a thermostable polymerase, the amplified target nucleic acids can be detected by methods known in the art, e.g., Southern blot. mRNA or cDNA can also be detected by traditional blotting techniques (e.g., Southern blot, Northern blot, etc.) described in Sambrook et al., "Molecular Cloning: A Laboratory Manual" (New York, Cold Spring Harbor Laboratory, 1989) (e.g., without PCR amplification). In general, mRNA or cDNA generated from mRNA using a polymerase enzyme can be purified and separated using gel electrophoresis, and transferred to a solid support, such as nitrocellulose. The solid support is exposed to a labeled probe, washed to remove any unhybridized probe, and duplexes containing the labeled probe are detected.

Methods using PCR amplification can be performed on the DNA from a single cell, although it is convenient to use at least about $10^5$ cells. The use of the polymerase chain reaction is described in Saiki et al. (1985) Science 239:487, and a review of current techniques may be found in Sambrook, et al. Molecular Cloning: A Laboratory Manual, CSH Press 1989, pp. 14.2-14.33. A detectable label may be included in the amplification reaction. Suitable detectable labels include fluorochromes, (e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA)), radioactive labels, (e.g. $^{32}$P, $^{35}$S, $^3$H, etc.), and the like. The label may be a two stage system, where the polynucleotides is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The reagents used in detection methods can be provided as part of a kit. Thus, the invention further provides kits for detecting the presence and/or a level of a polynucleotide that is differentially expressed in a cancer cell (e.g., by detection of an mRNA encoded by the differentially expressed gene of interest), and/or a polypeptide encoded thereby, in a biological sample. Procedures using these kits can be performed by clinical laboratories, experimental laboratories, medical practitioners, or private individuals. The kits of the invention for detecting a polypeptide encoded by a polynucleotide that is differentially expressed in a cancer cell may comprise a moiety that specifically binds the polypeptide, which may be an antibody that binds the polypeptide or fragment thereof. The kits of the invention used for detecting a polynucleotide that is differentially expressed in a prostate cancer cell may comprise a moiety that specifically hybridizes to such a polynucleotide. The kit may optionally provide additional components that are useful in the procedure, including, but not limited to, buffers, developing reagents, labels, reacting surfaces, means for detection, control samples, standards, instructions, and interpretive information.

The present invention further relates to methods of detecting/diagnosing a neoplastic or preneoplastic condition in a mammal (for example, a human). "Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and therametrics (e.g., monitoring a subject's condition to provide information as to the effect or efficacy of therapy).

An "effective amount" is an amount sufficient to effect beneficial or desired results, including clinical results. An effective amount can be administered in one or more administrations.

A "cell sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "cell sample" encompasses a clinical sample, and also includes cells in culture, cell supernatants, cell lysates, serum, plasma, biological fluid, and tissue samples.

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign.

The terms "individual," "subject," "host," and "patient," are used interchangeably herein and refer to any mammalian subject for whom diagnosis, treatment, or therapy is desired, particularly humans. Other subjects may include cattle, dogs, cats, guinea pigs, rabbits, rats, mice, horses, and so on. Examples of conditions that can be detected/diagnosed in accordance with these methods include cancers. Polynucleotides corresponding to genes that exhibit the appropriate expression pattern can be used to detect cancer in a subject. For a review of markers of cancer, see, e.g., Hanahan et al. Cell 100:57-70 (2000).

In some embodiments detection/diagnostic methods comprise: (a) obtaining from a mammal (e.g., a human) a biological sample, (b) detecting the presence in the sample of a cancer-associated protein and (c) comparing the amount of product present with that in a control sample. In some embodiments, the presence in the sample of elevated levels of a cancer associated gene product indicates that the subject has a neoplastic or preneoplastic condition.

Biological samples suitable for use in this method include biological fluids such as serum, plasma, pleural effusions, urine and cerebro-spinal fluid, CSF, tissue samples (e.g., mammary tumor or prostate tissue slices) can also be used in the method of the invention, including samples derived from biopsies. Cell cultures or cell extracts derived, for example, from tissue biopsies can also be used.

In some embodiments the compound is a binding protein, e.g., an antibody, polyclonal or monoclonal, or antigen binding fragment thereof, which can be labeled with a detectable marker (e.g., fluorophore, chromophore or isotope, etc). Where appropriate, the compound can be attached to a solid support such as a bead, plate, filter, resin, etc. Determination of formation of the complex can be effected by contacting the complex with a further compound (e.g., an antibody) that specifically binds to the first compound (or complex). Like the first compound, the further compound can be attached to a solid support and/or can be labeled with a detectable marker.

The identification of elevated levels of cancer-associated protein in accordance with the present invention makes possible the identification of subjects (patients) that are likely to benefit from adjuvant therapy. For example, a biological sample from a post primary therapy subject (e.g., subject having undergone surgery) can be screened for the presence of circulating cancer-associated protein, the presence of elevated levels of the protein, determined by studies of normal populations, being indicative of residual tumor tissue. Similarly, tissue from the cut site of a surgically removed tumor can be examined (e.g., by immunofluorescence), the presence of elevated levels of product (relative to the surrounding tissue) being indicative of incomplete removal of the tumor. The ability to identify such subjects makes it possible to tailor therapy to the needs of the particular subject. Subjects undergoing non-surgical therapy, e.g., chemotherapy or radiation therapy, can also be monitored, the presence in samples from such subjects of elevated levels of cancer-associated protein being indicative of the need for continued treatment. Staging of the disease (for example, for purposes of optimizing treatment regimens) can also be effected, for example, by biopsy e.g. with antibody specific for a cancer-associated protein.

(g) Animal Models and Transgenics

The cancer-associated genes also find use in generating animal models of cancers, particularly lymphoma, leukemia, breast cancer, colon cancer, kidney cancer, liver cancer, lung cancer, ovary cancer, pancreatic cancer, prostate cancer, uterine cancer, cervical cancer or skin cancer. As is appreciated by one of ordinary skill in the art, when the cancer-associated gene identified is repressed or diminished in cancer-associated tissue, gene therapy technology wherein antisense RNA directed to the cancer-associated gene will also diminish or repress expression of the gene. An animal generated as such serves as an animal model of cancer-associated that finds use in screening bioactive drug candidates. Similarly, gene knockout technology, for example as a result of homologous recombination with an appropriate gene targeting vector, will result in the absence of the cancer-associated protein. When desired, tissue-specific expression or knockout of the cancer-associated protein may be necessary.

It is also possible that the cancer-associated protein is overexpressed in cancer. As such, transgenic animals can be generated that overexpress the cancer-associated protein. Depending on the desired expression level, promoters of various strengths can be employed to express the transgene. Also, the number of copies of the integrated transgene can be determined and compared for a determination of the expression level of the transgene. Animals generated by such methods find use as animal models of cancer-associated and are additionally useful in screening for bioactive molecules to treat cancer.

Combination Therapy

In some embodiments the invention provides compositions comprising two or more SEMA4D antibodies to provide still improved efficacy against cancer. Compositions comprising two or more SEMA4D antibodies may be administered to persons or mammals suffering from, or predisposed to suffer from, cancer. One or more SEMA4D antibodies may also be administered with another therapeutic agent, such as a cytotoxic agent, or cancer chemotherapeutic. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

In some embodiments the methods provide of the invention contemplate the administration of combinations, or "cocktails", of different antibodies. Such antibody cocktails may have certain advantages inasmuch as they contain antibodies which exploit different effector mechanisms or combine directly cytotoxic antibodies with antibodies that rely on immune effector functionality. Such antibodies in combination may exhibit synergistic therapeutic effects.

A cytotoxic agent refers to a substance that inhibits or prevents the function of cells and/or causes destruction of cells. The term is intended to include radioactive isotopes (e.g., $I^{131}, I^{125}, Y^{90}$ and $Re^{186}$), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an antibody according to the invention.

In some embodiments, conventional cancer medicaments are administered with the compositions of the present invention. Conventional cancer medicaments include:
 a) cancer chemotherapeutic agents.
 b) additional agents.
 c) prodrugs.

Cancer chemotherapeutic agents include, without limitation, alkylating agents, such as carboplatin and cisplatin; nitrogen mustard alkylating agents; nitrosourea alkylating agents, such as carmustine (BCNU); antimetabolites, such as methotrexate; folinic acid; purine analog antimetabolites, mercaptopurine; pyrimidine analog antimetabolites, such as fluorouracil (5-FU) and gemcitabine (Gemzar®); hormonal antineoplastics, such as goserelin, leuprolide, and tamoxifen; natural antineoplastics, such as aldesleukin, interleukin-2, docetaxel, etoposide (VP-16), interferon alfa, paclitaxel (Taxol®), and tretinoin (ATRA); antibiotic natural antineoplastics, such as bleomycin, dactinomycin, daunorubicin, doxorubicin, daunomycin and mitomycins including mitomycin C; and vinca alkaloid natural antineoplastics, such as vinblastine, vincristine, vindesine; hydroxyurea; aceglatone, adriamycin, ifosfamide, enocitabine, epitiostanol, aclarubicin, ancitabine, nimustine, procarbazine hydrochloride, carboquone, carboplatin, carmofur, chromomycin A3, antitumor polysaccharides, antitumor platelet factors, cyclophosphamide (Cytoxine), Schizophyllan, cytarabine (cytosine arabinoside), dacarbazine, thioinosine, thiotepa, tegafur, dolastatins, dolastatin analogs such as auristatin, CPT-11 (irinotecan), mitozantrone, vinorelbine, teniposide, aminopterin, caminomycin, esperamicins (See, e.g., U.S. Pat. No. 4,675,187), neocarzinostatin, OK-432, bleomycin, furtulon, broxuridine, busulfan, honvan, peplomycin, bestatin (Ubenimex®), interferon-β, mepitiostane, mitobronitol, melphalan, laminin peptides, lentinan, *Coriolus versicolor* extract, tegafur/uracil, estramustine (estrogen/mechlorethamine).

Additional agents which may be used as therapy for cancer patients include EPO, G-CSF, ganciclovir; antibiotics, leuprolide; meperidine; zidovudine (AZT); interleukins 1 through 18, including mutants and analogues; interferons or cytokines, such as interferons α, β, and γ hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & β); invasion inhibiting factor-2 (IIF-2); bone morphogenetic proteins 1-7 (BMP 1-7); somatostatin; thymosin-α-1; γ-globulin; superoxide dismutase (SOD); complement factors; anti-angiogenesis factors; antigenic materials; and prodrugs.

Prodrug refers to a precursor or derivative form of a pharmaceutically active substance that is less cytotoxic or non-cytotoxic to tumor cells compared to the parent drug and is capable of being enzymatically activated or converted into an active or the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, b-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use herein include, but are not limited to, those chemotherapeutic agents described above.

Methods for Delivering a Cytotoxic Agent or a Diagnostic Agent to a Cell

The present invention also provides methods for delivering a cytotoxic agent or a diagnostic agent to one or more cells that express a cancer-associated gene. In some embodiments the methods comprise contacting an antibody, polypeptide or nucleotide of the present invention conjugated to a cytotoxic agent or diagnostic agent with the cell. Such conjugates are discussed above.

Affinity Purification

In some embodiments the invention provides methods and compositions for affinity purification. In some embodiments, antibodies of the invention are immobilized on a solid phase such a Sephadex resin or filter paper, using methods well known in the art. The immobilized antibody is contacted with a sample containing the tumor cell antigen protein (or fragment thereof) to be purified, and thereafter the support is washed with a suitable solvent that will remove substantially all the material in the sample except the tumor cell antigen protein, which is bound to the immobilized antibody. Finally, the support is washed with another suitable solvent, such as glycine buffer, pH 5.0, that will release the tumor cell antigen protein from the antibody.

EXAMPLES

The following examples are described so as to provide those of ordinary skill in the art with a complete disclosure and description of how to make and use the present invention, and are not intended to limit the scope of what the inventors regard as their invention nor are they intended to represent that the experiments below are all and only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Insertion Site Analysis Following Tumor Induction in Mice

Tumors were induced in mice using either mouse mammary tumor virus (MMTV) or murine leukemia virus (MLV). MMTV causes mammary adenocarcinomas and MLV causes a variety of different hematopoetic malignancies (primarily T- or B-cell lymphomas).

Three routes of infection were used: (1) injection of neonates with purified virus preparations, (2) infection by milkborne virus during nursing, and (3) genetic transmission of pathogenic proviruses via the germ-line (Akvr1 and/or Mtv2). The type of malignancy present in each affected mouse was determined by histological analysis of H&E-stained thin sections of formalin-fixed, paraffin-embedded biopsy samples. Host DNA sequences flanking all clonally-integrated proviruses in each tumor were recovered by nested anchored-PCR using two virus-specific primers and two primers specific for a 40 bp double stranded DNA anchor ligated to restriction enzyme digested tumor DNA. Amplified bands representing host/virus junction fragments were cloned and sequenced. Then the host sequences (called "tags") were used to BLAST analyze the mouse genomic sequence.

Extracted mouse genomic tag sequences were then mapped to the draft mouse genome assembly (NCBI m33 release) downloaded from www.ensembl.org. Tag sequences 45 bp or longer were mapped to the genome using Timelogic's accelerated blast algorithm, terablast, with the following parameter setup: −t=10−X=1e−10−v=20−b=20−R. Short tag sequences (<45 bp) were mapped to the genome by NCBI blastall algorithm, with the following parameter setup: -e 1000-F F—W 9-v 20-b 20. The combined blast results were then filtered for the best matches for each tag sequence, which typically requires a minimum of 95% identity over at least 30% of the tag sequence length. Tags with uniq chromosome locations were passed on to the gene call process.

For each individual tag, three parameters were recorded: (1) the mouse chromosome assignment, (2) base pair coordinates at which the integration occurred, and (3) provirus orientation. Using this information, all available tags from all analyzed tumors were mapped to the mouse genome. To identify the protooncogene targets of provirus insertion mutation, the provirus integration pattern at each cluster of integrants was analyzed relative to the locations of all known genes in the transcriptome. The presence of provirus at the same locus in two or more independent tumors is prima facie evidence that a protooncogene is present at or very near the proviral integration sites. This is because the genome is too large for random integrations to result in observable clustering. Any clustering that was detected provides unequivocal evidence for biological selection during tumorigenesis. In order to identify the human orthologs of the protooncogene targets of provirus insertion mutation, a comparative analysis of syntenic regions of the mouse and human genomes was performed.

Ensembl mouse gene models and UCSC refseq and known gene sets were used to represent the mouse transcriptome. As noted above, based on the tag chromosome positions and the proviral insertion orientation relative to the adjacent genes, each tag was assigned to its nearest neighboring gene. Proviral insertions linked to a gene were grouped in 2 categories, type I insertions or type II insertions. If the insertion was within the gene locus, either intron or exon, it was designated as a type II insertion. If not, the insertion was designated as a type I insertion provided the insertion fulfilled these additional criteria: 1) it was outside the gene locus but within 100 kilobases from the gene's start or end positions, 2) for upstream insertions, the proviral orientation was the opposite to that of the gene, and 3) for downstream insertion, the proviral orientation was the same as the gene. Genes or transcripts discovered in this process were assigned with locus IDs from NCBI Locus Link annotations. The uniq mouse locus IDs with at least 2 viral inserts make up the current Oncogenome™.

To assign human orthologs for the mouse genes in the Oncogenome™, the MGI's mouse to human ortholog annotation and NCBI's homologue annotation was used. When there were conflicts or lack of ortholog annotation, comparative analysis of syntenic regions of the mouse and human genomes was performed, using the UCSC or Ensembl genome browser. The orthologous human genes were assigned with Locus Id's from NCBI Locus Link, and these human genes were further evaluated as potential targets for cancer therapeutics as described herein.

Example 2

Analysis of Quantitative RT-PCR Comparative $C_T$ Method

The RT-PCR analysis was divided into 4 major steps: 1) RNA purification from primary normal and tumor tissues; 2) Generation of first strand cDNA from the purified tissue RNA for Real Time Quantitative PCR; 3) Setup RT-PCR for gene expression using ABI PRISM 7900HT Sequence Detection System tailored for 384-well reactions; 4) Analyze RT-PCR data by statistical methods to identify genes differentially expressed (up-regulated) in cancer. These steps are set out in more detail below.

A) RNA purification from primary normal and tumor tissues

This was performed using Qiagen RNeasy mini Kit CAT#74106. Tissue chucks typically yielded approximately 30 µg of RNA resulting in a final concentration of approximately 200 ng/µl if 150 µl of elution buffer was used.

After RNA was extracted using Qiagen's protocol, Ribogreen quantitation reagents from Molecular Probes was used to determine yield and concentration of RNA according to manufacture protocol.

Integrity of extracted RNA was assessed on EtBr stained agarose gel to determine if the 28S and 18S band have equal intensity. In addition, sample bands should be clear and visible. If bands were not visible or smeared down through the gel, the sample was discarded.

Integrity of extracted RNA was also assessed using Agilent 2100 according to manufacture protocol. The Agilent Bioanalyzer/"Lab-On-A-Chip" is a micro-fluidics system that generates an electropherogram of an RNA sample. By observing the ratio of the 18S and 28S bands and the smoothness of the baseline a determination of the level of RNA degradation was made. Samples that have 28S: 18S ratios below 1 were discarded.

RNA samples were also examined by RT-PCR to determine level of genomic DNA contamination during extraction. In general, RNA samples were assayed directly using validated Taqman primers and probes of gene of interest in the presence and absence of Reverse Transcriptase. 12.5 ng of RNA was used per reaction in quadruplicate in a 384 wells format in a volume of 5 ul per well. (2 ul of RNA+3 ul of RT+ or RT-master mix). The following thermocycle parameters was used (2-step PCR):

Thermocycling Parameters

|  | Step | | | |
| --- | --- | --- | --- | --- |
|  | Reverse Transcription | Amp. Gold Activation | PCR 40 CYCLES | |
|  | HOLD | HOLD | Denature | Anneal/Extend |
| Temperature | 48° C. | 95° C. | 95° C. | 60° C. |
| Time | 30 min. | 10 min. | 15 sec. | 1 min |

RNA samples required the following criteria to consider as pass QC.
a) Ct difference must be 7 Ct or greater for a pass. Anything less is a "fail" and should be re-purified.
b) Mean sample Ct must be within 2 STDEV (all samples) from Mean (all samples) to pass.
c) Use conditional formatting to find the outliers of the sample group. *Do not include the outliers on the RNA panels.
d) RT amplification or (Ct) must be >34 cycles or it is a "fail".
e) Human genomic DNA must be between 23 and 27.6 Ct.

RNA was assembled into panel only if samples passed all QC steps (Gel run, Agilent and RT-PCR for genomic DNA). RNA was arrayed for cDNA synthesis. In general, a minimum of 10 normals and 20 tumors were required for each tumor type (i.e., if a tissue type can have a squamous cell carcinoma and an adenocarcinoma, 20 samples of each tumor type must be used (the same 10 normals will be used for each tumor type)). In general, 11 µg of RNA was required per panel. A factor of at least 2 µg should be allowed; i.e., samples in database must have 13 µg, or they will be dropped during cDNA array. Sample numbers were arranged in ascending orders, starting at well A1 and working down the column on 96 wells format. Four control samples will be placed at the end of the panel: hFB, hrRNA, hgDNA and Water (in that order). An additional NTC control (water) was be placed in well A2. All lot numbers of controls were recorded. RNA samples were normalized to 100 ng/41 in Nuclease-free water. 11 µg of RNA was used, the total volume being 110 µl. NOTE: the concentration of RNA required can vary depending on the particular cDNA synthesis kit used. RNA samples that were below 100 ng/µl, were loaded pure. After normalization was complete, the block was sealed using the heat sealer with easy peel foil @ 175° C. for 2 seconds. The block was visually inspected to make sure foil was completely sealed. The manual sealer was then run over the foil. The block was stored in the −80° C. freezers, ready for cDNA synthesis.

B) Generation of first strand cDNA from the purified tissue RNA for Real Time Quantitative PCR:

The following reaction mixture was setup in advance:

| Reagents | 1 RXN Volumes (µl) | RXN |
| --- | --- | --- |
| 10X Taqman RT BUFFER | 1 | |
| 25 mM Magnesium chloride | 2.2 | |
| 10 mM deoxyNTPS mixture | 2 | |
| 50 uM Random Hexamer | 0.5 | |
| Rnase inhibitor | 0.2 | |
| 50 u/ul MultiScribe Rev. Transcriptase | 0.25 | |
| Water | 0.85 | |

Arrayed RNA in a 96 well block (11 µg) was distributed to daughter plates using Hydra to create 1 µg of cDNA synthesis per 96 well plate. Each of these daughter plates was used to setup RT reaction using the following thermocycle parameters:

|  | Step | | |
| --- | --- | --- | --- |
|  | Incubation Hold | RT Hold | RT Inactivation Hold |
| Time | 10 min. | 30 min. | 5 min. |
| Temperature | 25° C. | 48° C. | 95° C. |

Upon completion of thermocyling, plates were removed from the cycler and using the Hydra pipette, 60 µl of 0.016M EDTA solution was pippetted into every well of cDNA the plates. Each cDNA plate (no more than 10 plates) was be pooled to a 2 ml-96 well block for storage.

RT-PCR for gene expression using ABI PRISM 7900HT Sequence Detection System tailored for 384-well reactions:

Create Cocktails

Cocktails were produced as follows:
1. This protocol was designed to create cocktails for a panel with 96 samples; this is 470 rxns for the whole panel.
2. FRT (Forward and Reverse primers and Target probe) mix was removed from −20° C. and place in 4° C. fridge thaw.
3. The first 10 FRT's to be made were taken out and placed in a cold metal rack or in a rack on ice.
4. New 1.5 ml cocktail tube caps were labelled with target number, side with the date of synthesis (found on FRT tube, if no date of synthesis label with today's date), and initials of scientist, one tube for each FRT being made.
5. FRT tubes and cocktails tubes were organised in rack so that they were in order and easy to keep track of.
6. When pipetting a p200 was used at speed 6. Aspiration was carried out at the surface of the liquid, and dispensed near the top of the inside of the tube. Tips were changed after each aspirate/dispense step.
6.1 All cocktail tubes were opened and 94 µl Ambion water (poured fresh daily) was added, then tubes were closed.
6.2 The FRT was Pulse vortexed 15 times, then centrifuged for 10 sec. One by one 141 µl of FRT was added to corresponding cocktail tubes.
6.3 When done with first 10, FRT was put back to −20° C. immediately (if vol was less than 10 µl then they were thrown away).

6.4 Cocktail was stored in 4° C. until ready to run. (−20° C. f it wait was longer than 1 day)
6.5 Master mix was added to cocktails when ready to run cocktails (refer to step 2.7)
7. Steps 1.3 to 1.6.5 were repeated for the next 10 cocktails, and so on until all cocktails had been made.

| TaqMan Master Mix | 1 rxn volume | 470 RXNS | |
|---|---|---|---|
| TaqMan Universal Master Mix Lot# | 2.5 μl | 1175 μl | |
| Forward Primer working stock | 0.1 μl | 47 μl | |
| Reverse Primer working stock | 0.1 μl | 47 μl | 141 μl |
| Probe working stock | 0.1 μl | 47 μl | |
| Water | 0.2 μl | 94 μl | |
| Final Volume | 3.0 μl | 1410 μl | |

2 μl of cDNA from the arrayed 96-well plates was added to the 3 μl of Taqman Master Mix to makeup a 5 μl QPCR reaction.

The primers and probes used in the QPCR for the SEMA4D gene are given in Table 2.

TABLE 2

Table of Target-Specific Primer/Probe Sets

| Gene | Sgrs ID | Forward Primer | Reverse Primer | Probe Sequence |
|---|---|---|---|---|
| SEMA4D | 38 | GGTGCCTGTGTTCTATGCACTCT (SEQ ID NO: 4) | GACAGGTTGTAGGCGCACACT (SEQ ID NO: 5) | ACCCCACAGCTGAACAACGTGGG (SEQ ID NO: 6) |

D) Analyze RT-PCR Data by Statistical Methods to Identify Genes Differentially Expressed (Up-Regulated) in Cancer:

The expression level of a target gene in both normal and tumor samples was determined using Quantitative RT-PCR using the ABI PRISM 7900HT Sequence Detection System (Applied Biosystems, California). The method is based on the quantitation of the initial copy number of target template in comparison to that of a reference (normalizer) housekeeper gene (Pre-Developed TaqMan® Assay Reagents Gene Expression Quantification Protocol, Applied Biosystems, 2001). Accumulation of DNA product with each PCR cycle is related to amplicon efficiency and the initial template concentration. Therefore the amplification efficiency of both the target and the normalizer must be similar. The threshold cycle ($C_T$), which is dependent on the starting template copy number and the DNA amplification efficiency, is a PCR cycle during which PCR product growth is exponential. Each assay was performed in quadruplicates; therefore, 4 $C_T$ values were obtained for the target gene in a given sample. Simultaneously, the expression level of a group of housekeeper genes were also measured in the same fashion. The outliner within the 4 quadruplicates is detected and removed if the standard deviation of the remaining 3 triplicates is 30% or less compared to the standard deviation of the original 4 quadruplicates. The mean of the remaining $C_T$ values (designated as $C_t$ or $C_n$) was calculated and used in the following computation.

Data Normalization.

For normalization, a 'universal normalizer' was developed that is based on the set of housekeepers available for analysis (5 to 8 genes). Briefly, the housekeeper genes were weighted according to their variations in expression level across the whole panel of tissue samples. For n samples of the same tissue type, the weight (w) for the kth house keeper gene was calculated with the following formulas:

$$w_k = \frac{1/S_k^2}{\sum_{k=1}^{n} 1/S_k^2} \quad \text{Equation 1}$$

Where $S_k$ stands for the standard deviation of the kth housekeeper gene across the all samples of same tissue type in the panel. The mean expression of all housekeeper genes in the ith sample (Mi) was estimated using the weighted least square method, and the difference between the Mi and the average of all Mi is computed as the normalization factor Ni for the ith sample (Equation 2). The mean Ct value of the target gene in the ith sample was then normalized by subtracting the normalization factor Ni. The performance of the above normalization method was validated by comparing the correlation between RT-PCR and microarray data that were generated from the same set of samples: increased correlation between RT-PCR data and microarray data was observed after applying the above normalization method.

$$N_i = M_i - \frac{\sum_{i=1}^{n} M_i}{n} \quad \text{Equation 2}$$

Identification of Significantly Dysregulated Genes.

To determine if a gene is significantly up-regulated in the tumor versus normal samples, two statistics, t (Equation 3) and Receiver Operating Characteristic (ROC; Equation 4) were calculated:

$$t = \frac{\overline{C_t} - \overline{C_n}}{\sqrt{\frac{S_t^2}{n_t} + \frac{S_n^2}{n_n}}} \quad \text{Equation 3}$$

$$ROC(t_0) = P[C_t < C_n(t_0)] \quad \text{Equation 4}$$

where $\overline{C_t}$ is the average of $C_t$ in the tumor sample group, $\overline{C_n}$ is the average of $C_n$ in the normal sample group, $S_t$, $S_n$ are standard deviations of the tumor and normal control groups, and $n_t$, $n_n$ are the number of the tumor and normal samples used in the analysis. The degree of freedom v' of t is calculated as:

$$v' = \frac{\left(\frac{S_t^2}{n_t} + \frac{S_n^2}{n_n}\right)^2}{\frac{\left(\frac{S_t^2}{n_t}\right)^2}{n_t - 1} + \frac{\left(\frac{S_n^2}{n_n}\right)^2}{n_n - 1}} \quad \text{Equation 5}$$

In the ROC equation, $t_0$ is the accepted false positive rate in the normal population, which is set to 0.1 in our study. Therefore, $C_n(t_0)$ is the 10 percentile of $C_n$ in the normal samples, and the ROC (0.1) is the percentage of tumor samples with $C_t$ lower than the 10 percentile of the normal samples. The t statistic identifies genes that show higher average expression level in tumor samples compared to normal samples, while the ROC statistic is more suitable to identify genes that show elevated expression level only in a subset of tumors. The rationale of using ROC statistic is discussed in detail in Pepe, et al (2003) Biometrics 59, 133-142. The distribution of t under null hypothesis is empirically estimated by permutation to avoid normal distribution assumption, in which we randomly assign normal or tumor labels to the samples, and then calculate the t statistic ($t^p$) as above for 2000 times. The p value was then calculated as the number of $t^p$ less than t from real samples divided by 2000. To access the variability of ROC, the samples were bootstrapped 2000 times, each time, a bootstrap ROC($ROC^b$) was calculated as above. If 97.5% of 2000 $ROC^b$ is above 0.1, the acceptable false positive rate we set for normal population, the ROC from the real samples was then considered as statistically significant. The threshold to determine significance was set at >20% incidence for ROC and <0.05 for the T-test P value.

Application of the above methodologies allowed us to model 3 hypothetical distributions between the normal and sample sets.

In scenario I, there was essentially complete separation between the two sample populations (control and disease). Both the ROC and T-Test score this scenario with high significance. In scenario II, the samples exhibit overlapping distributions and only a subset of the disease sample is distinct from the control (normal) population. Only the ROC method will score this scenario as significant. In scenario III, the disease sample population overlaps entirely with the control population. In contrast to scenario I and II, only the T-Test method will score this scenario as significant. In sum, the combination of both statistical methods allows one to accurately characterize the expression pattern of a target gene within a sample population.

Results of this test are expressed in Table 3 below. SEMA4D overexpression was seen in breast, ovarian, colon, prostate and pancreatic cancer tissues.

Polymerase chain reaction (PCR) is performed using Taq polymerase following the conditions recommended by the manufacturer (Perkin Elmer Cetus) with regard to buffer, Mg2+, and nucleotide concentrations. Thermocycling is performed in a DNA cycler by denaturation at 94° C. for 3 min. followed by either 35 or 50 cycles of 94° C. for 1.5 min., 50° C. for 2 min. and 72° C. for 3 min. The ability of the PCR to amplify the selected regions of the cancer-associated gene is tested by using a cloned cancer-associated polynucleotide(s) as a positive template(s). Optimal Mg2+, primer concentrations and requirements for the different cycling temperatures are determined with these templates. The master mix recommended by the manufacturer is used. To detect possible contamination of the master mix components, reactions without template are routinely tested.

Southern blotting and hybridization are performed as described by Southern, E. M., (J. Mol. Biol. 98:503-517, 1975), using the cloned sequences labeled by the random primer procedure (Feinberg, A. P., et al., 1983, Anal. Biochem. 132:6-13). Prehybridization and hybridization are performed in a solution containing 6×SSPE, 5% Denhardt's, 0.5% SDS, 50% formamide, 100 μg/ml denatured salmon testis DNA, incubated for 18 hrs at 42° C., followed by washings with 2×SSC and 0.5% SDS at room temperature and at 37° C. and finally in 0.1×SSC with 0.5% SDS at 68° C. for 30 min (Sambrook et al., 1989, in "Molecular Cloning: A Laboratory Manual", Cold Spring Harbor Lab. Press). For paraffin-embedded tissue sections the conditions described by Wright and Manos (1990, in "PCR Protocols", Innis et al., eds., Academic Press, pp. 153-158) are followed using primers designed to detect a 250 bp sequence.

Example 4

Expression of Cloned Polynucleotides in Host Cells

To study the protein products of cancer-associated genes, restriction fragments from cancer-associated DNA are cloned

TABLE 3

ROC % incidence is given where calculated.

| Source Data | Analysis method | Cancer Typer, % Incidence vs. Corresponding Normal | | | | | | | | | | |
|---|---|---|---|---|---|---|---|---|---|---|---|---|
| | | Breast | Cervix | Colon | Lymphoid | Liver | Lung | Ovary | Pancreas | Prostate | Skin | Uterus |
| Sagres Q-PCR | ROC P-Value | 33% 0.047 | ns 0.235 | ns 0.00001 | ns 0.8645 | ns 0.105 | ns 0.233 | 87% 0.00001 | 40% 0.2145 | ns 0.0065 | ns 0.15 | ns 0.866 |

Where incidence was not significant the "t" value is given. ns = not siginificant but no t value given. Number of insertions and type of insertions are also given along with the virus type used.

Results for gene disregulation in individual cancerous and non-cancerous tissues are shown in FIG. 3. Expression profiling in normal tissue is shown in FIG. 4.

Example 3

Detection of Cancer-Associated-Sequences in Human Cancer Cells and Tissues

DNA from prostate and breast cancer tissues and other human cancer tissues, human colon, normal human tissues including non-cancerous prostate, and from other human cell lines are extracted following the procedure of Delli Bovi et al. (1986, Cancer Res. 46:6333-6338). The DNA is resuspended in a solution containing 0.05 M Tris HCl buffer, pH 7.8, and 0.1 mM EDTA, and the amount of DNA recovered is determined by microfluorometry using Hoechst 33258 dye. Cesarone, C. et al., Anal Biochem 100:188-197 (1979).

into the expression vector pMT2 (Sambrook, et al., Molecular Cloning: A Laboratory Manual, Cold Spring Harbor Laboratory Press pp 16.17-16.22 (1989)) and transfected into COS cells grown in DMEM supplemented with 10% FCS. Transfections are performed employing calcium phosphate techniques (Sambrook, et al (1989) pp. 16.32-16.40, supra) and cell lysates are prepared forty-eight hours after transfection from both transfected and untransfected COS cells. Lysates are subjected to analysis by immunoblotting using anti-peptide antibody.

In immunoblotting experiments, preparation of cell lysates and electrophoresis are performed according to standard procedures. Protein concentration is determined using BioRad protein assay solutions. After semi-dry electrophoretic transfer to nitrocellulose, the membranes are blocked in 500 mM NaCl, 20 mM Tris, pH 7.5, 0.05% Tween-20 (TTBS) with 5% dry milk. After washing in TTBS and incubation with secondary antibodies (Amersham), enhanced chemiluminescence (ECL) protocols (Amersham) are performed as described by the manufacturer to facilitate detection.

Example 5

Generation of Antibodies Against Polypeptides

Polypeptides, unique to cancer-associated genes are synthesized or isolated from bacterial or other (e.g., yeast, baculovirus) expression systems and conjugated to rabbit serum albumin (RSA) with m-maleimido benzoic acid N-hydroxysuccinimide ester (MBS) (Pierce, Rockford, Ill.). Immunization protocols with these peptides are performed according to standard methods. Initially, a pre-bleed of the rabbits is performed prior to immunization. The first immunization includes Freund's complete adjuvant and 500 µg conjugated peptide or 10 µg purified peptide. All subsequent immunizations, performed four weeks after the previous injection, include Freund's incomplete adjuvant with the same amount of protein. Bleeds are conducted seven to ten days after the immunizations.

For affinity purification of the antibodies, the corresponding cancer-associated polypeptide is conjugated to RSA with MBS, and coupled to CNBr-activated Sepharose (Pharmacia, Uppsala, Sweden). Antiserum is diluted 10-fold in 10 mM Tris-HCl, pH 7.5, and incubated overnight with the affinity matrix. After washing, bound antibodies are eluted from the resin with 100 mM glycine, pH 2.5.

Example 6

Generation of Monoclonal Antibodies Against a Cancer-Associated Polypeptide

A non-denaturing adjuvant (Ribi, R730, Corixa, Hamilton Mont.) is rehydrated to 4 ml in phosphate buffered saline. 100 µl of this rehydrated adjuvant is then diluted with 400 µl of Hank's Balanced Salt Solution and this is then gently mixed with the cell pellet used for immunization. Approximately 500 µg conjugated peptide or 100 µg purified peptide and Freund's complete are injected into Balb/c mice via foot-pad, once a week. After 6 weeks of weekly injection, a drop of blood is drawn from the tail of each immunized animal to test the titer of antibodies against cancer-associated polypeptides using FACS analysis. When the titer reaches at least 1:2000, the mice are sacrificed in a CO2 chamber followed by cervical dislocation. Lymph nodes are harvested for hybridoma preparation. Lymphocytes from mice with the highest titer are fused with the mouse myeloma line X63-Ag8.653 using 35% polyethylene glycol 4000. On day 10 following the fusion, the hybridoma supernatants are screened for the presence of CAP-specific monoclonal antibodies by fluorescence activated cell sorting (FACS). Conditioned medium from each hybridoma is incubated for 30 minutes with a combined aliquot of PC3, Colo-205, LnCap, or Panc-1 cells. After incubation, the cell samples are washed, resuspended in 0.1 ml diluent and incubated with 1 µg/ml of FITC conjugated F(ab')2 fragment of goat anti-mouse IgG for 30 min at 4° C. The cells are washed, resuspended in 0.5 ml FACS diluent and analyzed using a FACScan cell analyzer (Becton Dickinson; San Jose, Calif.). Hybridoma clones are selected for further expansion, cloning, and characterization based on their binding to the surface of one or more of cell lines which express the cancer-associated polypeptide as assessed by FACS. A hybridoma making a monoclonal antibody designated mAb-cancer-associated which binds an antigen designated Ag—CA.x and an epitope on that antigen designated Ag—CA.x. 1 is selected.

Example 7

ELISA Assay for Detecting Cancer-Associated Antigen Related Antigens

To test blood samples for antibodies that bind specifically to recombinantly produced cancer-associated antigens, the following procedure is employed. After a recombinant cancer-associated related protein is purified, the recombinant protein is diluted in PBS to a concentration of 5 µg/ml (500 ng/100 µl). 100 microliters of the diluted antigen solution is added to each well of a 96-well Immulon 1 plate (Dynatech Laboratories, Chantilly, Va.), and the plate is then incubated for 1 hour at room temperature, or overnight at 4° C., and washed 3 times with 0.05% Tween 20 in PBS. Blocking to reduce nonspecific binding of antibodies is accomplished by adding to each well 200 µl of a 1% solution of bovine serum albumin in PBS/Tween 20 and incubation for 1 hour. After aspiration of the blocking solution, 100 µl of the primary antibody solution (anticoagulated whole blood, plasma, or serum), diluted in the range of 1/16 to 1/2048 in blocking solution, is added and incubated for 1 hour at room temperature or overnight at 4° C. The wells are then washed 3 times, and 100 µl of goat anti-human IgG antibody conjugated to horseradish peroxidase (Organon Teknika, Durham, N.C.), diluted 1/500 or 1/1000 in PBS/Tween 20, 100 µl of o-phenylenediamine dihydrochloride (OPD, Sigma) solution is added to each well and incubated for 5-15 minutes. The OPD solution is prepared by dissolving a 5 mg OPD tablet in 50 ml 1% methanol in $H_2O$ and adding 50 µl 30% $H_2O_2$ immediately before use. The reaction is stopped by adding 251 µl of 4M $H_2SO_4$. Absorbances are read at 490 nm in a microplate reader (Bio-Rad).

Example 8

Identification and Characterization of Cancer-Associated Antigen on Cancer Cell Surface A cell pellet of proximately 25 ul packed cell volume of a cancer cell preparation is lysed by first diluting the cells to 0.5 ml in water followed by freezing and thawing three times. The solution is centrifuged at 14,000 rpm. The resulting pellet, containing the cell membrane fragments, is resuspended in 50 µl of SDS sample buffer (Invitrogen, Carlsbad, Calif.). The sample is heated at 80° C. for 5 minutes and then centrifuged for 2 minutes at 14,000 rpm to remove any insoluble materials.

The samples are analyzed by Western blot using a 4 to 20% polyacrylamide gradient gel in Tris-Glycine SDS (Invitrogen; Carlsbad Calif.) following the manufacturer's directions. Ten microliters of membrane sample are applied to one lane on the polyacrylamide gel. A separate 10 µL sample is reduced first by the addition of 2 µL of dithiothreitol (100 mM) with heating at 80° C. for 2 minutes and then loaded into another lane. Pre-stained molecular weight markers SeeBlue Plus2 (Invitrogen; Carlsbad, Calif.) are used to assess molecular weight on the gel. The gel proteins are transferred to a nitrocellulose membrane using a transfer buffer of 14.4 g/l glycine, 3 g/l of Tris Base, 10% methanol, and 0.05% SDS. The membranes are blocked, probed with a CAP-specific monoclonal antibody (at a concentration of 0.5 ug/ml), and developed using the Invitrogen WesternBreeze Chromogenic Kit-AntiMouse according to the manufacturer's directions.

In the reduced sample of the tumor cell membrane samples, a prominent band is observed migrating at a molecular weight within about 10% of the predicted molecular weight of the corresponding cancer-associated protein.

Example 9

Preparation of Vaccines

The present invention also relates to a method of stimulating an immune response against cells that express cancer-associated polypeptides in a patient using cancer-associated polypeptides of the invention that act as an antigen produced by or associated with a malignant cell. This aspect of the invention provides a method of stimulating an immune response in a human against cancer cells or cells that express cancer-associated polynucleotides and polypeptides. The method comprises the step of administering to a human an immunogenic amount of a polypeptide comprising: (a) the amino acid sequence of a huma cancer-associated protein or (b) a mutein or variant of a polypeptide comprising the amino acid sequence of a human endogenous retrovirus cancer-associated protein.

Example 10

Generation of Transgenic Animals Expressing Polypeptides as a Means for Testing Therapeutics Cancer-associated nucleic acids are used to generate genetically modified non-human animals, or site specific gene modifications thereof, in cell lines, for the study of function or regulation of prostate tumor-related genes, or to create animal models of diseases, including prostate cancer. The term "transgenic" is intended to encompass genetically modified animals having an exogenous cancer-associated gene(s) that is stably transmitted in the host cells where the gene(s) may be altered in sequence to produce a modified protein, or having an exogenous cancer-associated LTR promoter operably linked to a reporter gene. Transgenic animals may be made through a nucleic acid construct randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

The modified cells or animals are useful in the study of cancer-associated gene function and regulation. For example, a series of small deletions and/or substitutions may be made in the cancer-associated genes to determine the role of different genes in tumorigenesis. Specific constructs of interest include, but are not limited to, antisense constructs to block cancer-associated gene expression, expression of dominant negative cancer-associated gene mutations, and over-expression of a cancer-associated gene. Expression of a cancer-associated gene or variants thereof in cells or tissues where it is not normally expressed or at abnormal times of development is provided. In addition, by providing expression of proteins derived from cancer-associated in cells in which it is otherwise not normally produced, changes in cellular behavior can be induced.

DNA constructs for random integration need not include regions of homology to mediate recombination. Conveniently, markers for positive and negative selection are included. For various techniques for transfecting mammalian cells, see Keown et al., Methods in Enzymology 185:527-537 (1990).

For embryonic stem (ES) cells, an ES cell line is employed, or embryonic cells are obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells are transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting chimeric animals screened for cells bearing the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs are maintained as allogeneic or congenic grafts or transplants, or in in vitro culture. The transgenic animals may be any non-human mammal, such as laboratory animals, domestic animals, etc. The transgenic animals are used in functional studies, drug screening, etc., e.g. to determine the effect of a candidate drug on prostate cancer, to test potential therapeutics or treatment regimens, etc.

Example 11

Diagnostic Imaging Using CA Specific Antibodies

The present invention encompasses the use of antibodies to cancer-associated polypeptides to accurately stage cancer patients at initial presentation and for early detection of metastatic spread of cancer. Radioimmunoscintigraphy using monoclonal antibodies specific for cancer-associated polypeptides can provide an additional cancer-specific diagnostic test. The monoclonal antibodies of the instant invention are used for histopathological diagnosis of carcinomas.

Subcutaneous human xenografts of cancer cells in nude mice are used to test whether a technetium-99m ($^{99m}$Tc)-labeled monoclonal antibody of the invention can successfully image the xenografted cancer by external gamma scintigraphy as described for seminoma cells by Marks, et al., Brit. J. Urol. 75:225 (1995). Each monoclonal antibody specific for a cancer-associated polypeptide is purified from ascitic fluid of BALB/c mice bearing hybridoma tumors by affinity chromatography on protein A-Sepharose. Purified antibodies, including control monoclonal antibodies such as an avidin-specific monoclonal antibody (Skea, et al., J. Immunol. 151:3557 (1993)) are labeled with $^{99m}$Tc following reduction, using the methods of Mather, et al., J. Nucl. Med. 31:692 (1990) and Zhang et al., Nucl. Med. Biol. 19:607 (1992). Nude mice bearing human cancer cells are injected intraperitoneally with 200-500 µCi of $^{99m}$Tc-labeled antibody. Twenty-four hours after injection, images of the mice are obtained using a Siemens ZLC3700 gamma camera equipped with a 6 mm pinhole collimator set approximately 8 cm from the animal. To determine monoclonal antibody biodistribution following imaging, the normal organs and tumors are removed, weighed, and the radioactivity of the tissues and a sample of the injectate are measured. Additionally, cancer-associated antigen-specific antibodies conjugated to antitumor compounds are used for cancer-specific chemotherapy.

Example 12

Immunohistochemical Methods

Frozen tissue samples from cancer patients were embedded in an optimum cutting temperature (OCT) compound and quick-frozen in isopentane with dry ice. Cryosections were cut with a Leica 3050 CM microtome at thickness of 5 µm and thaw-mounted on vectabound-coated slides. The sections were fixed with ethanol at −20° C. and allowed to air dry overnight at room temperature. The fixed sections were stored at −80° C. until use. For immunohistochemistry, the tissue sections were retrieved and first incubated in blocking buffer (PBS, 5% normal goat serum, 0.1% Tween 20) for 30 minutes at room temperature, and then incubated with the cancer-associated protein-specific monoclonal antibody and control monoclonal antibodies diluted in blocking buffer (1 µg/ml) for 120 minutes. The sections were then washed three times with the blocking buffer. The bound monoclonal antibodies were detected with a goat anti-mouse IgG+IgM (H+L) F(ab')$_2$-peroxidase conjugates and the peroxidase substrate diaminobenzidine (1 mg/ml, Sigma Catalog No. D 5637) in 0.1 M sodium acetate buffer pH 5.05 and 0.003% hydrogen peroxide (Sigma cat. No. H1009). The stained slides were counterstained with hematoxylin and examined under Nikon microscope.

Monoclonal antibody against a cancer-associated protein (antigen) was used to test reactivity with various cell lines from different types of tissues. Cells from different established cell lines were removed from the growth surface without using proteases, packed and embedded in OCT compound. The cells were frozen and sectioned, then stained using a standard IHC protocol. The CellArray™ technology was described in WO 01/43869. Normal tissue (human) obtained by surgical resection were frozen and mounted. Cryosections were cut with a Leica 3050 CM microtome at thickness of 5 µm and thaw-mounted on vectabound-coated slides. The sections were fixed with ethanol at −20° C. and allowed to air dry overnight at room temperature. PolyMICA™ Detection kit was used to determine binding of a cancer-associated-specific monoclonal antibody to normal tissue. Primary monoclonal antibody was used at a final concentration of 1 µg/ml.

Example 13 siRNA Transfections siRNAs for SEMA4D were designed to be complementary to the SEMA4D gene The siRNA oligonucleotides used for SEMA4D are shown in Table 4. siRNA transfections were performed according to the recommendations of the transfection reagent vendor (Invitrogen). The final siRNA concentration used to transfect the cells was 100 nM, unless otherwise noted. In general, cells were grown to 30-50% confluency on the day of transfection (e.g. 5000-20000 cells per well for a 48-well plate).

TABLE 4

Table of siRNA oligonucleotides

| Gene | Sgrs ID | siRNA Name | Target Sequence |
|------|---------|------------|-----------------|
| Sema4D | 38 | HSI0038-2 | AAGTACATGCAGAGCACCACA; SEQ ID NO: 7 |

A mixture of Opti-MEM I (Invitrogen), siRNA oligo, and Plus Reagent (Invitrogen) was prepared as recommended by Invitrogen and incubated at room-temperature for 15-20 minutes. This mix was then combined with an appropriate volume of an Oligofectamine (Invitrogen) reagent in Opti-MEM/siRNA/Plus Reagent mix and incubated for 15 minutes at room-temperature. The cell culture medium was removed from the cell-containing wells and replaced with the appropriate volume of Opti-MEM I. An appropriate volume of siRNA/Oligofectamine mix was added to the cells. The cells were then incubated at 37° C., 5% $CO_2$ for 4 hours followed by addition of growth medium. Day 0 plates were analyzed immediately. For later time-points, the transfection reagent/medium mixture was replaced with fresh cell culture medium and the cells were incubated at 37° C., 5% $CO_2$. The transfection mixture volumes were scaled up or down depending on the tissue culture plate, i.e. 6-, 48-, 96-well plate.

Example 14

RNA Extraction for QPCR Analysis of siRNA Transfected Cells

For conducting QPCR analysis, the RNA is extracted from the transfected cells using an RNAesy 96 Kit (Qiagen) and is performed according to the manufacturer's recommendations. In general, the cells from one well of a 48-well plate are collected, lysed, and the RNA is collected in one well of the 96-well RNAesy plate.

Example 15

Cell Proliferation Assays of siRNA Transfected Cells

Proliferation assays were performed using general assays, such as Cell Titer Glo (Promega) or WST-1 (Roche Applied Science) and were performed according to the manufacturers' recommendations. In general, assays were performed in triplicate. The percent inhibition of proliferation was calculated relative to cells that had been transfected with a scrambled siRNA control oligo.

FIG. 4 shows the effect of silencing SEMA4D expression by using RNAi. Treatment with SEMA4D siRNA for 3-4 days inhibited cell proliferation and induced apoptosis. In FIG. 4A a marginal anti-proliferative effect was observed in OVCAR5 and IGR-OV1 cells transfected with 50 nM siRNA HSI0038-2 while a significant anti-proliferative effect was observed in MDA-MB-231 cells. As shown in FIG. 4B, suppression of proliferation in the MDA-MB-231 cells was associated with increased apoptosis. MDA-MB-231 cells were transfected with control siRNA (top) or SEMA4D siRNA HS10038-2 (bottom) at 50 nM for 72 hours followed by annexin V/7-AAD staining to assess apoptosis. A significant increase in early-stage apoptotic cells (Annexin V+/7-AAD-) was observed in the SEMA4D siRNA treated cells (19.1%) versus control siRNA transfected cells (2.9%). These data indicate that SEMA4D expression is required for cell proliferation and prevention of apoptosis in the cell lines examined.

Figure 5:
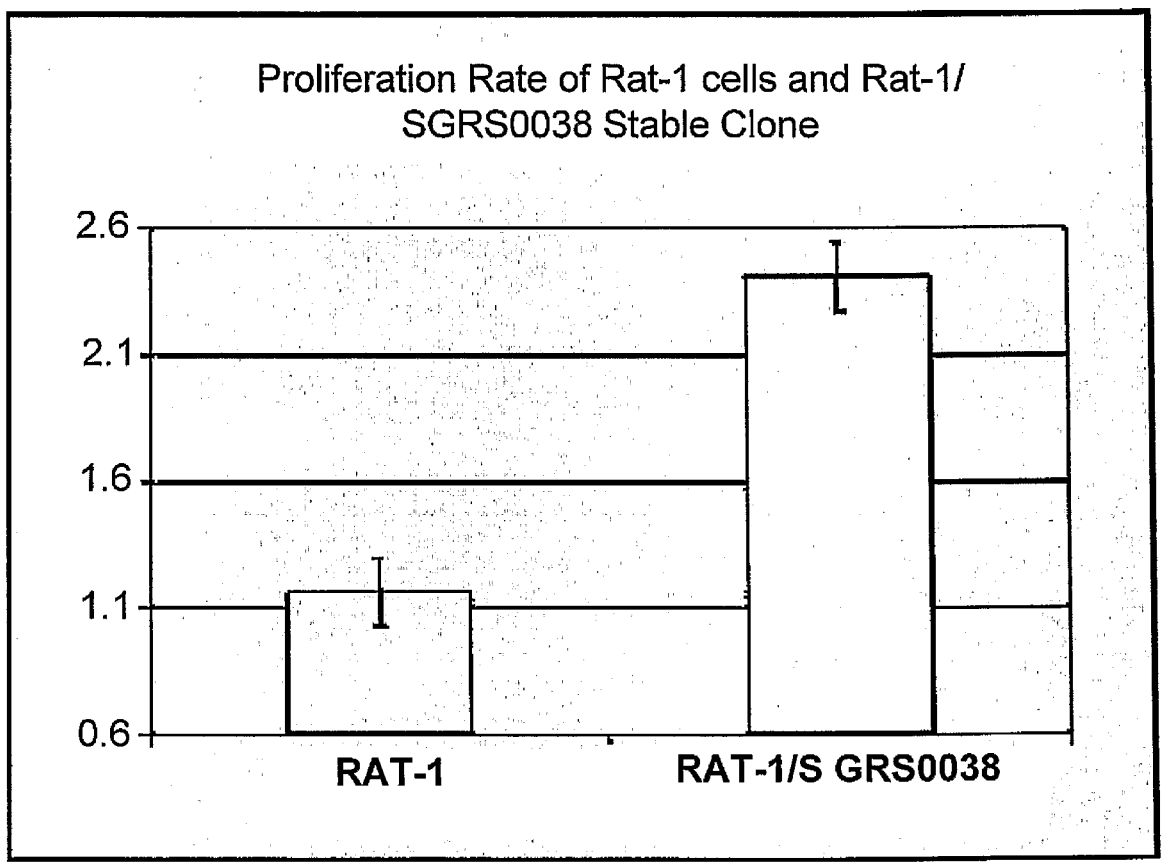
FIG. 5 depicts the results of the WST-1 cell proliferation assay for the Rat-1 cell line, and the Rat-1 cell line transformed with SEMA4D.

The results of the WST-1 assay for SEMA4D si-RNA are shown in FIG. 5. As can be seen, stable transfection of Rat-1 cells with Sema4D (here referred to as SGRS0038) caused a marked increase in proliferation.

Example 16 siRNA inhibition of Cell Migration Assay

Cell migration is measured using the QCM™ fibronectin-coated cell migration assay (Chemicon International INC.) according to the manufacturers' instructions.

Example 17

Rat-I stable cell line generation

Cells were trypsinized, washed once with PBS, resuspended in cell culture medium [DMEM(containing glutamine)+10% FBS (fetal bovine serum)], and $2\times10^6$ cells per well were seeded into 6-well culture plates in a total volume of 2 mls. Plasmid DNA (2 μg) was mixed with 100 μl serum-free medium, followed by addition of 10 μl of Superfect transfection reagent (Qiagen), vortexed for 10 seconds and incubated at room-temperature for 10 minutes. While the complex was forming, the cells were washed twice with PBS. 600 ul DMEM+10% FBS was then added to the complex, mixed, transferred to the cell-containing well, and incubated for 4 hours at 37° C. Then 2 mls DMEM+10% FBS was added followed by a 48 hr incubation at 37° C., 5% $CO_2$.

The cells were then trypsinized, resuspended with 1 ml DMEM+10% FBS+800 ug/ml G418 and seeded at different densities (1:10, 1:20 up to 1:100) in 10-cm dishes. The dishes were incubated at 37° C., 5% $CO_2$ until G418-resistant colonies formed, after which individual clones were picked and transferred to a 24-well dish containing 1 ml DMEM+10% FBS+800 ug/ml G418.

The cloned cells were expanded further and screened for the presence of the plasmid-expressed gene product, generally by western blot analysis.

Example 18

Soft Agar Transformation Assay

A 0.7% and 1% low temperature melting agarose (DNA grade, J. T. Baker) solution was prepared in sterile water, heated to boiling, and cooled to 40° C. in a waterbath. A 2×DMEM solution was prepared by mixing 10× powdered DMEM (Invitrogen) in water, mixing, followed by addition of 3.7 g of $NaHCO_3$ per liter volume, followed by addition of FBS to 20%. 0.75 ml of the culture medium (pre-warmed to 40° C.) was mixed with 0.75 ml of the 1% agarose solution and the final 1.5 ml 0.5% agarose solution was added per well to a 6-well dish. NIH-3T3 transiently-transfected SEMA4D-expressing cells or NIH-3T3 vector control cells were trypsinized, washed twiced with PBS, and diluted to 50000 cells per ml 1×DMEM+10% FBS. 0.1 ml of this cell suspension was mixed gently with 1 ml 2×DMEM+20% FBS and 1 ml 0.7% agarose solution and the final 1.5 ml suspension was added to the 6-well dish containing the solidified 0.5% agar. These agar plates were placed at 37° C., 5% $CO_2$ in a humidified incubator for 10-14 days and the cells were re-feed fresh 1×DMEM+10% FBS every 3-4 days.

The results of the soft agar transformation show a loss of anchorage dependence in cells transiently transfected with a SEMA4D-expression vector.

Example 19

Mouse Tumorgenicity Assays

Rat 1 stable cell lines were grown in two T150 flasks to 70-80% confluency. The cells were trypsinized, washed twice in PBS, and resuspended with PBS to $10^7$, $10^6$, and $10^5$ cells/ml. The cell suspension was kept on ice until injection into mice. Female NOD.CB17-Prkdc<scid>/J mice, 3-5 weeks of age were obtained from JAX West's M-3 facility (UC Davis) and housed 4 per cage in an isolator unit at JAX West's West Sacramento facility. Using a 25 gauge needle, mice were injected with 0.1 ml cell suspension subcutaneously in the thoracic region (2 sites per mouse). Once a tumor began to form, tumor growth was measured twice per week using a caliper. The tumor was measured in two directions, rostral-caudal and medial-lateral. Measurements were recorded as width×length and the tumor volume was calculated using the conversion formula (length×width2)/2.

Figure 6:
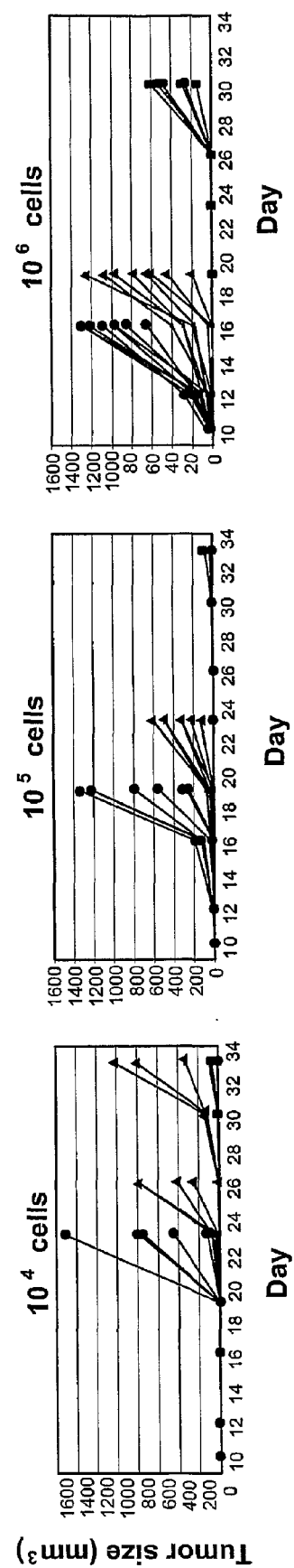
FIG. 6 depicts the results of tumorigenicity assays for SEMA4D.

FIG. 6 shows the results of the tumorigenicity assay for SEMA4D. The code SGRS038 represents cells that have been transformed with the gene coding for SEMA4D. It can be seen that the in vivo tumour growth is markedly increased relative to control in cells transformed with the gene coding for SEMA4D. Furthermore, the tumorigenicity assays confirm that this gene is an oncogene.

Example 20

Testing of SEMA4D Hybridomas by Flow Cytometry

Cell titer was determined using a hemocytometer. An appropriate volume of cells was transferred to one or two 15 ml conical tube. The cells were pelleted in the Eppendorf clinical centrifuge at 1100 rpm, 5 min, RT or 4° C. Most of the medium was aspirated, avoiding the pellet. The pellet was resuspended in the residual medium by tapping tube. Cold Staining Buffer (PBS, 2% BSA, 0.05% sodium azide) was added to the tube(s) to a final volume of $5\times10^5$ cells/ml. The cells were transferred to a sterile pipetting reservoir. Using a multi-channel pipette, 100 μl was aliquoted into each well. The plate(s) were cooled on ice for 10 minutes. The cells were then pelleted by spinning the plate in an Eppendorf clinical centrifuge at 3000 rpm, 3 min, RT. The supernatant was discarded and the inverted plate was dabbed onto kim-wipe to remove the excess supernatant. Using a multi-channel pipette, 50 μl hybridoma mAb supernatants or control antibody mix/supernatants was transferred from a column on the master plate into the corresponding column of the cell plates. The cells were resuspended by pipetting several times. The plate was then cooled on ice for 30 min. Cold Wash Buffer (PBS with 0.05% sodium azide) was dispensed into a fresh pipetting reservoir (~20 ml per plate). Using an 8-channel pipette, 200 μl was aliquoted into each well. The cells were pelleted and wash buffer was removed. Two washes were carried out. Using a multi-channel pipette, 50 μl of the secondary antibody mix was transferred column by column across the plate; i.e. 3 μl goat (Fab'2) anti-mouse IgG-PE per well. The plate was incubated on ice for 30 min in the dark. The cells were then washed twice and incubated on ice for 30 min in the dark. The plate was read on a Guava-PCA instrument according to the manufacturers' instructions.

Figure 7:
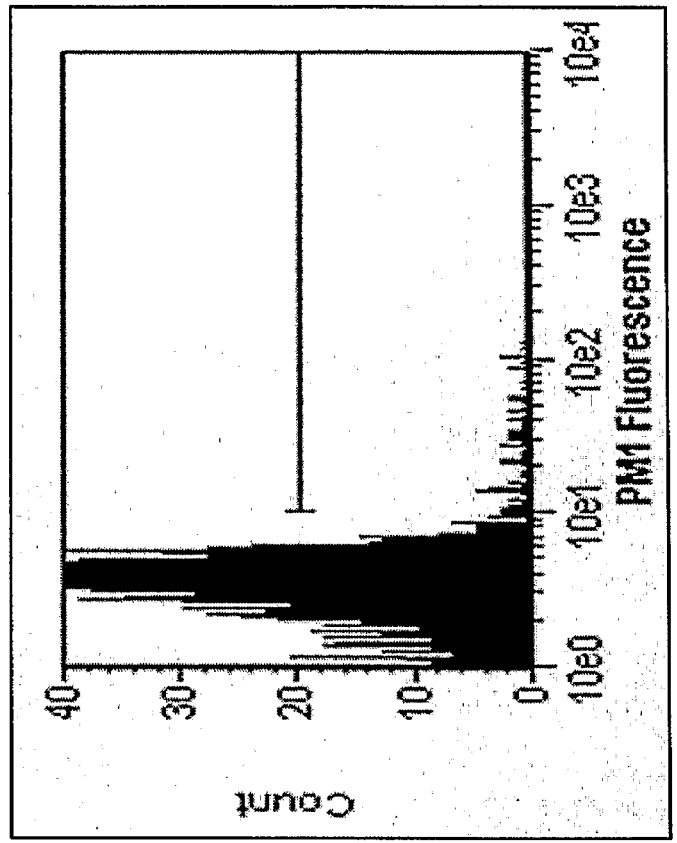
FIG. 7 depicts flow cytometry results using the anti-SEMA4D monoclonal antibody and demonstrates validation of the B098 monoclonal antibody for the detection of SEMA4D.
Figure 7:
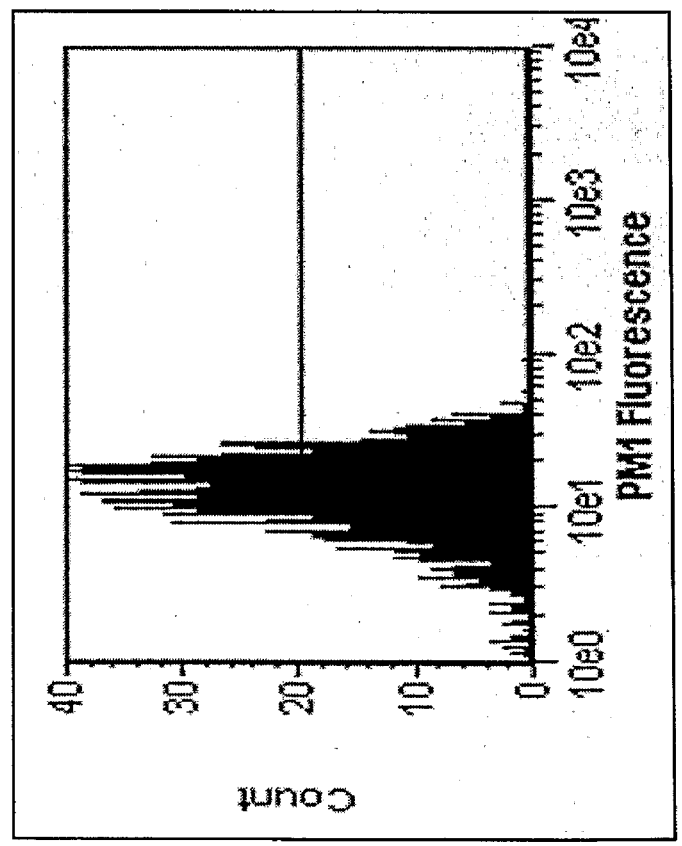

Flow cytometry results using the anti-SEMA4D monoclonal antibody are shown in FIG. 7 and demonstrate validation of the B098 monoclonal antibody for the detection of SEMA4D.

Example 21

Testing of SEMA4D Hybridomas by Immunofluorescence

Jurkat and K562 cells were cultured in RPMI-1640 (with L-glutamine) and 10% FBS 24 hours before the staining. The cells were collected, washed once with PBS, and counted. 50,000 cells were dispensed per eppendorf tube. The cells were pelleted at 3,000×rpm for 5 min. To stain cells, 50 µl SEMA4D hybridoma supernatant was added to one eppendorf tube and 50 µl PBS was added to the control. The tubes were incubated at room temperature for 30 minutes. The cells were then washed twice with 1 ml PBS. The cells were pelleted at 3,000×rpm for 5 minutes and fixed in 4% formaldehyde (diluted in PBS) for 10 minutes at room temperature. The fixed cells were then washed twice with 1 ml PBS. The washed cells were pelleted at 3,000×rpm for 5 minutes. 25 µl anti-mouse-Cy3 conjugated antibody diluted in PBS (1:200) was added to each tube and the tubes were incubated 20 minutes at room temperature. The cells were then washed cells twice with 1 ml PBS and pelleted cells at 3,000×rpm for 5 minutes. The supernatant was discarded. 10 µl PBS was added to each tube and the cells were resuspended. 1 drop (about 15 µl) of Vectashield with DAPI was dispensed on a glass slide. 5 µl of resuspended cells was added to the Vectashield and mixed. A coverslip was placed on the top of the micro-slide. The cells were observed under a fluorescence microscope using DAPI and Cy3 channels.

Staining of breast cancer samples was primarily in nerves and lymphocytes. No significant staining was observed in the epithelial cells present. All 8 specimens examined exhibit analogous staining patterns. Staining of ovarian cancer revealed 1 of 8 specimens exhibition light cytoplasm and membranous staining. A specimen with high gene expression showed staining primarily of lymphocytes. Other tumor types examined including bladder, colon, kidney, liver, lung, pancreas, prostate, and skin) exhibited localized expression in the lymphocytes. Lymphoma samples examined, 3 of 5 lymphomas examined exhibited staining in B-cells and anaplastic lymphomas. In normal tissues, kidney stained in both the proximal and distal tubules. Strong Immunoreactivity was observed in one normal spleen specimen, localized to the splenic nodules (white pulp). The only significant staining observed in the other tissues were scattered infiltrates and nerve endings.

Immunofluorescence of live cells expressing tagged SEMA4D using the monoclonal anti-SEMA4D antibody and an antibody to the tag on SEMA4D demonstrated that the monoclonal antibody specifically detects SEMA4D. The monoclonal antibody also stained via immunofluorescence a SEMA4D-positive cell line (Jurkat) while failing to stain a negative control cell line (K-562).

Example 22

Apoptosis Protocol

Cells were transfected with the appropriate siRNA oligonucleotide according to the siRNA transfection protocol. At the desired time, cells were collected and stained with Annexin V-PE and 7-AAD using the reagents and instructions from the Guava Technologies' Guava Nexin Kit. Flow cytometry, data acquisition and analysis were performed using a Guava-PCA (Guava Technologies) and analysis software.

The results of the apoptosis assay are shown in FIG. 4B.

Example 23

Expression Data

Table 6 shows the expression level of SEMA4D in a range of tumor tissues. The results of three forms of expression assay are shown in the table. Results with the notation U133A&B (see Array Type column) indicate that an Affymetrix oligonucleotide based expression array was used (worldwide web site: affymetrix.com/support/technical/byproduct.affx?product=hg-u133-plus) results with the notation Chiron cDNA array were produced using a Chiron in house spotted cDNA array. The remaining results were produced using the Affymetrix U133 plus 2 oligo array (worldwide web site: affymetrix.com/support/technical/byproduct.affx?product=hg-ul 33-plus).

Tissue samples for the first two array formats were collected using laser capture microdissection (LCD) (see definition below). Tissue samples for the third form of array (U133 plus 2) were collected using standard manual dissection procedures.

The level of differential expression was assessed by separate methods for each array type. The results for U133A&B and EVD arrays are expressed as the number of samples that had an expression level either above or below a defined threshold. The notation "2×concordance" or "0.5× Concordance" indicates that a number of the samples (shown in the column % samples showing diff level of expression) had either a 2× greater level of expression than the control values or a level of expression less than half that of the control average. Thus showing either over or under-expression of the gene (at a significance level of "t"<=0.001).

The expression levels for the U133+2 arrays are expressed as 80-50 or 80-80 percentile ratios. All results shown have passed a t test for significance at the 0.001% level. In an 80-50 Percentile Ratio result 20% of the tumor samples have a greater the 2 fold level of overexpression when compared to 50% of the control samples. In an 80-80 percentile ratio result 20% of the tumor samples have a greater than 3 fold level of overexpression as compared to 80% of the control samples.
Selection of Tumor Associated Antigens for targeting
Laser dissection of tumorous cells and adjacent normals and production of RNA from dissected cells.

Normal and cancerous tissues were collected from patients using laser capture microdissection (LCM), and RNA was prepared from these tissues, using techniques which are well known in the art (see, e.g., Ohyama et al. (2000) Biotech'iques 29:530-6; Curran et al. (2000) Mol. Pathol. 53:64-8; Suarez-Quian et al. (1999) Biotech'iques 26:328-35; Simone et al. (1998) Trends Gerzet 14:272-6; Conia et al. (1997) J. Clin. Lab. Anal. 11:28-38; Emmert-Buck et al. (1996) Science 274:998-1001). Because LCM provides for the isolation of specific cell types to provide a substantially homogenous cell sample, this provided for a similarly pure RNA sample.
Microarray Analysis Production of cDNA: Total RNA produced from the dissected cells was then used to produce cDNA using an Affymetrix Two-cycle cDNA Synthesis Kit (cat#900432). 8 µL of total RNA was used with 1 µL T7-(dT) 24 primer (50 pmol/µL) in an 11 µL reaction which was heated to 70° C. for 12 minutes. The mixture was then cooled to room temperature for five minutes. 9 µL master mix (4 µL 5×1st strand cDNA buffer, 2 µL 0.1 M DTT, 1 µL 10 mM dNTP mix, 2 µL Superscript II (600 U/µL)) was added and the mixture was incubated for 2.5 hours at 42° C. (total volume of the mixture was 20 µL). Following cooling on ice, the 2nd strand synthesis was completed as follows: 20 µL mixture from above was mixed with 130 µL second strand master mix (91 µL water, 30 µL 5× Second Strand Reaction Buffer, 3 µL 10 mM dNTP mix, 1 µL 10 U/µL *e. coli* DNA ligase, 4 µL 10 U/µL *E. coli* DNA polymerase I, 1 µL 2 U/µL *e. coli* Rnase H) and was incubated for 2 hours at 16° C. for 10 minutes. Following cooling on ice, the dsDNA was purified from the reaction mixture. Briefly, a QiaQuick PCT Purification Kit was used (Qiagen, cat#28104), and 5 volumes of buffer PB was added to 1 volume of the cDNA mixture. The cDNA was then purified on a QIAquick spin column according to manufacture's directions, yielding a final volume of 60 µL.

Production of biotin-labeled cRNA. The cDNA produced and purified above was then used to make biotin labeled RNA as follows: The 60 µL of cDNA recovered from the QIAQuick column was reduced to a volume of 22 µL in a medium heated speed vacuum. This was then used with an ENZO BioArray High Yield RNA Transcription Kit (cat#4265520). Briefly, a master mix containing 4 µL 10×HY Reaction buffer, 4 µL 10× Biotin-Labeled Ribonucleotides, 4 µL DTT, 4 µL Rnase Inhibitor Mix, and 2 µL T7 RNA Polymerase was added to the 22 µL of purified cDNA, and left tp incubate at 37° C. for 4 to 6 hours. The reaction was then purified using a Qiagen RNeasy Kit (cat#74104) according to manufacturer's directions.

Fragmentation of cRNA. 15 to 20 µg of cRNA from above was mixed with 8 µL of 5× Fragmentation Buffer (200 mM Tris-acetate, pH 8.1, 500 mM Potassium acetate, 150 mM Magnesium acetate) and water to a final volume of 40 µL. The mixture was incubated at 94° C. for 35 minutes. Typically, this fragmentation protocol yields a distribution of RNA fragments that range in size from 35 to 200 bases. Fragmentation was confirmed using TAE agarose electrophoresis.

Array Hybridization. The fragmented cRNA from above was then used to make a hybridization cocktail. Briefly, the 40 µL from above was mixed with 1 mg/mL human Cot DNA and a suitable control oligonucleotide. Additionally, 3 mg of Herring Sperm DNA (10 mg/mL) was added along with 150 µL 2× Hybridization buffer (100 mM MES, 1 M NaCl, 20 mM EDTA, 0.01% Tween-20) and water to a final volume of 300 µL. 200 µL of this solution was then loaded onto the U133 array (Affymetrix cat #900370) and incubated at 45° C. with a constant speed of 45 rpm overnight. The hybridization buffer was then removed and the array was washed and stained with 200 µL Non-stringent wash buffer (6×SSPE, 0.01% Tween-20) and using a GeneChip Fluidics Station 450 (Affymetrix, cat#00-0079) according to manufacturer's protocol.

Scanning array. The array from above was then scanned using a GeneChip Scanner 3000 (Affymetrix cat#00-0217) according to manufacturer's protocol.

Selection of potential tumor cell antigen targets. The tumor antigens were selected for targeting by comparison of the expression level of the antigen in the tumor cells (either primary tumors or metastases) versus neighboring healthy tissue or with pooled normal tissue. Tumor antigens selected showed at least a 3 fold (300%) increased expression relative to surrounding normal tissue, where this 3 fold increase is seen in comparison with a majority of pooled, commercially available normal tissue samples (Reference standard mix or RSM, pools are made for each tissue type). The tables below present the fold increase data from the array analysis for the respective genes, where the numbers represent the percent of patient samples analyzed that showed a 2-, 3- or 5-fold increase in expression in comparison to normal tissues.

TABLE 6

| Gene Symbol | Array Type | Tumour Type and Control Notation | Result Type | Avg No of Tissue Samples | SDev of Sample No | % samples showing diff level of expression | SDev of Fold or % diff. | No of Replicate Experiments |
| --- | --- | --- | --- | --- | --- | --- | --- | --- |
| SEMA4D | Chiron cDNA array | Colon Cancer | 2X Concordance | 75.0 | 0.0 | 48.5 | 0.7 | 2.0 |
| SEMA4D | Chiron cDNA array | Colon metastasis | 2X Concordance | 33.0 | 0.0 | 22.5 | 2.1 | 2.0 |
| SEMA4D | Chiron cDNA array | matched Colon Cancer | 2X Concordance | 36.0 | 0.0 | 50.0 | 0.0 | 2.0 |
| SEMA4D | Chiron cDNA array | matched Colon Cancer metastasis | 2X Concordance | 35.0 | 0.0 | 41.5 | 6.4 | 2.0 |
| SEMA4D | U133A & B | Colon Cancer | 2X Concordance | 26.0 | | 35.0 | | 1.0 |
| SEMA4D | U133A & B | Colon metastasis | 2X Concordance | 33.0 | | 30.0 | | 1.0 |
| SEMA4D | U133A & B | Prostate Cancer | <=0.5X Concordance | 22.0 | | 23.0 | | 1.0 |

| Gene Symbol | Array Type | Tumour Type and Control Notation | Result Type | Avg No of Tissue Samples | SDev of Sample No | Fold Diff from normal | SDev of Fold or % diff. | No of Replicate Experiments |
| --- | --- | --- | --- | --- | --- | --- | --- | --- |
| SEMA4D | U133A & B | Blood/Lymph Carcinoma All Vs Essential Normal | 80-50 Percentile Ratio | 60.0 | | 4.0 | | 1.0 |

Example 24

Sequences

```
SEQ ID NO: 1; accession number NM_006378:
gctgtaacactcaccgtgaaggtctgcagcttcactcccgagccagcgag accacgaacccaccagaaggaagaaactctgaacacatctgaacatcaga agggacagactccagacgcgccaccactctgctaacaccagatagtggaa agaaaccatgtgctgaaatgtttgacgacactgatggtttgactctgcta actgaatggcttattgtgcaagaaagtacacctggtcgggtcctggggc tcatctctagcaccagcaaagatttctgaagacgtctttctagaaatgac tggaaagtttcaagaggcataagatacagcatttcttctgaggccctgaa gaagtatcaagtgggctttgacattgcggtggtgagagcgacccctcctc acctggagaactgggaaatgtggattctcaggaccgcgctgttcacgag ctccaggctgtgctgctggccctggtcctggggcgctgagccgcatctgc aatagcacacttgcccggccacctgctgccgtgagcctttgctgctgaag cccctggggtcgcctctacctgatgaggatgtgcaccccattagggggc tgctcatggcccttgcagtgatgtttgggacagcgatggcatttgcaccc ataccccggatcacctgggagcacagagaggtgcacctggtgcagtttca tgagccagacatctacaactactcagccttgctgctgagcgaggacaagg acaccttgtacataggtgcccggggaggcggtcttcgctgtgaacgcactc aacatctccgagaagcagcatgaggtgtattggaaggtctcagaagacaa aaaagcaaaatgtgcagaaaagggaaatcaaaacagacagagtgcctca actacatccgggtgctgcagccactcagcgccacttcccttttacgtgtgt gggaccaacgcattccagccggcctgtgaccacctgaacttaacatcctt taagtttctggggaaaaatgaagatggcaaaggaagatgtcccctttgacc cagcacacagctacacatccgtcatggttgatggagaactttattcgggg acgtcgtataatttttgggaagtgaacccatcatctcccgaaattcttc ccacagtcctctgaggacagaatatgcaatccccttggctgaacgagccta gtttcgtgtttgctgacgtgatccgaaaaagcccagacagccccgacggc gaggatgacagggtctacttcttcttcacggaggtgtctgtggagtatga gtttgtgttcagggtgctgatcccacggatagcaagagtgtgcaaggggg accagggcggcctgaggaccttgcagaagaaatggacctccttcctgaaa gcccgactcatctgctcccggccagacagcggcttggtcttcaatgtgct gcgggatgtcttcgtgctcaggtccccgggcctgaaggtgcctgtgttct atgcactcttcaccccacagctgaacaacgtggggctgtcggcagtgtgc gcctacaacctgtccacagccgaggaggtcttctcccacgggaagtacat gcagagcaccacagtggagcagtcccacaccaagtgggtgcgctataatg gcccggtacccaagccgcggcctggagcgtgcatcgacagcgaggcacgg gccgccaactacaccagctcctgaatttgccagacaagacgctgcagtt cgttaaagaccacccttgatggatgactcggtaaccccaatagacaaca ggcccaggttaatcaagaaagatgtgaactacacccagatcgtggtggac cggacccaggccctggatgggactgtctatgatgtcatgtttgtcagcac agaccggggagctctgcacaaagccatcagcctcgagcacgctgttcaca tcatcgaggagacccagctcttccaggactttgagccagtccagaccctg ctgctgtcttcaaagaagggcaacaggtttgtctatgctggctctaactc gggcgtggtccaggccccgctggccttctgtgggaagcacggcacctgcg aggactgtgtgctggcgcgggaccccactgcgcctggagcccgcccaca gcgacctgcgtggctctgcaccagaccgagagccccagcaggggtttgat tcaggagatgagcggcgatgcttctgtgtgcccggataaaagtaaaggaa gttaccggcagcatttttttcaagcacggtggcacagcggaactgaaatgc tcccaaaaatccaacctggcccgggtctctttggaagttccagaatgacgt gttgaaggccgagagccccaagtacggtcttatgggcagaaaaaacttgc tcatcttcaacttgtcagaaggagacagtggggtgtaccagtgcctgtca gaggagagggttaagaacaaaacggtcttccaagtggtcgcaagcacgt cctggaagtgaaggtggttccaaagcccgtagtggccccaccttgtcag ttgttcagacagaaggtagtaggattgccaccaaagtgttggtggcatcc acccaagggtcttctcccccaaccccagccgtgcaggccacctcctccgg ggccatcacccttcctcccaagcctgcgcccaccggcacatcctgcgaac caaagatcgtcatcaacacggtccccagctccactcggagaaaaccatg tatcttaagtccagcgacaaccgcctcctcatgtccctcttcctcttctt ctttgttctcttcctctgcctctttttctacaactgctataagggatacc tgcccagacagtgcttgaaattccgctcggccctactaattgggaagaag aagcccaagtcagatttctgtgaccgtgagcagagcctgaaggagacgtt agtagagccagggagcttctcccagcagaatggggagcaccccaagccag ccctggacaccggctatgagaccgagcaagacaccatcaccagcaaagtc cccacggatagggaggactcacagaggatcgacgaccttctgccaggga caagccctttgacgtcaagtgtgagctgaagttcgctgactcagacgcag atggagactgaggccggctgtgcatcccgctggtgcctcggctgcgacg tgtccaggcgtggagagttttgtgtttctcctgttcagtatccgagtctc gtgcagtgctgcgtaggttagcccgcatcgtgcagacaacctcagtcctc ttgtctattttctcttgggttgagcctgtgacttggtttctctttgtcct tttggaaaatgacaatccttgcatcccagtcttgtgttccgaagtcagt cggagtacttgaagaaggcccacgggcggcacggagttcctgagcccttt ctgtagtggggaaaggtggctggacctctgttggctgagaagagcatcc cttcagcttcccctccccgtagcagccactaaaagattatttaattccag attggaaatgacatttttagtttatcagattggtaacttatcgcctgttgt ccagattggcacgaaccttttcttccacttaattatttttttaggatttt gctttgattgtgtttatgtcatgggtcattttttttagttacagaagca gatgtgttaatatttagaagaagatgtatatcttccagattttgttatat atttggcataaaatacggcttacgttgcttaagattctcagggataaact tccttttgctaaatgcattctttctgcttttagaaatgtagacataaaca ctccccggagcccactcacctttttttcttttttctttttttttttttaact
```

```
ttattccttgagggaagcattgttttggagagattttctttctgtactt
cgttttacttttcttttttttaacttttactctctcgaagaagaggacc
ttcccacatccacgaggtgggttttgagcaagggaaggtagcctggatga
gctgagtggagccaggctggcccagagctgagatgggagtgcggtacaat
ctggagcccacagctgtcggtcagaacctcctgtgagacagatggaacct
tcacaagggcgcctttggttctctgaacatctcctttctcttcttgcttc
aattgcatacccactgcctgcccagactttctatccagcctcactgagct
gcccactactggaagggaactgggcctcggtggccggggccgcgagctgt
gaccacagcaccctcaagcatacggcgctgttcctgccactgtcctgaag
atgtgaatgggtggtacgatttcaacactggttaatttcacactccatct
ccccgctttgtaaatacccatcgggaagagactttttttccatggtgaag
agcaataaactctggatgtttgtgcgcgtgtgtgacagtcttatcttcc
agcatgataggatttgaccattttggtgtaaacatttgtgttttataaga
tttaccttgttttattttctactttgaattgtatacatttggaaagta
cccaaataaatgagaagcttctatccttaaaaaaaaaaaaaaaaaaaa
aaaaaaaaaaaaaaaaaaaaaaa
SEQ ID NO: 2; accession number NP_006369:
mrmctpirgllmalavmfgtamafapipritwehrevhlvqfhepdiyny
salllsedkdtlyigareavfavnalnisekqhevywkvsedkkakcaek
gkskqteclnyirvlqplsatslyvcgtnafqpacdhlnltsfkflgkne
dgkgrcpfdpahsytsvmvdgelysgtsynflgsepiisrnsshsplrte
yaipwlnepsfvfadvirkspdspdgeddrvyffftevsveyefvfrvli
priarvckgdqgglrtlqkkwtsflkarlicsrpdsglvfnvlrdvfvlr
spglkvpvfyalftpqlnnvglsavcaynlstaeevfshgkymqstt veq
shtkwvryngpvpkprpgacidsearaanytsslnlpdktlqfvkdhplm
ddsvtpidnrprllikkdvnytqivvdrtqaldgtvydvmfvstdrgalhk
aislehavhiieetqlfqdfepvqtlllsskkgnrfvyagsnsgvvqapl
afcgkhgtcedcvlardpycawspptatcvalhqtespsrgliqemsgda
svcpdkskgsyrqhffkhggtaelkcsqksnlarvfwkfqndvlkaespk
yglmgrknllifnlsegdsgvyqclseervknktvfqvvakhvlevkvvp
kpvvaptlsvvqtegsriatkvlvastqgssppt pavqatssgaitlppk
paptgtscepkivintvpqlhsektmylkssdnrllmslflffffvlflcl
ffyncykgylprqclktrsalligkkkpksdfcdreqslketlvepgsfs
qqngehpkpaldtgyeteqdtitskvptdredsgqriddlsardkpfdvk
celkfadsdadgd
SEQ ID NO: 3; accession number BC054500
(SEQ ID NO: 3 = nucleotide sequence):
gctgtaacactcaccgtgaaggtctgcagcttcactcccgagccagcgag
accacgaacccaccagaaggaagaaactctgaacacatctgaacatcaga
agggacagactccagacgcgccaccactctgctaacaccagatagtggaa
agaaaccatgtgctgaaatgtttgacgacactgatgtttgactctgcta
actggaatggcttattgtgcaagaaagtacacctggtcgggtcctgggc
tcatctctagcaccagcaaagatttctgaagacgtctttctagaaatgac
tggaaagtttcaagaggcataagatacagcatttcttctgaggccctgaa
gaagtatcaagtgggctttgacattgcggtggtgagagcgacccctcctc
acctggagaactgggaaatgtggattctcagggaccgcgctgttcacgag
ctccaggctgtgctgctggccctggtcctggggcgctgagccgcatctgc
aatagcacacttgcccggccacctgctgccgtgagcctttgctgctgaag
cccctggggtcgcctctacctgatgaggatgtgcaccccattagggggc
tgctcatggcccttgcagtgatgtttgggacagcgatggcatttgcaccc
ataccccggatcacctgggagcacagagaggtgcacctggtgcagtttca
tgagccagacatctacaactactcagccttgctgctgagcgaggacaagg
acacttgtacataggtgcccgggaggcggtcttcgctgtgaacgcactc
aacatctccgagaagcagcatgaggtgtattggaaggtctcagaagacaa
aaaagcaaaatgtgcagaaaaggggaaatcaaaacagagtgcctca
actacatccgggtgctgcagccactcagcgccacttcccttacgtgtgt
gggaccaacgcattccagccggcctgtgaccacctgaacttaacatcctt
taagttctggggaaaaatgaagatggcaaaggaagatgtcccttt gacc
cagcacacagctacacatccgtcatggttgatggagaactttattcgggg
acgtcgtataattttttgggaagtgaacccatcatctcccgaaattcttc
ccacagtcctctgaggacagaatatgcaatccctggctgaacgagccta
gtttcgtgtttgctgacgtgatccgaaaaagcccagacagccccgacggc
gaggatgacagggtctacttcttcttcacggaggtgtctgtggagtatga
gtttgtgttcagggtgctgatcccacggatagcaagagtgtgcaagggg
accagggcggcctgaggaccttgcagaagaaatggacctccttcctgaaa
gcccgactcatctgctcccggccagacagcggcttggtcttcaatgtgct
gcgggatgtcttcgtgctcaggtccccgggcctgaaggtgcctgtgttct
atgcactcttcaccccacagctgaacaacgtggggctgtcggcagtgtgc
gcctacaacctgtccacagccgaggaggtcttctcccacgggaagtacat
gcagagcaccacagtggagcagtcccacaccaagtgggtgcgctataatg
gcccggtacccaagccgcggcctggagcgtgcatcgacagcgaggcacgg
ccgccaactacaccagctccttgaatttgccagacaagacgctgcagtt
cgttaaagaccacccttt gatggatgactcggtaaccccaatagcaaca
ggcccaggttaatcaagaaagatgtgaactacacccagatcgtggtggac
cggacccaggccctggatgggactgtctatgatgtcatgtttgtcagcac
agaccggggagctctgcacaaagccatcagcctcgagcacgctgttcaca
tcatcgaggagacccagctcttccaggactttgagccagtccagaccctg
ctgctgtcttcaaagaagggcaacaggtttgtctatgctggctctaactc
gggcgtggtccaggccccgctggccttctgtgggaagcacggcacctgcg
aggactgtgtgctggcgcgggacccctactgcgcctggagcccgcccaca
gcgacctgcgtggctctgcaccagaccgagagcccagcaggggtttgat
tcaggagatgagcggcgatgcttctgtgtgcccggataaaagtaaaggaa
```

-continued

```
gttaccggcagcattttttcaagcacggtggcacagcggaactgaaatgc
tcccaaaaatccaacctggcccgggtcttttggaagttccagaatgacgt
gttgaaggccgagagccccaagtacggtcttatgggcagaaaaaacttgc
tcatcttcaacttgtcagaaggagacagtggggtgtaccagtgcctgtca
gaggagagggttaagaacaaaacggtcttccaagtggtcgccaagcacgt
cctggaagtgaaggtggttccaaagcccgtagtggccccccaccttgtcag
ttgttcagacagaaggtagtaggattgccaccaaagtgttggtggcatcc
acccaagggtcttctcccccaaccccagccgtgcaggccacctcctccgg
ggccatcacccttcctcccaagcctgcgcccaccggcacatcctgcgaac
caaagatcgtcatcaacacggtccccagctccaotcggagaaaaccatg
tatcttaagtccagcgacaaccgcctcctcatgtcccctcttcctcttcct
cttgttctcttcctctgcctctttttctacaactgctataagggatacc
tgcccagacagtgcttgaaattccgctcggccctactaattgggaagaag
aagcccaagtcagatttctgtgaccgagcagagcctgaaggagacgtt
agtagagccaggagcttctcccagcagaatggggagcaccccaagccag
ccctggacaccggctatgagaccgagcaagacaccatcaccagcaaagtc
cccacggataggaggactcacagaggatcgacgacctttctgccaggga
caagcccttgacgtcaagtgtgagctgaagttcgctgactcagacgcag
atggagactgaggccggctgtgcatccccgctggtgcctcggctgcgacg
tgtccaggcgtggagagttttgtgtttctcctgttcagtatccgagtctc
gtgcagtgctgcgtaggttagcccgcatcgtgcagacaacctcagtcctc
ttgtctattttctcttgggttgagcctgtgacttggtttctctttgtcct
tttgaaaaatgacaatccttgcatcccagtcttgtgttccgaagtcagt
cggagtacttgaagaaggcccacgggcggcacggagttcctgagcccttt
ctgtagtgggggaaaggtggctggacctctgttggctgagaagagcatcc
cttcagcttcccctccccgtagcagccactaaaagattatttaattccag
attggaaatgacattttagtttatcagattggtaacttatcgcctgttgt
ccagattggcacgaacctttcttccacttaattattttttttaggatttt
gctttgattgtgtttatgtcatgggtcattttttttagttacagaagca
gatgtgttaatatttagaagaagatgtatatcttccagattttgttatat
atttggcataaaatacggcttacgttgcttaagattctcagggataaact
tccttttgctaaatgcattcttttctgctttagaaatgtagacataaaca
ctccccggagcccactcaccttttttctttttcttttttttttttaact
ttattccttgagggaagcattgttttggagagattttctttctgtactt
cgttttacttttctttttttttaacttttactctctcgaagaagaggacc
ttcccacatccacgaggtgggttttgagcaagggaaggtagcctggatga
gctgagtggagccaggctggcccagagctgagatggagtgcggtacaat
ctggagcccacagctgtcggtcagaacctcctgtgagacagatggaacct
tcacaagggcgcctttggttctctgaacatctccttttctcttcttgcttc
aattgcatacccactgcctgcccagactttctatccagcctcactgagct
gcccactactggaagggaactgggcctcggtggccggggccgcgagctgt
```

-continued

```
gaccacagcaccctcaagcatacggcgctgttcctgccactgtcctgaag
atgtgaatgggtggtacgatttcaacactggttaatttcacactccatct
ccccgctttgtaaatacccatcgggaagagactttttttccatggtgaag
agcaataaactctggatgtttgtgcgcgtgtgtggacagtcttatcttcc
agcatgataggatttgaccattttggtgtaaacatttgtgttttataaga
tttaccttgttttatttttctactttgaattgtatacatttggaaagta
cccaaataaatgagaagcttctatccttaaaaaaaaaaaaaaaaaaaaa
aaaaaaaaaaaaaaaaaaaaaaaa
```

SEQ ID NO: 4; accession number BC054500
(SEQ ID NO: 4 = amino acid sequence):
mrmctpirgllmalavmfgtamafapipritwehrevhlvqfhepdiyny
sallsedkdtlyigareavfavnalnisekqhevywkvsedkkakcaek
gkskqteclnyirvlqplsatslyvcgtnafqpacdhlnltsfkflgkne
dgkgrcpfdpahsytsvmvdgelysgtsynflgsepiisrnsshsplrte
yaipwlnepsfvfadvirkspdspdgeddrvyffftevsveyefvfrvli
priarvckgdqgglrtlqkkwtsflkarlicsrpdsglvfnvlrdvfvlr
spglkvpvfyalftpqlnnvglsavcaynlstaeevfshgkymqsttveq
shtkwvryngpvpkprpgacidsearaanytsslnlpdktlqfvkdhplm
ddsvtpidnrprlikkdvnytqivvdrtqaldgtvydvmfvstdrgalhk
aislehavhiieetqlfqdfepvqtlllsskkgnrfvyagsnsgvvqapl
afcgkhgtcedcvlardpycawspptatcvalhqtespsrgliqemsgda
svcpdkskgsyrqhffkhggtaelkcsqksnlarvfwkfqndvlkaespk
yglmgrknllifnlsegdsgvyqclseervknktvfqvvakhvlevkvvp
kpvvaptlsvvqtegsriatkvlvastqgssppptpavqatssgaitlppk
paptgtscepkivintvpqlhsektmylkssdnrllmslflfffvlflcl
ffyncykgylprqclkfrsalligkkkpksdfcdreqslketlvepgsfs
qqngehpkpaldtgyeteqdtitskvptdredsqriddlsardkpfdvkc
elkfadsdadgd SEQ ID NO: 5; accession number AAH54500:
mrmctpirgllmalavmfgtamafapipritwehrevhlvqfhepdiyny
sallsedkdtlyigareavfavnalnisekqhevywkvsedkkakcaek
gkskqteclnyirvlqplsatslyvcgtnafqpacdhlnltsfkflgkne
dgkgrcpfdpahsytsvmvdgelysgtsynflgsepiisrnsshsplrte
yaipwlnepsfvfadvirkspdspdgeddrvyffftevsveyefvfrvli
priarvckgdqgglrtlqkkwtsflkarlicsrpdsglvfnvlrdvfvlr
spglkvpvfyalftpqlnnvglsavcaynlstaeevfshgkymqsttveq
shtkwvryngpvpkprpgacidsearaanytsslnlpdktlqfvkdhplm
ddsvtpidnrprlikkdvnytqivvdrtqaldgtvydvmfvstdrgalhk
aislehavhiieetqlfqdfepvqtlllsskkgnrfvyagsnsgvvqapl
afcgkhgtcedcvlardpycawspptatcvalhqtespsrgliqemsgda
svcpdkskgsyrqhffkhggtaelkcsqksnlarvfwkfqndvlkaespk
yglmgrknllifnlsegdsgvyqclseervknktvfqvvakhvlevkvvp
``` kpvvaptlsvvqtegsriatkvlvastqgsspptpavqatssgaitlppk paptgtscepkivintvpqlhsektmylkssdnrllmslflffffvlflcl ffyncykgylprqclkfrsalligkkkpksdfcdreqslketlvepgsfs qqngehpkpaldtgyeteqdtitskvptdredsqriddlsardkpfdvkc elkfadsdadgd SEQ ID NO: 6; accession number BX648216:
ctggcgcccgaactcgcccggcgggagccgcgcgggcaggacgcgcgc tgcagactctgctaacaccagatagtggaaagaaaccatgtgctgaaatg tttgacgacactgatggtttgcatttcttctgaggccctgaagaagtatc aagtgggctttgacattgcggtggtgagagcgacccctcctcacctggag aactgggaaatgtggattctcagggaccgcgctgttcacgagctccaggc tgtgctgctggccctggtcctgggcgctgagccgcatctgcaatagcac acttgcccggccacctgctgccgtgagcctttgctgctgaagcccctggg gtcgcctctacctgatgaggatgtgcaccccccattagggggctgctcatg gcccttgcagtgatgtttgggacagcgatggcatttgcacccataccccg gatcacctgggagcacagagaggtgcacctggtgcagtttcatgagccag acatctacaactactcagccttgctgctgagcgaggacaaggacaccttg tacataggtgcccggaggcggtcttcgctgtgaacgcactcaacatctc cgagaagcagcatgaggtgtattggaaggtctcagaagacaaaaaagcaa aatgtgcagaaaaggggaaatcaaaacagacagagtgcctcaactacatc cgggtgctgcagccactcagcgccacttcccctttacgtgtgtgggaccaa cgcattccagccggcctgtgaccacctgaacttaacatcctttaagtttc tggggaaaaatgaagatggcaaaggaagatgtcccttttgacccagcacac agctacacatccgtcatggttgatggagaactttattcggggacgtcgta taattttttggaagtgaacccatcatctcccgaaattcttcccacagtc ctctgaggacagaatatgcaatcccttggctgaacgagcctagtttcgtg tttgctgacgtgatccgaaaaagcccagacagccccgacggcgaggatga cagggtctacttcttcttcacggaggtgtctgtggagtatgagtttgtgt tcagggtgctgatcccacggatagcaagagtgtgcaaggggggaccagggc ggcctgaggaccttgcagaagaaatggaccttcctcctgaaagcccgact catctgctcccggccagacagcggcttggtcttcaatgtgctgcgggatg tcttcgtgctcaggtccccgggcctgaaggtgcctgtgttctatgcactc ttcaccccacagctgaacaacgtggggctgtcggcagtgtgcgcctacaa cctgtccacagccgaggaggtcttctcccacgggaagtacatgcagagca ccacagtggagcagtcccacaccaagtgggtgcgctataatggcccggta cccaagccgcggcctggagcgtgcatcgacagcgaggcacgggccgccaa ctacaccagctccttgaatttgccagacaagacgctgcagttcgttaaag accacccttttgatggatgactcggtaaccccaatagcaacaggccagg ttaatcaagaaagatgtgaactacacccagatcgtggtggaccggaccca ggccctggatgggactgtctatgatgtcatgtttgtcagcacagaccggg gagctctgcacaaagccatcagcctcgagcacgctgttcacatcatcgag gagacccagctcttccaggactttgagccagtccagaccctgctgctgtc ttcaaagaagggcaacaggtttgtctatgctggctctaactcgggcgtgg tccaggccccgctggccttctgtgggaagcacggcacctgcgaggactgt gtgctggcgcgggacccctactgcgcctggagcccgcccacagcgacctg cgtggctctgcaccagaccgagagcccagcaggggtttgattcaggaga tgagcggcgatgcttctgtgtgcccggataaaagtaaaggaagttaccgg cagcattttttcaagcacggtggcacagcggaactgaaatgctcccaaaa atccaacctggcccgggtcttttggaagttccagaatgacgtgttgaagg ccgagagcccaagtacggtcttatgggcagaaaaaacttgctcatcttc aacttgtcagaaggagacagtggggtgtaccagtgcctgtcagaggagag ggttaagaacaaaacggtcttccaagtggtcgccaagcacgtcctggaag tgaaggtggttccaaagcccgtagtggccccaccttgtcagttgttcag acagaaggtagtaggattgccaccaaagtgttggtggcatccacccaagg gtcttctccccaaccccagccgtgcaggccacctcctccggggccatca cccttcctcccaagcctgcgtccaccggcacatcttgcgaaccaaagatc gtcatcaacacggtcccccagctccactcggagaaaaccatgtatcttaa gtccagcgacaaccgcctcccatgtccctcttcctcttcttctttgttc tcttcctctgcctctttttctacaactgctataagggatacctgcccaga cagtgcttgaaattccgctcggccctactaattgggaagaagaagcccaa gtcagatttctgtgaccgtgagcagagcctgaaggagacgttagtagagc cagggagcttctcccagcagaatggggagcaccccaagccagccctggac accggctatgagaccgagcaagacaccatcaccagcaaagtccccacgga tagggaggactcacagaggatcgacgacctttctgccagggacaagccct ttgacgtcaagtgtgagctgaagttcgctgactcagacgcagatggagac tgaggccggctgtgcatccccgctggtgcctcggctgcgacgtgtccagg cgtggagagttttgtgtttctcctgttcagtatccgagtctcgtgcagtg ctgcgtaggttagcccgcatcgtgcagacaacctcagtcctcttgtctat tttctcttgggttgagcctgtgacttggtttctctttgtccttttggaaa aatgacaagcattgcatcccagtcttgtgttccgaagtcagtcggagtac ttgaagaaggcccacgggcggcacggagttcctgagcccttctgtagtg ggggaaaggtggctggacctctgttggctgagaagagcatcccttcagct tcccctccccgtagcagccactaaaagattatttaattccagattggaaa tgacattttagtttatcagattggtaacttatcgcctgttgtccagattg gcacgaaccttttcttccacttaattatttttttaggattttgctttgat tgtgtttatgtcatgggtcatttttttttagttacagaagcagatgtgtt aatatttagaagaagatgtatatcttccagattttgttatatatttggca taaaatacggcttacgttgcttaagattctcagggataaacttccttttg ctaaatgcattctttctgcttttagaaatgtagacataaacactccccgg agcccactcacctttttttcttttttctttttttttttttaactttattcct tgagggaagcattgttttttggagagattttctttctgtacttcgttttac -continued ttttctttttttttaacttttactctctcgaagaagaggaccttcccaca
tccacgaggtgggttttgagcaagggaaggtagcctggatgagctgagtg
gagccaggctggcccagagctgagatgggagtgcggtacaatctggagcc
cacagctgtcggtcagaacctcctgtgagacagatggaaccttcacaagg
gcgcctttggttctctgaacatctcctttctcttcttgcttcaattgcat
acccactgcctgcccagactttctatccagcctcactgagctgcccacta
ctggaagggaactgggcctcggtggccggggccgcgagctgtgaccacag
caccctcaagcatacgcgctgttcctgccactgtcctgaagatgtgaat
gggtggtacgatttcaacactggttaatttcacactccatctcccgctt
tgtaaatacccatcgggaagagactttttttccatggtgaagagcaataa
actctggatgtttgtgaaaaaaaaaaaaaaaaa
SEQ ID NO: 7; accession number U60800
(SEQ ID NO: 7 = nucleotide sequence):
ctgagccgcatctgcaatagcacacttgcccggccacctgctgccgtgag
cctttgctgctgaagcccctggggtcgcctctacctgatgaggatgtgca
cccccattagggggctgctcatggcccttgcagtgatgtttgggacagcg
atggcatttgcacccatacccggatcacctgggagcacagagaggtgca
cctggtgcagtttcatgagccagacatctacaactactcagccttgctgc
tgagcgaggacaaggacaccttgtacataggtgcccgggaggcggtcttc
gctgtgaacgcactcaacatctccgagaagcagcatgaggtgtattggaa
ggtctcagaagacaaaaagcaaaatgtgcagaaaagggaaatcaaaac
agacagagtgcctcaactacatccgggtgctgcagccactcagcgccact
tcccttacgtgtgtgggaccaacgcattccagccggcctgtgaccacct
gaacttaacatcctttaagtttctggggaaaaatgaagatggcaaaggaa
gatgtccctttgacccagcacacagctacacatccgtcatggttgatgga
gaactttattcggggacgtcgtataatttttgggaagtgaacccatcat
ctcccgaaattcttcccacagtcctctgaggacagaatatgcaatccctt
ggctgaacgagcctagtttcgtgtttgctgacgtgatccgaaaaagccca
gacagccccgacggcgaggatgacagggtctacttcttcttcacggaggt
gtctgtggagtatgagtttgtgttcagggtgctgatcccacggatagcaa
gagtgtgcaaggggaccagggcggcctgaggaccttgcagaagaaatgg
acctccttcctgaaagcccgactcatctgctcccggccagacagcggctt
ggtcttcaatgtgctgcgggatgtcttcgtgctcaggtccccgggcctga
aggtgcctgtgttctatgcactcttcaccccacagctgaacaacgtgggg
ctgtcggcagtgtgcgcctacaacctgtccacagccgaggaggtcttctc
ccacgggaagtacatgcagagcaccacagtggagcagtcccacaccaagt
gggtgcgctataatggcccggtaccaagccgcgggcctggagcgtgcatc
gacagcgaggcacgggccgccaactacaccagctccttgaatttgccaga
caagacgctgcagttcgttaaagaccacccttttgatggatgactcggtaa
ccccaatagacaacaggcccaggttaatcaagaaagatgtgaactacacc
cagatcgtggtggaccggacccaggccctggatgggactgtctatgatgt
catgtttgtcagcacagaccggggagctctgcacaaagccatcagcctcg -continued agcacgctgttcacatcatcgaggagacccagctcttccaggactttgag
ccagtccagaccctgctgctgtcttcaaagaagggcaacaggtttgtcta
tgctggctctaactcgggcgtggtccaggccccgctggccttctgtggga
agcacggcacctgcgaggactgtgtgctggcgcgggacccctactgcgcc
tggagcccgcccacagcgacctgcgtggctctgcaccagaccgagagccc
cagcaggggtttgattcaggagatgagcggcgatgcttctgtgtgcccgg
ataaaagtaaaggaagttaccggcagcattttttcaagcacggtggcaca
gcggaactgaaatgctcccaaaaatccaacctggcccgggtcttttggaa
gttccagaatggcgtgttgaaggccgagagccccaagtacggtcttatgg
gcagaaaaaacttgctcatcttcaacttgtcagaaggagacagtggggtg
taccagtgcctgtcagaggagagggttaagaacaaaacggtcttccaagt
ggtcgccaagcacgtcctggaagtgaaggtggttccaaagcccgtagtgg
cccccaccttgtcagttgttcagacagaaggtagtaggattgccaccaaa
gtgttggtggcatccacccaagggtcttctcccccaaccccagccgtgca
ggccacctcctccggggccatcacccttcctcccaagcctgcgcccaccg
gcacatcctgcgaaccaaagatcgtcatcaacacgtcccccagctccac
tcggagaaaaccatgtatcttaagtccagcgacaaccgcctcctcatgtc
cctcttcctcttcttctttgttctcttcctctgcctcttttttctacaact
gctataagggatacctgcccagacagtgcttgaaattccgctcggcccta
ctaattgggaagaagaagcccaagtcagatttctgtgaccgtgagcagag
cctgaaggagacgttagtagagccagggagcttctcccagcagaatgggg
agcaccccaagccagccctggacaccggctatgagaccgagcaagacacc
atcaccagcaaagtccccacggatagggaggactcacagaggatcgacga
ccttttctgccagggacaagcccttttgacgtcaagtgtgagctgaagttcg
ctgactcagacgcagatggagactgaggccggctgtgcatcccccgctggt
gcctcggctgcgacgtgtccaggcgtggagagttttgtgtttctcctgtt
cagtatccgagtctcgtgcagtgctgcgtaggttagcccgcatcgtgcag
acaacctcagtcctcttgtctatttttctcttgggttgagcctgtgacttg
gtttctcttgtccttttggaaaaatgacaagcattgcatcccagtcttg
tgttccgaagtcagtcggagtacttgaagaaggcccacgggcggcacgga
gttcctgagcccttctctgtagtgggggaaaggtggctggacctctgttgg
ctgagaagagcatcccttcagcttccctcccgtagcagccactaaaag
attatttaattccagattggaaatgacattttagtttatcagattggtaa
cttatcgcctgttgtccagattggcacgaaccttttcttccacttaatta
ttttttttaggattttgctttgattgtgtttatgtcatgggtcatttttt
ttagttacagaagcagttgtgttaatatttagaagaagatgtatatcttc
cagattttgttatatatttggcataaaatacggcttacgttgcttaagat
tctcagggataaaacttccttttgctaaatgcattctttctgcttttagaa
atgtagacataaacactccccggagcccactcacctttttttcttttcttt
ttttttttttttaactttattccttgagggaagcattgtttttggagagat -continued tttctttctgtacttcgttttacttttcttttttttaacttttactctc tcgaagaagaggaccttcccacatccacgaggtgggttttgagcaaggga aggtagcctggatgagctgagtggagccaggctggcccagagctgagatg ggagtgcggtacaatctggagcccacagctgtcggtcagaacctcctgtg agacagatggaaccttcacaagggcgcctttggttctctgaacatctcct ttctcttcttgcttcaattgcttacccactgcctgcccagactttctatc cagcctcactgagctgcccactactggaagggaactgggcctcggtggcc ggggccgcgagctgtgaccacagcaccctcaagcatacggcgctgttcct gccactgtcctgaagatgtgaatggggtggtacgatttcaacactggttaa tttcacactccatctcccgctttgtaaatacccatcgggaagagacttt ttttccatggtgaagagcaataaactctggatgtttgtgcgcgtgtgtgg acagtcttatcttccagcatgataggatttgaccattttggtgtaaacat ttgtgtttataagatttaccttgttttattttctactttgaattgta tacatttggaaagtacccaaataaatgagaagcttctatccttaaaaaaa aaaaaaa SEQ ID NO: 8; accession number U60800
(SEQ ID NO: 8 = amino acid sequence):
mrmctpirgllmalavmfgtamafapipritwehrevhlvqfhepdiyny salllsedkdtlyigareavfavnalnisekqhevywkvsedkkakcaek gkskqteclnyirvlqplsatslyvcgtnafqpacdhlnltsfkflgkne dgkgrcpfdpahsytsvmvdgelysgtsynflgsepiisrnsshsplrte yaipwlnepsfvfadvirkspdspdgeddrvyffftevsveyefvfrvli priarvckgdqgglrtlqkkwtsflkarlicsrpdsglvfnvlrdvfvlr spglkvpvfyalftpqlnnvglsavcaynlstaeevfshgkymqsttveq shtkwvryngpvpkprpgacidsearaanytsslnlpdktlqfvkdhplm ddsvtpidnrprlikkdvnytqivvdrtqaldgtvydvmfvstdrgalhk aislehavhiieetqlfqdfepvqtllllsskkgnrfvyagsnsgvvqapl afcgkhgtcedcvlardpycawspptatcvalhqtespsrgliqemsgda svcpdkskgsyrqhffkhggtaelkcsqksnlarvfwkfqngvlkaespk yglmgrknllifnlsegdsgvyqclseervknktvfqvvakhvlevkvvp kpvvaptlsvvqtegsriatkvlvastqgsspptpavqatssgaitlppk paptgtscepkivintvpqlhsektmylkssdnrllmslflffflflcl ffyncykgylprqclkfrsalligkkkpksdfcdreqslketlvepgsfs qqngehpkpaldtgyeteqdtitskvptdredsqriddlsardkpfdvkc elkfadsdadgd SEQ ID NO: 9; accession number AAC50810:
mrmctpirgllmalavmfgtamafapipritwehrevhlvqfhepdiyny salllsedkdtlyigareavfavnalnisekqhevywkvsedkkakcaek gkskqteclnyirvlqplsatslyvcgtnafqpacdhlnltsfkflgkne dgkgrcpfdpahsytsvmvdgelysgtsynflgsepiisrnsshsplrte yaipwlnepsfvfadvirkspdspdgeddrvyffftevsveyefvfrvli priarvckgdqgglrtlqkkwtsflkarlicsrpdsglvfnvlrdvfvlr spglkvpvfyalftpqlnnvglsavcaynlstaeevfshgkymqsttveq shtkwvryngpvpkprpgacidsearaanytsslnlpdktlqfvkdhplm ddsvtpidnrprlikkdvnytqivvdrtqaldgtvydvmfvstdrgalhk aislehavhiieetqlfqdfepvqtlllsskkgnrfvyagsnsgvvqapl afcgkhgtcedcvlardpycawspptatcvalhqtespsrgliqemsgda svcpdkskgsyrqhffkhggtaelkcsqksnlarvfwkfqngvlkaespk yglmgrknllifnlsegdsgvyqclseervknktvfqvvakhvlevkvvp kpvvaptlsvvqtegsriatkvlvastqgsspptpavqatssgaitlppk paptgtscepkivintvpqlhsektmylkssdnrllmslflffflflcl ffyncykgylprqclkfrsalligkkkpksdfcdreqslketlvepgsfs qqngehpkpaldtgyeteqdtitskvptdredsqriddlsardkpfdvkc elkfadsdadgd SEQ ID NO: 10; accession number Q92854:
mrmctpirgllmalavmfgtamafapipritwehrevhlvqfhepdiyny salllsedkdtlyigareavfavnalnisekqhevywkvsedkkakcaek gkskqteclnyirvlqplsatslyvcgtnafqpacdhlnltsfkflgkne dgkgrcpfdpahsytsvmvdgelysgtsynflgsepiisrnsshsplrte yaipwlnepsfvfadvirkspdspdgeddrvyffftevsveyefvfrvli priarvckgdqgglrtlqkkwtsflkarlicsrpdsglvfnvlrdvfvlr spglkvpvfyalftpqlnnvglsavcaynlstaeevfshgkymqsttveq shtkwvryngpvpkprpgacidsearaanytsslnlpdktlqfvkdhplm ddsvtpidnrprlikkdvnytqivvdrtqaldgtvydvmfvstdrgalhk aislehavhiieetqlfqdfepvqtlllsskkgnrfvyagsnsgvvqapl afcgkhgtcedcvlardpycawspptatcvalhqtespsrgliqemsgda svcpdkskgsyrqhffkhggtaelkcsqksnlarvfwkfqngvlkaespk yglmgrknllifnlsegdsgvyqclseervknktvfqvvakhvlevkvvp kpvvaptlsvvqtegsriatkvlvastqgsspptpavqatssgaitlppk paptgtscepkivintvpqlhsektmylkssdnrllmslflffflflcl ffyncykgylprqclkfrsalligkkkpksdfcdreqslketlvepgsfs qqngehpkpaldtgyeteqdtitskvptdredsqriddlsardkpfdvkc elkfadsdadgd All publications, patents and patent applications cited in this specification are herein incorporated by reference as if each individual publication or patent application were specifically and individually indicated to be incorporated by reference.

It will be understood that the invention has been described by way of example only and modifications may be made whilst remaining within the scope and spirit of the invention.

SEQUENCE LISTING

<160> NUMBER OF SEQ ID NOS: 13

<210> SEQ ID NO 1
<211> LENGTH: 4675
<212> TYPE: DNA
<213> ORGANISM: Homo sapiens

<400> SEQUENCE: 1

| | | | | | | |
|---|---|---|---|---|---|---|
| gctgtaacac | tcaccgtgaa | ggtctgcagc | ttcactcccg | agccagcgag | accacgaacc | 60 |
| caccagaagg | aagaaactct | gaacacatct | gaacatcaga | agggacagac | tccagacgcg | 120 |
| ccaccactct | gctaacacca | gatagtggaa | agaaaccatg | tgctgaaatg | tttgacgaca | 180 |
| ctgatggttt | gactctgcta | actggaatgg | cttattgtgc | aagaaagtac | acctggtcgg | 240 |
| gtcctggggc | tcatctctag | caccagcaaa | gatttctgaa | gacgtctttc | tagaaatgac | 300 |
| tggaaagttt | caagaggcat | aagatacagc | atttcttctg | aggccctgaa | gaagtatcaa | 360 |
| gtgggctttg | acattgcggt | ggtgagagcg | accctcctc | acctggagaa | ctgggaaatg | 420 |
| tggattctca | gggaccgcgc | tgttcacgag | ctccaggctg | tgctgctggc | cctggtcctg | 480 |
| gggcgctgag | ccgcatctgc | aatagcacac | ttgcccggcc | acctgctgcc | gtgagccttt | 540 |
| gctgctgaag | cccctggggt | cgcctctacc | tgatgaggat | gtgcaccccc | attaggggc | 600 |
| tgctcatggc | ccttgcagtg | atgtttggga | cagcgatggc | atttgcaccc | ataccccgga | 660 |
| tcacctggga | gcacagagag | gtgcacctgg | tgcagtttca | tgagccagac | atctacaact | 720 |
| actcagcctt | gctgctgagc | gaggacaagg | acaccttgta | cataggtgcc | cgggaggcgg | 780 |
| tcttcgctgt | gaacgcactc | aacatctccg | agaagcagca | tgaggtgtat | tggaaggtct | 840 |
| cagaagacaa | aaaagcaaaa | tgtgcagaaa | aggggaaatc | aaaacagaca | gagtgcctca | 900 |
| actacatccg | ggtgctgcag | ccactcagcc | ccacttccct | ttacgtgtgt | gggaccaacg | 960 |
| cattccagcc | ggcctgtgac | cacctgaact | taacatcctt | taagtttctg | gggaaaaatg | 1020 |
| aagatggcaa | aggaagatgt | ccctttgacc | cagcacacag | ctacacatcc | gtcatggttg | 1080 |
| atggagaact | ttattcgggg | acgtcgtata | atttttggg | aagtgaaccc | atcatctccc | 1140 |
| gaaattcttc | ccacagtcct | ctgaggacag | aatatgcaat | cccttggctg | aacgagccta | 1200 |
| gtttcgtgtt | tgctgacgtg | atccgaaaaa | gcccagacag | ccccgacggc | gaggatgaca | 1260 |
| gggtctactt | cttcttcacg | gaggtgtctg | tggagtatga | gtttgtgttc | agggtgctga | 1320 |
| tcccacggat | agcaagagtg | tgcaaggggg | accaggcgg | cctgaggacc | ttgcagaaga | 1380 |
| aatggaccte | cttcctgaaa | gcccgactca | tctgctcccg | gccagacagc | ggcttggtct | 1440 |
| tcaatgtgct | gcgggatgtc | ttcgtgctca | ggtccccggg | cctgaaggtg | cctgtgttct | 1500 |
| atgcactctt | caccccacag | ctgaacaacg | tggggctgtc | ggcagtgtgc | gcctacaacc | 1560 |
| tgtccacagc | cgaggaggtc | ttctcccacg | ggaagtacat | gcagagcacc | acagtggagc | 1620 |
| agtcccacac | caagtgggtg | cgctataatg | gcccggtacc | caagccgcgg | cctggagcgt | 1680 |
| gcatcgacag | cgaggcacgg | gccgccaact | acaccagctc | cttgaatttg | ccagacaaga | 1740 |
| cgctgcagtt | cgttaaagac | cacccttga | tggatgactc | ggtaacccca | atagacaaca | 1800 |
| ggcccaggtt | aatcaagaaa | gatgtgaact | acacccagat | cgtggtggac | cggacccagg | 1860 |
| ccctggatgg | gactgtctat | gatgtcatgt | ttgtcagcac | agaccggga | gctctgcaca | 1920 |
| aagccatcag | cctcgagcac | gctgttcaca | tcatcgagga | gacccagctc | ttccaggact | 1980 |
| ttgagccagt | ccagaccctg | ctgctgtctt | caaagaaggg | caacaggttt | gtctatgctg | 2040 |

-continued

```
gctctaactc gggcgtggtc caggccccgc tggccttctg tgggaagcac ggcacctgcg    2100
aggactgtgt gctggcgcgg gaccccract gcgcctggag cccgcccaca gcgacctgcg    2160
tggctctgca ccagaccgag agcccagca ggggtttgat tcaggagatg agcggcgatg    2220
cttctgtgtg cccggataaa agtaaaggaa gttaccggca gcattttttc aagcacggtg    2280
gcacagcgga actgaaatgc tcccaaaaat ccaacctggc ccgggtcttt tggaagttcc    2340
agaatgacgt gttgaaggcc gagagcccca agtacggtct tatgggcaga aaaaacttgc    2400
tcatcttcaa cttgtcagaa ggagacagtg gggtgtacca gtgcctgtca gaggagaggg    2460
ttaagaacaa aacggtcttc caagtggtcg ccaagcacgt cctggaagtg aaggtggttc    2520
caaagcccgt agtggcccc accttgtcag ttgttcagac agaaggtagt aggattgcca    2580
ccaaagtgtt ggtggcatcc acccaagggt cttctccccc aaccccagcc gtgcaggcca    2640
cctcctccgg ggccatcacc cttcctccca agcctgcgcc caccggcaca tcctgcgaac    2700
caaagatcgt catcaacacg gtcccccagc tccactcgga gaaaaccatg tatcttaagt    2760
ccagcgacaa ccgcctcctc atgtccctct tcctcttctt ctttgttctc ttcctctgcc    2820
tctttttcta caactgctat aagggatacc tgcccagaca gtgcttgaaa ttccgctcgg    2880
ccctactaat tgggaagaag aagcccaagt cagatttctg tgaccgtgag cagagcctga    2940
aggagacgtt agtagagcca gggagcttct cccagcagaa tggggagcac cccaagccag    3000
ccctggacac cggctatgag accgagcaag acaccatcac cagcaaagtc cccacggata    3060
gggaggactc acagaggatc gacgaccttt ctgccaggga caagcccttt gacgtcaagt    3120
gtgagctgaa gttcgctgac tcagacgcag atggagactg aggccggctg tgcatccccg    3180
ctggtgcctc ggctgcgacg tgtccaggcg tggagagttt tgtgtttctc ctgttcagta    3240
tccgagtctc gtgcagtgct gcgtaggtta gcccgcatcg tgcagacaac ctcagtcctc    3300
ttgtctattt tctcttgggt tgagcctgtg acttggtttc tctttgtcct tttgaaaaaa    3360
tgacaatcct tgcatcccag tcttgtgttc cgaagtcagt cggagtactt gaagaaggcc    3420
cacgggcggc acggagttcc tgagcccttt ctgtagtggg ggaaaggtgg ctggacctct    3480
gttggctgag aagagcatcc cttcagcttc ccctcccegt agcagccact aaaagattat    3540
ttaattccag attggaaatg acattttagt ttatcagatt ggtaacttat cgcctgttgt    3600
ccagattggc acgaaccttt tcttccactt aattattttt ttaggatttt gctttgattg    3660
tgtttatgtc atgggtcatt ttttttagt tacagaagca gatgtgttaa tatttagaag    3720
aagatgtata tcttccagat tttgttatat atttggcata aaatacggct tacgttgctt    3780
aagattctca gggataaact tccttttgct aaatgcattc tttctgcttt tagaaatgta    3840
gacataaaca ctccccggag cccactcacc tttttctttt tcttttttt tttttaact    3900
ttattccttg agggaagcat tgttttgga gagatttttct ttctgtactt cgttttactt    3960
ttctttttt ttaacttta ctctctcgaa gaagaggacc ttcccacatc cacgaggtgg    4020
gttttgagca agggaaggta gcctggatga gctgagtgga gccaggctgg cccagagctg    4080
agatgggagt gcggtacaat ctggagccca cagctgtcgg tcagaacctc ctgtgagaca    4140
gatggaacct tcacaagggc gcctttggtt ctctgaacat ctcctttctc ttcttgcttc    4200
aattgcatac ccactgcctg cccagacttt ctatccagcc tcactgagct gcccactact    4260
ggaagggaac tgggcctcgg tggccggggc gcgagctgt gaccacagca ccctcaagca    4320
tacggcgctg ttcctgccac tgtcctgaag atgtgaatgg gtggtacgat ttcaacactg    4380
gttaatttca cactccatct ccccgctttg taaatacccca tcgggaagag actttttttc    4440
```

-continued

```
catggtgaag agcaataaac tctggatgtt tgtgcgcgtg tgtggacagt cttatcttcc    4500
agcatgatag gatttgacca ttttggtgta acatttgtg ttttataaga tttaccttgt     4560 ttttatttt  ctactttgaa ttgtatacat ttggaaagta cccaaataaa tgagaagctt    4620
ctatccttaa aaaaaaaaaa aaaaaaaaaa aaaaaaaaaa aaaaaaaaaa aaaaa         4675
```

<210> SEQ ID NO 2
<211> LENGTH: 856
<212> TYPE: PRT
<213> ORGANISM: Homo sapiens

<400> SEQUENCE: 2

```
Met Arg Met Cys Thr Pro Ile Arg Gly Leu Leu Met Ala Val Met Phe
 1               5                  10                  15

Gly Thr Ala Met Ala Phe Ala Pro Ile Pro Arg Ile Thr Trp Glu His
             20                  25                  30

Arg Glu Val His Leu Val Gln Phe His Glu Pro Asp Ile Tyr Asn Tyr
         35                  40                  45

Ser Ala Leu Leu Leu Ser Glu Asp Lys Asp Thr Leu Tyr Ile Gly Ala
     50                  55                  60

Arg Glu Ala Val Phe Ala Val Asn Ala Leu Asn Ile Ser Glu Lys Gln
 65                  70                  75                  80

His Glu Val Tyr Trp Lys Val Ser Glu Asp Lys Lys Ala Lys Cys Ala
                 85                  90                  95

Glu Lys Gly Lys Ser Lys Gln Thr Glu Cys Leu Asn Tyr Ile Arg Val
            100                 105                 110

Leu Gln Pro Leu Ser Ala Thr Ser Leu Tyr Val Cys Gly Thr Asn Ala
        115                 120                 125

Phe Gln Pro Ala Cys Asp His Leu Asn Leu Thr Ser Phe Lys Phe Leu
    130                 135                 140

Gly Lys Asn Glu Asp Gly Lys Gly Arg Cys Pro Phe Asp Pro Ala His
145                 150                 155                 160

Ser Tyr Thr Ser Val Met Val Asp Gly Glu Lys Gly Thr Ser Tyr Asn
                165                 170                 175

Phe Leu Gly Ser Glu Pro Ile Ile Ser Arg Asn Ser Ser His Ser Pro
            180                 185                 190

Leu Arg Thr Glu Tyr Ala Ile Pro Trp Leu Asn Glu Pro Ser Phe Val
        195                 200                 205

Phe Ala Asp Val Ile Arg Lys Ser Pro Asp Ser Pro Asp Gly Glu Asp
    210                 215                 220

Asp Arg Val Tyr Phe Phe Thr Glu Val Ser Val Glu Tyr Glu Phe
225                 230                 235                 240

Val Phe Arg Val Leu Ile Pro Arg Ile Ala Arg Val Cys Lys Gly Asp
                245                 250                 255

Gln Gly Gly Leu Arg Thr Leu Gln Lys Lys Trp Thr Ser Phe Leu Lys
            260                 265                 270

Ala Arg Leu Ile Cys Ser Arg Pro Asp Ser Gly Leu Val Phe Asn Val
        275                 280                 285

Leu Arg Asp Val Phe Val Leu Arg Ser Pro Gly Leu Lys Val Pro Val
    290                 295                 300

Phe Tyr Ala Leu Phe Thr Pro Gln Leu Asn Asn Val Gly Leu Ser Ala
305                 310                 315                 320

Val Cys Ala Tyr Asn Leu Ser Thr Ala Glu Glu Val Phe Ser His Gly
                325                 330                 335

Lys Tyr Met Gln Ser Thr Thr Val Glu Gln Ser His Thr Lys Trp Val
```

-continued

```
                340                 345                 350
Arg Tyr Asn Gly Pro Val Pro Lys Pro Arg Pro Gly Ala Cys Ile Asp
            355                 360                 365
Ser Glu Ala Arg Ala Ala Asn Tyr Thr Ser Ser Leu Asn Leu Pro Asp
        370                 375                 380
Lys Thr Leu Gln Phe Val Lys Asp His Pro Leu Met Asp Asp Ser Val
385                 390                 395                 400
Thr Pro Ile Asp Asn Arg Pro Arg Leu Ile Lys Lys Asp Val Asn Tyr
                405                 410                 415
Thr Gln Ile Val Val Asp Arg Thr Gln Ala Leu Asp Gly Thr Val Tyr
            420                 425                 430
Asp Val Met Phe Val Ser Thr Asp Arg Gly Ala Leu His Lys Ala Ile
        435                 440                 445
Ser Leu Glu His Ala Val His Ile Ile Glu Glu Thr Gln Leu Phe Gln
    450                 455                 460
Asp Phe Glu Pro Val Gln Thr Leu Leu Leu Ser Ser Lys Lys Gly Asn
465                 470                 475                 480
Arg Phe Val Tyr Ala Gly Ser Asn Ser Gly Val Val Gln Ala Pro Leu
                485                 490                 495
Ala Phe Cys Gly Lys His Gly Thr Cys Glu Asp Cys Val Leu Ala Arg
            500                 505                 510
Asp Pro Tyr Cys Ala Trp Ser Pro Pro Thr Ala Thr Cys Val His Gln
        515                 520                 525
Thr Glu Ser Pro Ser Arg Gly Leu Ile Gln Glu Met Ser Gly Asp Ala
    530                 535                 540
Ser Val Cys Pro Asp Lys Ser Lys Gly Ser Tyr Arg Gln His Phe Phe
545                 550                 555                 560
Lys His Gly Gly Thr Ala Glu Leu Lys Cys Ser Gln Lys Ser Asn Leu
                565                 570                 575
Ala Arg Val Phe Trp Lys Phe Gln Asn Asp Val Leu Lys Ala Glu Ser
            580                 585                 590
Pro Lys Tyr Gly Leu Met Gly Arg Lys Asn Leu Leu Ile Phe Asn Leu
        595                 600                 605
Ser Glu Gly Asp Ser Gly Val Tyr Gln Cys Leu Ser Glu Glu Arg Val
    610                 615                 620
Lys Asn Lys Thr Val Phe Gln Val Val Ala Lys His Val Leu Glu Val
625                 630                 635                 640
Lys Val Val Pro Lys Pro Val Val Ala Pro Thr Leu Ser Val Val Gln
                645                 650                 655
Thr Glu Gly Ser Arg Ile Ala Thr Lys Val Leu Val Ala Ser Thr Gln
            660                 665                 670
Gly Ser Ser Pro Pro Thr Pro Ala Val Gln Ala Thr Ser Ser Gly Ala
        675                 680                 685
Ile Thr Leu Pro Pro Lys Pro Ala Pro Thr Gly Thr Ser Cys Glu Pro
    690                 695                 700
Lys Ile Val Ile Asn Thr Val Pro Gln Leu His Ser Glu Lys Thr Met
705                 710                 715                 720
Tyr Leu Lys Ser Ser Asp Asn Arg Leu Leu Met Ser Leu Phe Leu Phe
                725                 730                 735
Phe Phe Val Leu Phe Leu Cys Leu Phe Phe Tyr Asn Cys Tyr Lys Gly
            740                 745                 750
Tyr Leu Pro Arg Gln Cys Leu Lys Phe Arg Ser Ala Leu Leu Ile Gly
        755                 760                 765
```

| | | | | | | | | | | | | |
|---|---|---|---|---|---|---|---|---|---|---|---|---|
|Lys|Lys|Lys|Pro|Lys|Ser|Asp|Phe|Cys|Asp|Arg|Glu|Gln Ser Leu Lys|
| |770| | | |775| | | |780| | | |

| | | | | | | | | | | | | |
|---|---|---|---|---|---|---|---|---|---|---|---|---|
|Glu|Thr|Leu|Val|Glu|Pro|Gly|Ser|Phe|Ser|Gln|Gln|Asn Gly Glu His|
|785| | | | |790| | | | |795| | 800|

| | | | | | | | | | | | | |
|---|---|---|---|---|---|---|---|---|---|---|---|---|
|Pro|Lys|Pro|Ala|Leu|Asp|Thr|Gly|Tyr|Glu|Thr|Glu|Gln Asp Thr Ile|
| | | |805| | | | |810| | | | 815|

| | | | | | | | | | | | | |
|---|---|---|---|---|---|---|---|---|---|---|---|---|
|Thr|Ser|Lys|Val|Pro|Thr|Asp|Arg|Glu|Asp|Ser|Gln|Arg Ile Asp Asp|
| | | |820| | | | |825| | | | 830|

| | | | | | | | | | | | | |
|---|---|---|---|---|---|---|---|---|---|---|---|---|
|Leu|Ser|Ala|Arg|Asp|Lys|Pro|Phe|Asp|Val|Lys|Cys|Glu Leu Lys Phe|
| | |835| | | | |840| | | | |845|

| | | | | | |
|---|---|---|---|---|---|
|Ala|Asp|Ser|Asp|Ala|Asp Gly Asp|
| |850| | | |855|

```
<210> SEQ ID NO 3
<211> LENGTH: 4675
<212> TYPE: DNA
<213> ORGANISM: Homo sapiens

<400> SEQUENCE: 3
gctgtaacac tcaccgtgaa ggtctgcagc ttcactcccg agccagcgag accacgaacc      60
caccagaagg aagaaactct gaacacatct gaacatcaga agggacagac tccagacgcg     120
ccaccactct gctaacacca gatagtggaa agaaaccatg tgctgaaatg tttgacgaca     180
ctgatggttt gactctgcta actggaatgg cttattgtgc aagaaagtac acctggtcgg     240
gtcctggggc tcatctctag caccagcaaa gatttctgaa gacgtctttc tagaaatgac     300
tggaaagttt caagaggcat aagatacagc atttcttctg aggccctgaa gaagtatcaa     360
gtgggctttg acattgcggt ggtgagagcg acccctcctc acctggagaa ctgggaaatg     420
tggattctca gggaccgcgc tgttcacgag ctccaggctg tgctgctggc cctggtcctg     480
gggcgctgag ccgcatctgc aatagcacac ttgcccggcc acctgctgcc gtgagccttt     540
gctgctgaag cccctggggt cgcctctacc tgatgaggat gtgcaccccc attaggggc     600 tgctcatggc ccttgcagtg atgtttggga cagcgatggc atttgcaccc ataccccgga     660
tcacctggga gcacagagag gtgcacctgg tgcagtttca tgagccagac atctacaact     720
actcagcctt gctgctgagc gaggacaagg acaccttgta cataggtgcc cgggaggcgg     780
tcttcgctgt gaacgcactc aacatctccg agaagcagca tgaggtgtat ggaaggtct     840 cagaagacaa aaagcaaaa tgtgcagaaa aggggaaatc aaaacagaca gagtgcctca     900
actacatccg ggtgctgcag ccactcagcg ccacttccct ttacgtgtgt gggaccaacg     960
cattccagcc ggcctgtgac cacctgaact aacatccctt taagtttctg ggaaaaatg    1020 aagatggcaa aggaagatgt cccttttgacc cagcacacag ctacacatcc gtcatggttg    1080
atggagaact ttattcgggg acgtcgtata attttttggg aagtgaaccc atcatctccc    1140
gaaattcttc ccacagtcct ctgaggacag aatatgcaat cccttggctg aacgagccta    1200
gtttcgtgtt tgctgacgtg atccgaaaaa gcccagacag ccccgacggc gaggatgaca    1260
gggtctactt cttcttcacg gaggtgtctg tggagtatga gtttgtgttc agggtgctga    1320
tcccacggat agcaagagtg tgcaagggg accagggcgg cctgaggacc ttgcagaaga    1380
aatggaccct cttcctgaaa gcccgactca tctgctcccg ccagacagc ggcttggtct    1440 tcaatgtgct gcgggatgtc ttcgtgctca gtcccgggg cctgaaggtg cctgtgttct    1500
atgcactctt caccccacag ctgaacaacg tgggctgtc ggcagtgtgc gcctacaacc    1560
tgtccacagc cgaggaggtc ttctcccacg ggaagtacat gcagagcacc acagtgggc    1620
```

-continued

```
agtcccacac caagtgggtg cgctataatg gcccggtacc caagccgcgg cctggagcgt    1680
gcatcgacag cgaggcacgg gccgccaact acaccagctc cttgaatttg ccagacaaga    1740
cgctgcagtt cgttaaagac caccctttga tggatgactc ggtaacccca atagacaaca    1800
ggcccaggtt aatcaagaaa gatgtgaact acacccagat cgtggtggac cggacccagg    1860
ccctggatgg gactgtctat gatgtcatgt ttgtcagcac agaccgggga gctctgcaca    1920
aagccatcag cctcgagcac gctgttcaca tcatcgagga gacccagctc ttccaggact    1980
ttgagccagt ccagaccctg ctgctgtctt caaagaaggg caacaggttt gtctatgctg    2040
gctctaactc gggcgtggtc caggccccgc tggccttctg tgggaagcac ggcacctgcg    2100
aggactgtgt gctggcgcgg gaccCctact gcgcctggag cccgcccaca gcgacctgcg    2160
tggctctgca ccagaccgag agccccagca ggggtttgat tcaggagatg agcggcgatg    2220
cttctgtgtg cccggataaa agtaaaggaa gttaccggca gcattttttc aagcacggtg    2280
gcacagcgga actgaaatgc tcccaaaaat ccaacctggc ccgggtcttt tggaagttcc    2340
agaatgacgt gttgaaggcc gagagcccca gtacggtct tatgggcaga aaaaacttgc    2400
tcatcttcaa cttgtcagaa ggagacagtg gggtgtacca gtgcctgtca gaggagaggg    2460
ttaagaacaa aacggtcttc caagtggtcg ccaagcacgt cctggaagtg aaggtggttc    2520
caaagcccgt agtggccccc accttgtcag ttgttcagac agaaggtagt aggattgcca    2580
ccaaagtgtt ggtggcatcc acccaagggt cttctccccc aaccccagcc gtgcaggcca    2640
cctcctccgg ggccatcacc cttcctccca agcctgcgcc caccggcaca tcctgcgaac    2700
caaagatcgt catcaacacg gtcccccagc tccactcgga gaaaaccatg tatcttaagt    2760
ccagcgacaa ccgcctcctc atgtccctct tcctcttctt cttgttctc ttcctctgcc    2820 tcttttttcta caactgctat aagggatacc tgccagaca gtgcttgaaa ttccgctcgg    2880
ccctactaat tgggaagaag aagcccaagt cagatttctg tgaccgtgag cagagcctga    2940
aggagacgtt agtagagcca gggagcttct cccagcagaa tggggagcac cccaagccag    3000
ccctggacac cggctatgag accgagcaag acaccatcac cagcaaagtc cccacggata    3060
gggaggactc acagaggatc gacgaccttt ctgccaggga caagcccttt gacgtcaagt    3120
gtgagctgaa gttcgctgac tcagacgcag atggagactg aggccggctg tgcatccccg    3180
ctggtgcctc ggctgcgacg tgtccaggcg tggagagttt tgtgtttctc ctgttcagta    3240
tccgagtctc gtgcagtgct gcgtaggtta gcccgcatcg tgcagacaac ctcagtcctc    3300
ttgtctattt tctcttgggt tgagcctgtg acttggtttc tctttgtcct tttgaaaaa    3360 tgacaatcct tgcatcccag tcttgtgttc cgaagtcagt cggagtactt gaagaaggcc    3420
cacgggcggc acggagttcc tgagcccttt ctgtagtggg ggaaaggtgg ctggacctct    3480
gttggctgag aagagcatcc cttcagcttc ccctcccgt agcagccact aaaagattat    3540
ttaattccag attggaaatg acattttagt ttatcagatt ggtaacttat cgcctgttgt    3600
ccagattggc acgaacctt tcttccactt aattattttt ttaggatttt gctttgattg    3660
tgtttatgtc atgggtcatt ttttttagt tacagaagca gatgtgttaa tatttagaag    3720
aagatgtata tcttccagat tttgttatat atttggcata aaatacggct tacgttgctt    3780
aagattctca gggataaact tcctttgct aaatgcattc tttctgcttt tagaaatgta    3840
gacataaaca ctccccggag cccactcacc tttttcttt ttcttttttt tttttaact    3900 ttattccttg agggaagcat tgttttgga gagattttct ttctgtactt cgttttactt    3960 ttctttttt ttaacttta ctctctcgaa gaagaggacc ttcccacatc cacgaggtgg    4020
```

-continued

```
gttttgagca agggaaggta gcctggatga gctgagtgga gccaggctgg cccagagctg     4080
agatgggagt gcggtacaat ctggagccca cagctgtcgg tcagaacctc ctgtgagaca     4140
gatggaacct tcacaagggc gcctttggtt ctctgaacat ctcctttctc ttcttgcttc     4200
aattgcatac ccactgcctg cccagacttt ctatccagcc tcactgagct gcccactact     4260
ggaagggaac tgggcctcgg tggccggggc cgcgagctgt gaccacagca ccctcaagca     4320
tacggcgctg ttcctgccac tgtcctgaag atgtgaatgg gtggtacgat tcaacactg      4380 gttaatttca cactccatct ccccgctttg taaatacccca tcgggaagag acttttttc     4440 catggtgaag agcaataaac tctggatgtt tgtgcgcgtg tgtggacagt cttatcttcc     4500
agcatgatag gatttgacca ttttggtgta aacatttgtg ttttataaga tttaccttgt     4560
ttttattttt ctactttgaa ttgtatacat ttggaaagta cccaaataaa tgagaagctt     4620
ctatccttaa aaaaaaaaaa aaaaaaaaaa aaaaaaaaaa aaaaaaaaaa aaaaa          4675
```

<210> SEQ ID NO 4
<211> LENGTH: 856
<212> TYPE: PRT
<213> ORGANISM: Homo sapiens

<400> SEQUENCE: 4

```
Met Arg Met Cys Thr Pro Ile Arg Gly Leu Leu Met Ala Val Met Phe
 1               5                  10                  15

Gly Thr Ala Met Ala Phe Ala Pro Ile Pro Arg Ile Thr Trp Glu His
            20                  25                  30

Arg Glu Val His Leu Val Gln Phe His Glu Pro Asp Ile Tyr Asn Tyr
        35                  40                  45

Ser Ala Leu Leu Leu Ser Glu Asp Lys Asp Thr Leu Tyr Ile Gly Ala
    50                  55                  60

Arg Glu Ala Val Phe Ala Val Asn Ala Leu Asn Ile Ser Glu Lys Gln
65                  70                  75                  80

His Glu Val Tyr Trp Lys Val Ser Glu Asp Lys Lys Ala Lys Cys Ala
                85                  90                  95

Glu Lys Gly Lys Ser Lys Gln Thr Glu Cys Leu Asn Tyr Ile Arg Val
            100                 105                 110

Leu Gln Pro Leu Ser Ala Thr Ser Leu Tyr Val Cys Gly Thr Asn Ala
        115                 120                 125

Phe Gln Pro Ala Cys Asp His Leu Asn Leu Thr Ser Phe Lys Phe Leu
    130                 135                 140

Gly Lys Asn Glu Asp Gly Lys Gly Arg Cys Pro Phe Asp Pro Ala His
145                 150                 155                 160

Ser Tyr Thr Ser Val Met Val Asp Gly Glu Lys Gly Thr Ser Tyr Asn
                165                 170                 175

Phe Leu Gly Ser Glu Pro Ile Ile Ser Arg Asn Ser Ser His Ser Pro
            180                 185                 190

Leu Arg Thr Glu Tyr Ala Ile Pro Trp Leu Asn Glu Pro Ser Phe Val
        195                 200                 205

Phe Ala Asp Val Ile Arg Lys Ser Pro Asp Ser Pro Asp Gly Glu Asp
    210                 215                 220

Asp Arg Val Tyr Phe Phe Phe Thr Glu Val Ser Val Glu Tyr Glu Phe
225                 230                 235                 240

Val Phe Arg Val Leu Ile Pro Arg Ile Ala Arg Val Cys Lys Gly Asp
                245                 250                 255

Gln Gly Gly Leu Arg Thr Leu Gln Lys Lys Trp Thr Ser Phe Leu Lys
            260                 265                 270
```

```
Ala Arg Leu Ile Cys Ser Arg Pro Asp Ser Gly Leu Val Phe Asn Val
            275                 280                 285

Leu Arg Asp Val Phe Val Leu Arg Ser Pro Gly Leu Lys Val Pro Val
    290                 295                 300

Phe Tyr Ala Leu Phe Thr Pro Gln Leu Asn Asn Val Gly Leu Ser Ala
305                 310                 315                 320

Val Cys Ala Tyr Asn Leu Ser Thr Ala Glu Glu Val Phe Ser His Gly
                325                 330                 335

Lys Tyr Met Gln Ser Thr Thr Val Glu Gln Ser His Thr Lys Trp Val
            340                 345                 350

Arg Tyr Asn Gly Pro Val Pro Lys Pro Arg Pro Gly Ala Cys Ile Asp
        355                 360                 365

Ser Glu Ala Arg Ala Ala Asn Tyr Thr Ser Ser Leu Asn Leu Pro Asp
370                 375                 380

Lys Thr Leu Gln Phe Val Lys Asp His Pro Leu Met Asp Asp Ser Val
385                 390                 395                 400

Thr Pro Ile Asp Asn Arg Pro Arg Leu Ile Lys Lys Asp Val Asn Tyr
                405                 410                 415

Thr Gln Ile Val Val Asp Arg Thr Gln Ala Leu Asp Gly Thr Val Tyr
            420                 425                 430

Asp Val Met Phe Val Ser Thr Asp Arg Gly Ala Leu His Lys Ala Ile
        435                 440                 445

Ser Leu Glu His Ala Val His Ile Ile Glu Glu Thr Gln Leu Phe Gln
450                 455                 460

Asp Phe Glu Pro Val Gln Thr Leu Leu Leu Ser Ser Lys Lys Gly Asn
465                 470                 475                 480

Arg Phe Val Tyr Ala Gly Ser Asn Ser Gly Val Val Gln Ala Pro Leu
                485                 490                 495

Ala Phe Cys Gly Lys His Gly Thr Cys Glu Asp Cys Val Leu Ala Arg
            500                 505                 510

Asp Pro Tyr Cys Ala Trp Ser Pro Pro Thr Ala Thr Cys Val His Gln
        515                 520                 525

Thr Glu Ser Pro Ser Arg Gly Leu Ile Gln Glu Met Ser Gly Asp Ala
530                 535                 540

Ser Val Cys Pro Asp Lys Ser Lys Gly Ser Tyr Arg Gln His Phe Phe
545                 550                 555                 560

Lys His Gly Gly Thr Ala Glu Leu Lys Cys Ser Gln Lys Ser Asn Leu
                565                 570                 575

Ala Arg Val Phe Trp Lys Phe Gln Asn Asp Val Leu Lys Ala Glu Ser
            580                 585                 590

Pro Lys Tyr Gly Leu Met Gly Arg Lys Asn Leu Leu Ile Phe Asn Leu
        595                 600                 605

Ser Glu Gly Asp Ser Gly Val Tyr Gln Cys Leu Ser Glu Glu Arg Val
610                 615                 620

Lys Asn Lys Thr Val Phe Gln Val Val Ala Lys His Val Leu Glu Val
625                 630                 635                 640

Lys Val Val Pro Lys Pro Val Val Ala Pro Thr Leu Ser Val Val Gln
                645                 650                 655

Thr Glu Gly Ser Arg Ile Ala Thr Lys Val Leu Val Ala Ser Thr Gln
            660                 665                 670

Gly Ser Ser Pro Pro Thr Pro Ala Val Gln Ala Thr Ser Ser Gly Ala
        675                 680                 685

Ile Thr Leu Pro Pro Lys Pro Ala Pro Thr Gly Thr Ser Cys Glu Pro
```

```
            690                 695                 700
Lys Ile Val Ile Asn Thr Val Pro Gln Leu His Ser Glu Lys Thr Met
705                 710                 715                 720

Tyr Leu Lys Ser Ser Asp Asn Arg Leu Leu Met Ser Leu Phe Leu Phe
                725                 730                 735

Phe Phe Val Leu Phe Leu Cys Leu Phe Phe Tyr Asn Cys Tyr Lys Gly
            740                 745                 750

Tyr Leu Pro Arg Gln Cys Leu Lys Phe Arg Ser Ala Leu Leu Ile Gly
                755                 760                 765

Lys Lys Lys Pro Lys Ser Asp Phe Cys Asp Arg Glu Gln Ser Leu Lys
770                 775                 780

Glu Thr Leu Val Glu Pro Gly Ser Phe Ser Gln Gln Asn Gly Glu His
785                 790                 795                 800

Pro Lys Pro Ala Leu Asp Thr Gly Tyr Glu Thr Gln Asp Thr Ile
            805                 810                 815

Thr Ser Lys Val Pro Thr Asp Arg Glu Asp Ser Gln Arg Ile Asp Asp
                820                 825                 830

Leu Ser Ala Arg Asp Lys Pro Phe Asp Val Lys Cys Glu Leu Lys Phe
835                 840                 845

Ala Asp Ser Asp Ala Asp Gly Asp
850                 855

<210> SEQ ID NO 5
<211> LENGTH: 856
<212> TYPE: PRT
<213> ORGANISM: Homo sapiens

<400> SEQUENCE: 5

Met Arg Met Cys Thr Pro Ile Arg Gly Leu Leu Met Ala Val Met Phe
1               5                   10                  15

Gly Thr Ala Met Ala Phe Ala Pro Ile Pro Arg Ile Thr Trp Glu His
                20                  25                  30

Arg Glu Val His Leu Val Gln Phe His Glu Pro Asp Ile Tyr Asn Tyr
            35                  40                  45

Ser Ala Leu Leu Leu Ser Glu Asp Lys Asp Thr Leu Tyr Ile Gly Ala
        50                  55                  60

Arg Glu Ala Val Phe Ala Val Asn Ala Leu Asn Ile Ser Glu Lys Gln
65                  70                  75                  80

His Glu Val Tyr Trp Lys Val Ser Glu Asp Lys Lys Ala Lys Cys Ala
                85                  90                  95

Glu Lys Gly Lys Ser Lys Gln Thr Glu Cys Leu Asn Tyr Ile Arg Val
            100                 105                 110

Leu Gln Pro Leu Ser Ala Thr Ser Leu Tyr Val Cys Gly Thr Asn Ala
        115                 120                 125

Phe Gln Pro Ala Cys Asp His Leu Asn Leu Thr Ser Phe Lys Phe Leu
130                 135                 140

Gly Lys Asn Glu Asp Gly Lys Gly Arg Cys Pro Phe Asp Pro Ala His
145                 150                 155                 160

Ser Tyr Thr Ser Val Met Val Asp Gly Glu Lys Gly Thr Ser Tyr Asn
                165                 170                 175

Phe Leu Gly Ser Glu Pro Ile Ile Ser Arg Asn Ser Ser His Ser Pro
            180                 185                 190

Leu Arg Thr Glu Tyr Ala Ile Pro Trp Leu Asn Glu Pro Ser Phe Val
        195                 200                 205

Phe Ala Asp Val Ile Arg Lys Ser Pro Asp Ser Pro Asp Gly Glu Asp
```

```
              210                 215                 220
Asp Arg Val Tyr Phe Phe Thr Glu Val Ser Val Glu Tyr Glu Phe
225                 230                 235                 240

Val Phe Arg Val Leu Ile Pro Arg Ile Ala Arg Val Cys Lys Gly Asp
            245                 250                 255

Gln Gly Gly Leu Arg Thr Leu Gln Lys Lys Trp Thr Ser Phe Leu Lys
            260                 265                 270

Ala Arg Leu Ile Cys Ser Arg Pro Asp Ser Gly Leu Val Phe Asn Val
            275                 280                 285

Leu Arg Asp Val Phe Val Leu Arg Ser Pro Gly Leu Lys Val Pro Val
    290                 295                 300

Phe Tyr Ala Leu Phe Thr Pro Gln Leu Asn Asn Val Gly Leu Ser Ala
305                 310                 315                 320

Val Cys Ala Tyr Asn Leu Ser Thr Ala Glu Glu Val Phe Ser His Gly
                325                 330                 335

Lys Tyr Met Gln Ser Thr Thr Val Glu Gln Ser His Thr Lys Trp Val
            340                 345                 350

Arg Tyr Asn Gly Pro Val Pro Lys Pro Arg Pro Gly Ala Cys Ile Asp
            355                 360                 365

Ser Glu Ala Arg Ala Ala Asn Tyr Thr Ser Ser Leu Asn Leu Pro Asp
    370                 375                 380

Lys Thr Leu Gln Phe Val Lys Asp His Pro Leu Met Asp Asp Ser Val
385                 390                 395                 400

Thr Pro Ile Asp Asn Arg Pro Arg Leu Ile Lys Lys Asp Val Asn Tyr
                405                 410                 415

Thr Gln Ile Val Val Asp Arg Thr Gln Ala Leu Asp Gly Thr Val Tyr
            420                 425                 430

Asp Val Met Phe Val Ser Thr Asp Arg Gly Ala Leu His Lys Ala Ile
                435                 440                 445

Ser Leu Glu His Ala Val His Ile Ile Glu Gly Thr Gln Leu Phe Gln
    450                 455                 460

Asp Phe Glu Pro Val Gln Thr Leu Leu Leu Ser Ser Lys Lys Gly Asn
465                 470                 475                 480

Arg Phe Val Tyr Ala Gly Ser Asn Ser Gly Val Val Gln Ala Pro Leu
                485                 490                 495

Ala Phe Cys Gly Lys His Gly Thr Cys Glu Asp Cys Val Leu Ala Arg
            500                 505                 510

Asp Pro Tyr Cys Ala Trp Ser Pro Pro Thr Ala Thr Cys Val His Gln
            515                 520                 525

Thr Glu Ser Pro Ser Arg Gly Leu Ile Gln Glu Met Ser Gly Asp Ala
    530                 535                 540

Ser Val Cys Pro Asp Lys Ser Lys Gly Ser Tyr Arg Gln His Phe Phe
545                 550                 555                 560

Lys His Gly Gly Thr Ala Glu Leu Lys Cys Ser Gln Lys Ser Asn Leu
                565                 570                 575

Ala Arg Val Phe Trp Lys Phe Gln Asn Asp Val Leu Lys Ala Glu Ser
            580                 585                 590

Pro Lys Tyr Gly Leu Met Gly Arg Lys Asn Leu Leu Ile Phe Asn Leu
            595                 600                 605

Ser Glu Gly Asp Ser Gly Val Tyr Gln Cys Leu Ser Glu Glu Arg Val
    610                 615                 620

Lys Asn Lys Thr Val Phe Gln Val Val Ala Lys His Val Leu Glu Val
625                 630                 635                 640
```

| | | | | | | | | | | | |
|---|---|---|---|---|---|---|---|---|---|---|---|
|Lys|Val|Val|Pro|Lys|Pro|Val|Ala|Pro|Thr|Leu|Ser|Val|Val|Gln|
| | | |645| | |650| | | |655| |

Thr Glu Gly Ser Arg Ile Ala Thr Lys Val Leu Val Ala Ser Thr Gln
            660             665             670

Gly Ser Ser Pro Pro Thr Pro Ala Val Gln Ala Thr Ser Ser Gly Ala
            675             680             685

Ile Thr Leu Pro Pro Lys Pro Ala Pro Thr Gly Thr Ser Cys Glu Pro
            690             695             700

Lys Ile Val Ile Asn Thr Val Pro Gln Leu His Ser Glu Lys Thr Met
705             710             715             720

Tyr Leu Lys Ser Ser Asp Asn Arg Leu Leu Met Ser Leu Phe Leu Phe
            725             730             735

Phe Phe Val Leu Phe Leu Cys Leu Phe Phe Tyr Asn Cys Tyr Lys Gly
            740             745             750

Tyr Leu Pro Arg Gln Cys Leu Lys Phe Arg Ser Ala Leu Leu Ile Gly
            755             760             765

Lys Lys Lys Pro Lys Ser Asp Phe Cys Asp Arg Glu Gln Ser Leu Lys
            770             775             780

Glu Thr Leu Val Glu Pro Gly Ser Phe Ser Gln Gln Asn Gly Glu His
785             790             795             800

Pro Lys Pro Ala Leu Asp Thr Gly Tyr Glu Thr Glu Gln Asp Thr Ile
            805             810             815

Thr Ser Lys Val Pro Thr Asp Arg Glu Asp Ser Gln Arg Ile Asp Asp
            820             825             830

Leu Ser Ala Arg Asp Lys Pro Phe Asp Val Lys Cys Glu Leu Lys Phe
            835             840             845

Ala Asp Ser Asp Ala Asp Gly Asp
            850             855

<210> SEQ ID NO 6
<211> LENGTH: 4284
<212> TYPE: DNA
<213> ORGANISM: Homo sapiens

<400> SEQUENCE: 6

| | | |
|---|---|---|
|ctggcgcccg aactcgcccg gccgggagcc gccgcgggca ggacgcgcgc tgcagactct|60|
|gctaacacca gatagtggaa agaaaccatg tgctgaaatg tttgacgaca ctgatggttt|120|
|gcatttcttc tgaggccctg aagaagtatc aagtgggctt tgacattgcg gtggtgagag|180|
|cgacccctcc tcacctggag aactgggaaa tgtggattct cagggaccgc gctgttcacg|240|
|agctccaggc tgtgctgctg gccctggtcc tgggcgctg agccgcatct gcaatagcac|300|
|acttgcccgg ccacctgctg ccgtgagcct ttgctgctga gcccctggg gtcgcctcta|360|
|cctgatgagg atgtgcaccc ccattagggg gctgctcatg gcccttgcag tgatgtttgg|420|
|gacagcgatg gcatttgcac ccataccccg gatcacctgg gagcacagag aggtgcacct|480|
|ggtgcagttt catgagccag acatctacaa ctactcagcc ttgctgctga gcgaggacaa|540|
|ggacaccttg tacataggtg cccgggaggc ggtcttcgct gtgaacgcac tcaacatctc|600|
|cgagaagcag catgaggtgt attggaaggt ctcagaagac aaaaaagcaa atgtgcagaa|660|
|aaagggaaa tcaaaacaga cagagtgcct caactcatc cgggtgctgc agccactcag|720|
|cgccacttcc ctttacgtgt gtgggaccaa cgcattccag ccggcctgtg accacctgaa|780|
|cttaacatcc tttaagtttc tggggaaaaa tgaagatggc aaaggaagat gtccctttga|840|
|cccagcacac agctacacat ccgtcatggt tgatggagaa ctttattcgg ggacgtcgta|900|

```
taatttttg  ggaagtgaac  ccatcatctc  ccgaaattct  tcccacagtc  ctctgaggac    960
agaatatgca  atcccttggc  tgaacgagcc  tagtttcgtg  tttgctgacg  tgatccgaaa   1020
aagcccagac  agccccgacg  gcgaggatga  cagggtctac  ttcttcttca  cggaggtgtc   1080
tgtggagtat  gagtttgtgt  tcagggtgct  gatcccacgg  atagcaagag  tgtgcaaggg   1140
ggaccagggc  ggcctgagga  ccttgcagaa  gaaatggacc  tccttcctga  aagcccgact   1200
catctgctcc  cggccagaca  gcggcttggt  cttcaatgtg  ctgcgggatg  tcttcgtgct   1260
caggtccccg  ggcctgaagg  tgcctgtgtt  ctatgcactc  ttcaccccac  agctgaacaa   1320
cgtggggctg  tcggcagtgt  gcgcctacaa  cctgtccaca  gccgaggagg  tcttctccca   1380
cgggaagtac  atgcagagca  ccacagtgga  gcagtcccac  accaagtggg  tgcgctataa   1440
tggcccggta  cccaagccgc  ggcctggagc  gtgcatcgac  agcgaggcac  gggccgccaa   1500
ctacaccagc  tccttgaatt  tgccagacaa  gacgctgcag  ttcgttaaag  accacccttt   1560
gatggatgac  tcggtaaccc  caatagacaa  caggcccagg  ttaatcaaga  aagatgtgaa   1620
ctacacccag  atcgtggtgg  accggaccca  ggccctggat  gggactgtct  atgatgtcat   1680
gtttgtcagc  acagaccggg  gagctctgca  caaagccatc  agcctcgagc  acgctgttca   1740
catcatcgag  gagacccagc  tcttccagga  cttttgagcca  gtccagaccc  tgctgctgtc   1800
ttcaaagaag  ggcaacaggt  ttgtctatgc  tggctctaac  tcgggcgtgg  tccaggcccc   1860
gctggccttc  tgtgggaagc  acggcacctg  cgaggactgt  gtgctggcgc  gggacccta   1920 ctgcgcctgg  agcccgccca  cagcgacctg  cgtggctctg  caccagaccg  agagccccag   1980
caggggtttg  attcaggaga  tgagcggcga  tgcttctgtg  tgcccggata  aaagtaaagg   2040
aagttaccgg  cagcattttt  tcaagcacgg  tggcacagcg  gaactgaaat  gctcccaaaa   2100
atccaacctg  gcccgggtct  tttggaagtt  ccagaatgac  gtgttgaagg  ccgagagccc   2160
caagtacggt  cttatgggca  gaaaaaactt  gctcatcttc  aacttgtcag  aaggagacag   2220
tggggtgtac  cagtgcctgt  cagaggagag  ggttaagaac  aaaacggtct  tccaagtggt   2280
cgccaagcac  gtcctggaag  tgaaggtggt  tccaaagccc  gtagtggccc  ccaccttgtc   2340
agttgttcag  acagaaggta  gtaggattgc  caccaaagtg  ttggtggcat  ccacccaagg   2400
gtcttctccc  ccaaccccag  ccgtgcaggc  cacctcctcc  ggggccatca  cccttcctcc   2460
caagcctgcg  tccaccggca  catcttgcga  accaaagatc  gtcatcaaca  cggtccccca   2520
gctccactcg  gagaaaacca  tgtatcttaa  gtccagcgac  aaccgcctcc  ccatgtccct   2580
cttcctcttc  ttctttgttc  tcttcctctg  cctctttttc  tacaactgct  ataagggata   2640
cctgcccaga  cagtgcttga  aattccgctc  ggccctacta  attgggaaga  gaagcccaa   2700 gtcagatttc  tgtgaccgtg  agcagagcct  gaaggagacg  ttagtagagc  cagggagctt   2760
ctcccagcag  aatggggagc  accccaagcc  agccctggac  accggctatg  agaccgagca   2820
agacaccatc  accagcaaag  tccccacgga  taggaggac  tcacagagga  tcgacgacct   2880
ttctgccagg  gacaagccct  tgacgtcaa  gtgtgagctg  aagttcgctg  actcagacgc   2940
agatggagac  tgaggccggc  tgtgcatccc  cgctggtgcc  tcggctgcga  cgtgtccagg   3000
cgtggagagt  tttgtgtttc  tcctgttcag  tatccgagtc  tcgtgcagtg  ctgcgtaggt   3060
tagcccgcat  cgtgcagaca  acctcagtcc  tcttgtctat  tttctcttgg  gttgagcctg   3120
tgacttggtt  tctctttgtc  cttttggaaa  aatgacaagc  attgcatccc  agtcttgtgt   3180
tccgaagtca  gtcggagtac  ttgaagaagg  cccacgggcg  gcacggagtt  cctgagccct   3240
ttctgtagtg  ggggaaaggt  ggctggacct  ctgttggctg  agaagagcat  cccttcagct   3300
```

| | | | | |
|---|---|---|---|---|
| tcccctcccc | gtagcagcca | ctaaaagatt | atttaattcc | agattggaaa tgacatttta | 3360 |
| gtttatcaga | ttggtaactt | atcgcctgtt | gtccagattg | gcacgaacct tttcttccac | 3420 |
| ttaattattt | ttttaggatt | ttgctttgat | tgtgtttatg | tcatgggtca tttttttta | 3480 |
| gttacagaag | cagatgtgtt | aatatttaga | agaagatgta | tatcttccag attttgttat | 3540 |
| atatttggca | taaaatacgg | cttacgttgc | ttaagattct | cagggataaa cttccttttg | 3600 |
| ctaaatgcat | tctttctgct | tttagaaatg | tagacataaa | cactcccgg agcccactca | 3660 |
| ccttttttct | ttttcttttt | tttttttaa | ctttattcct | tgagggaagc attgttttg | 3720 |
| gagagatttt | cttctgtac | ttcgttttac | ttttcttttt | ttttaacttt tactctctcg | 3780 |
| aagaagagga | ccttcccaca | tccacgaggt | gggttttgag | caagggaagg tagcctggat | 3840 |
| gagctgagtg | gagccaggct | ggcccagagc | tgagatggga | gtgcggtaca atctggagcc | 3900 |
| cacagctgtc | ggtcagaacc | tcctgtgaga | cagatggaac | cttcacaagg gcgcctttgg | 3960 |
| ttctctgaac | atctccttc | tcttcttgct | tcaattgcat | acccactgcc tgcccagact | 4020 |
| ttctatccag | cctcactgag | ctgcccacta | ctggaaggga | actgggcctc ggtggccggg | 4080 |
| gccgcgagct | gtgaccacag | caccctcaag | catacggcgc | tgttcctgcc actgtcctga | 4140 |
| agatgtgaat | gggtggtacg | atttcaacac | tggttaattt | cacactccat ctccccgctt | 4200 |
| tgtaaatacc | catcgggaag | agactttttt | tccatggtga | agagcaataa actctggatg | 4260 |
| tttgtgaaaa | aaaaaaaaa | aaaa | | | 4284 |

<210> SEQ ID NO 7
<211> LENGTH: 4157
<212> TYPE: DNA
<213> ORGANISM: Homo sapiens

<400> SEQUENCE: 7

| | | | | |
|---|---|---|---|---|
| ctgagccgca | tctgcaatag | cacacttgcc | cggccacctg | ctgccgtgag cctttgctgc | 60 |
| tgaagcccct | ggggtcgcct | ctacctgatg | aggatgtgca | ccccattag ggggctgctc | 120 |
| atggcccttg | cagtgatgtt | tgggacagcg | atggcatttg | cacccatacc ccggatcacc | 180 |
| tgggagcaca | gagaggtgca | cctggtgcag | tttcatgagc | cagacatcta caactactca | 240 |
| gccttgctgc | tgagcgagga | caaggacacc | ttgtacatag | gtgcccggga ggcggtcttc | 300 |
| gctgtgaacg | cactcaacat | ctccgagaag | cagcatgagg | tgtattggaa ggtctcagaa | 360 |
| gacaaaaaag | caaatgtgc | agaaaagggg | aaatcaaaac | agacagagtg cctcaactac | 420 |
| atccgggtgc | tgcagccact | cagcgccact | tcccttacg | tgtgtgggac caacgcattc | 480 |
| cagccggcct | gtgaccacct | gaacttaaca | tcctttaagt | ttctggggaa aaatgaagat | 540 |
| ggcaaaggaa | gatgtccctt | tgacccagca | cacagctaca | catccgtcat ggttgatgga | 600 |
| gaactttatt | cggggacgtc | gtataatttt | ttgggaagtg | aacccatcat ctcccgaaat | 660 |
| tcttcccaca | gtcctctgag | gacagaatat | gcaatccctt | ggctgaacga gcctagtttc | 720 |
| gtgtttgctg | acgtgatccg | aaaaagccca | gacagccccg | acggcgagga tgacagggtc | 780 |
| tacttcttct | tcacggaggt | gtctgtggag | tatgagtttg | tgttcagggt gctgatccca | 840 |
| cggatagcaa | gagtgtgcaa | gggggaccag | ggcggcctga | ggaccttgca gaagaaatgg | 900 |
| acctccttcc | tgaaagcccg | actcatctgc | tcccggccag | acagcggctt ggtcttcaat | 960 |
| gtgctgcggg | atgtcttcgt | gctcaggtcc | ccgggcctga | aggtgcctgt gttctatgca | 1020 |
| ctcttcaccc | cacagctgaa | caacgtgggg | ctgtcggcag | tgtgcgccta caacctgtcc | 1080 |
| acagccgagg | aggtcttctc | ccacgggaag | tacatgcaga | gcaccacagt ggagcagtcc | 1140 |

```
cacaccaagt gggtgcgcta taatggcccg gtacccaagc cgcggcctgg agcgtgcatc    1200
gacagcgagg cacgggccgc caactacacc agctccttga atttgccaga caagacgctg    1260
cagttcgtta aagaccaccc tttgatggat gactcggtaa ccccaataga caacaggccc    1320
aggttaatca agaaagatgt gaactacacc cagatcgtgg tggaccggac ccaggccctg    1380
gatgggactg tctatgatgt catgtttgtc agcacagacc ggggagctct gcacaaagcc    1440
atcagcctcg agcacgctgt tcacatcatc gaggagaccc agctcttcca ggactttgag    1500
ccagtccaga ccctgctgct gtcttcaaag aagggcaaca ggtttgtcta tgctggctct    1560
aactcgggcg tggtccaggc cccgctggcc ttctgtggga agcacggcac ctgcgaggac    1620
tgtgtgctgg cgcgggaccc ctactgcgcc tggagcccgc ccacagcgac ctgcgtggct    1680
ctgcaccaga ccgagagccc cagcaggggt tgattcagg agatgagcgg cgatgcttct     1740
gtgtgcccgg ataaaagtaa aggaagttac cggcagcatt ttttcaagca cggtggcaca    1800
gcggaactga aatgctccca aaaatccaac ctggcccggg tcttttggaa gttccagaat    1860
ggcgtgttga aggccgagag ccccaagtac ggtcttatgg gcagaaaaaa cttgctcatc    1920
ttcaacttgt cagaaggaga cagtgggtg taccagtgcc tgtcagagga gagggttaag    1980
aacaaaacgg tcttccaagt ggtcgccaag cacgtcctgg aagtgaaggt ggttccaaag    2040
cccgtagtgg cccccacctt gtcagttgtt cagacagaag gtagtaggat tgccaccaaa    2100
gtgttggtgg catccaccca agggtcttct ccccaaccc cagccgtgca ggccacctcc     2160
tccggggcca tcacccttcc tcccaagcct gcgccaccg gcacatcctg cgaaccaaag     2220
atcgtcatca acacggtccc ccagctccac tcggagaaaa ccatgtatct taagtccagc    2280
gacaaccgcc tcctcatgtc cctcttcctc ttcttctttg ttctcttcct ctgcctcttt    2340
ttctacaact gctataaggg ataccttgccc agacagtgct tgaaattccg ctcggcccta   2400
ctaattggga agaagaagcc caagtcagat ttctgtgacc gtgagcagag cctgaaggag    2460
acgttagtag agccagggag cttctcccag cagaatgggg agcaccccaa gccagccctg    2520
gacaccggct atgagaccga gcaagacacc atcaccagca agtccccac ggatagggag     2580 gactcacaga ggatcgacga cctttctgcc agggacaagc cctttgacgt caagtgtgag    2640
ctgaagttcg ctgactcaga cgcagatgga gactgaggcc ggctgtgcat ccccgctggt    2700
gcctcggctg cgacgtgtcc aggcgtggag agttttgtgt ttctcctgtt cagtatccga    2760
gtctcgtgca gtgctgcgta ggttagcccg catcgtgcag acaacctcag tcctcttgtc    2820
tattttctct tgggttgagc ctgtgacttg gtttctcttt gtccttttgg aaaaatgaca    2880
agcattgcat cccagtcttg tgttccgaag tcagtcggag tacttgaaga aggcccacgg    2940
gcggcacgga gttcctgagc cctttctgta gtgggggaaa ggtggctgga cctctgttgg    3000
ctgagaagag catcccttca gcttcccctc cccgtagcag ccactaaaag attatttaat    3060
tccagattgg aaatgacatt ttagtttatc agattggtaa cttatcgcct gttgtccaga    3120
ttggcacgaa ccttttcttc cacttaatta tttttttagg attttgcttt gattgtgttt    3180
atgtcatggg tcattttttt ttagttacag aagcagttgt gttaatattt agaagaagat    3240
gtatatcttc cagattttgt tatatatttg gcataaaata cggcttacgt tgcttaagat    3300
tctcagggat aaacttcctt ttgctaaatg cattcttttct gcttttagaa atgtagacat    3360
aaacactccc cggagcccac tcacctttt tctttttctt ttttttttt taactttatt      3420 ccttgaggga agcattgttt ttggagagat tttcttctg tacttcgttt tacttttctt     3480 ttttttaac ttttactctc tcgaagaaga ggaccttccc acatccacga ggtgggtttt     3540
```

-continued

```
gagcaaggga aggtagcctg gatgagctga gtggagccag gctggcccag agctgagatg      3600
ggagtgcggt acaatctgga gcccacagct gtcggtcaga acctcctgtg agacagatgg      3660
aaccttcaca agggcgcctt tggttctctg aacatctcct ttctcttctt gcttcaattg      3720
cttacccact gcctgcccag actttctatc cagcctcact gagctgccca ctactggaag      3780
ggaactgggc ctcggtggcc ggggccgcga gctgtgacca cagcaccctc aagcatacgg      3840
cgctgttcct gccactgtcc tgaagatgtg aatgggtggt acgatttcaa cactggttaa      3900
tttcacactc catctccccg ctttgtaaat acccatcggg aagagacttt ttttccatgg      3960
tgaagagcaa taaactctgg atgtttgtgc gcgtgtgtgg acagtcttat cttccagcat      4020
gataggattt gaccattttg gtgtaaacat ttgtgtttta taagatttac cttgttttta      4080
tttttctact ttgaattgta tacatttgga aagtacccaa ataaatgaga agcttctatc      4140
cttaaaaaaa aaaaaaa                                                     4157
```

<210> SEQ ID NO 8
<211> LENGTH: 856
<212> TYPE: PRT
<213> ORGANISM: Homo sapiens

<400> SEQUENCE: 8

```
Met Arg Met Cys Thr Pro Ile Arg Gly Leu Leu Met Ala Val Met Phe
 1               5                  10                  15

Gly Thr Ala Met Ala Phe Ala Pro Ile Pro Arg Ile Thr Trp Glu His
             20                  25                  30

Arg Glu Val His Leu Val Gln Phe His Glu Pro Asp Ile Tyr Asn Tyr
         35                  40                  45

Ser Ala Leu Leu Leu Ser Glu Asp Lys Asp Thr Leu Tyr Ile Gly Ala
     50                  55                  60

Arg Glu Ala Val Phe Ala Val Asn Ala Leu Asn Ile Ser Glu Lys Gln
 65                  70                  75                  80

His Glu Val Tyr Trp Lys Val Ser Glu Asp Lys Lys Ala Lys Cys Ala
                 85                  90                  95

Glu Lys Gly Lys Ser Lys Gln Thr Glu Cys Leu Asn Tyr Ile Arg Val
            100                 105                 110

Leu Gln Pro Leu Ser Ala Thr Ser Leu Tyr Val Cys Gly Thr Asn Ala
        115                 120                 125

Phe Gln Pro Ala Cys Asp His Leu Asn Leu Thr Ser Phe Lys Phe Leu
    130                 135                 140

Gly Lys Asn Glu Asp Gly Lys Gly Arg Cys Pro Phe Asp Pro Ala His
145                 150                 155                 160

Ser Tyr Thr Ser Val Met Val Asp Gly Glu Lys Gly Thr Ser Tyr Asn
                165                 170                 175

Phe Leu Gly Ser Glu Pro Ile Ile Ser Arg Asn Ser Ser His Ser Pro
            180                 185                 190

Leu Arg Thr Glu Tyr Ala Ile Pro Trp Leu Asn Glu Pro Ser Phe Val
        195                 200                 205

Phe Ala Asp Val Ile Arg Lys Ser Pro Asp Ser Pro Asp Gly Glu Asp
    210                 215                 220

Asp Arg Val Tyr Phe Phe Phe Thr Glu Val Ser Val Glu Tyr Glu Phe
225                 230                 235                 240

Val Phe Arg Val Leu Ile Pro Arg Ile Ala Arg Val Cys Lys Gly Asp
                245                 250                 255

Gln Gly Gly Leu Arg Thr Leu Gln Lys Lys Trp Thr Ser Phe Leu Lys
            260                 265                 270
```

```
Ala Arg Leu Ile Cys Ser Arg Pro Asp Ser Gly Leu Val Phe Asn Val
        275                 280                 285

Leu Arg Asp Val Phe Val Leu Arg Ser Pro Gly Leu Lys Val Pro Val
290                 295                 300

Phe Tyr Ala Leu Phe Thr Pro Gln Leu Asn Asn Val Gly Leu Ser Ala
305                 310                 315                 320

Val Cys Ala Tyr Asn Leu Ser Thr Ala Glu Glu Val Phe Ser His Gly
                325                 330                 335

Lys Tyr Met Gln Ser Thr Thr Val Glu Gln Ser His Thr Lys Trp Val
                340                 345                 350

Arg Tyr Asn Gly Pro Val Pro Lys Pro Arg Pro Gly Ala Cys Ile Asp
        355                 360                 365

Ser Glu Ala Arg Ala Ala Asn Tyr Thr Ser Ser Leu Asn Leu Pro Asp
370                 375                 380

Lys Thr Leu Gln Phe Val Lys Asp His Pro Leu Met Asp Asp Ser Val
385                 390                 395                 400

Thr Pro Ile Asp Asn Arg Pro Arg Leu Ile Lys Lys Asp Val Asn Tyr
                405                 410                 415

Thr Gln Ile Val Val Asp Arg Thr Gln Ala Leu Asp Gly Thr Val Tyr
                420                 425                 430

Asp Val Met Phe Val Ser Thr Asp Arg Gly Ala Leu His Lys Ala Ile
        435                 440                 445

Ser Leu Glu His Ala Val His Ile Ile Glu Glu Thr Gln Leu Phe Gln
450                 455                 460

Asp Phe Glu Pro Val Gln Thr Leu Leu Leu Ser Ser Lys Lys Gly Asn
465                 470                 475                 480

Arg Phe Val Tyr Ala Gly Ser Asn Ser Gly Val Val Gln Ala Pro Leu
                485                 490                 495

Ala Phe Cys Gly Lys His Gly Thr Cys Glu Asp Cys Val Leu Ala Arg
        500                 505                 510

Asp Pro Tyr Cys Ala Trp Ser Pro Pro Thr Ala Thr Cys Val His Gln
515                 520                 525

Thr Glu Ser Pro Ser Arg Gly Leu Ile Gln Glu Met Ser Gly Asp Ala
530                 535                 540

Ser Val Cys Pro Asp Lys Ser Lys Gly Ser Tyr Arg Gln His Phe Phe
545                 550                 555                 560

Lys His Gly Gly Thr Ala Glu Leu Lys Cys Ser Gln Lys Ser Asn Leu
                565                 570                 575

Ala Arg Val Phe Trp Lys Phe Gln Asn Gly Val Leu Lys Ala Glu Ser
        580                 585                 590

Pro Lys Tyr Gly Leu Met Gly Arg Lys Asn Leu Leu Ile Phe Asn Leu
595                 600                 605

Ser Glu Gly Asp Ser Gly Val Tyr Gln Cys Leu Ser Glu Glu Arg Val
610                 615                 620

Lys Asn Lys Thr Val Phe Gln Val Val Ala Lys His Val Leu Glu Val
625                 630                 635                 640

Lys Val Val Pro Lys Pro Val Val Ala Pro Thr Leu Ser Val Val Gln
                645                 650                 655

Thr Glu Gly Ser Arg Ile Ala Thr Lys Val Leu Val Ala Ser Thr Gln
        660                 665                 670

Gly Ser Ser Pro Pro Thr Pro Ala Val Gln Ala Thr Ser Ser Gly Ala
        675                 680                 685

Ile Thr Leu Pro Pro Lys Pro Ala Pro Thr Gly Thr Ser Cys Glu Pro
```

```
                690                 695                 700
Lys Ile Val Ile Asn Thr Val Pro Gln Leu His Ser Glu Lys Thr Met
705                 710                 715                 720

Tyr Leu Lys Ser Ser Asp Asn Arg Leu Leu Met Ser Leu Phe Leu Phe
                725                 730                 735

Phe Phe Val Leu Phe Leu Cys Leu Phe Phe Tyr Asn Cys Tyr Lys Gly
            740                 745                 750

Tyr Leu Pro Arg Gln Cys Leu Lys Phe Arg Ser Ala Leu Leu Ile Gly
            755                 760                 765

Lys Lys Lys Pro Lys Ser Asp Phe Cys Asp Arg Glu Gln Ser Leu Lys
770                 775                 780

Glu Thr Leu Val Glu Pro Gly Ser Phe Ser Gln Gln Asn Gly Glu His
785                 790                 795                 800

Pro Lys Pro Ala Leu Asp Thr Gly Tyr Glu Thr Gln Asp Thr Ile
                805                 810                 815

Thr Ser Lys Val Pro Thr Asp Arg Glu Asp Ser Gln Arg Ile Asp Asp
                820                 825                 830

Leu Ser Ala Arg Asp Lys Pro Phe Asp Val Lys Cys Glu Leu Lys Phe
            835                 840                 845

Ala Asp Ser Asp Ala Asp Gly Asp
            850                 855

<210> SEQ ID NO 9
<211> LENGTH: 856
<212> TYPE: PRT
<213> ORGANISM: Homo sapiens

<400> SEQUENCE: 9

Met Arg Met Cys Thr Pro Ile Arg Gly Leu Leu Met Ala Val Met Phe
1               5                   10                  15

Gly Thr Ala Met Ala Phe Ala Pro Ile Pro Arg Ile Thr Trp Glu His
                20                  25                  30

Arg Glu Val His Leu Val Gln Phe His Glu Pro Asp Ile Tyr Asn Tyr
            35                  40                  45

Ser Ala Leu Leu Leu Ser Glu Asp Lys Asp Thr Leu Tyr Ile Gly Ala
    50                  55                  60

Arg Glu Ala Val Phe Ala Val Asn Ala Leu Asn Ile Ser Glu Lys Gln
65                  70                  75                  80

His Glu Val Tyr Trp Lys Val Ser Glu Asp Lys Lys Ala Lys Cys Ala
                85                  90                  95

Glu Lys Gly Lys Ser Lys Gln Thr Glu Cys Leu Asn Tyr Ile Arg Val
            100                 105                 110

Leu Gln Pro Leu Ser Ala Thr Ser Leu Tyr Val Cys Gly Thr Asn Ala
        115                 120                 125

Phe Gln Pro Ala Cys Asp His Leu Asn Leu Thr Ser Phe Lys Phe Leu
    130                 135                 140

Gly Lys Asn Glu Asp Gly Lys Gly Arg Cys Pro Phe Asp Pro Ala His
145                 150                 155                 160

Ser Tyr Thr Ser Val Met Val Asp Gly Glu Lys Gly Thr Ser Tyr Asn
                165                 170                 175

Phe Leu Gly Ser Glu Pro Ile Ile Ser Arg Asn Ser Ser His Ser Pro
            180                 185                 190

Leu Arg Thr Glu Tyr Ala Ile Pro Trp Leu Asn Glu Pro Ser Phe Val
        195                 200                 205

Phe Ala Asp Val Ile Arg Lys Ser Pro Asp Ser Pro Asp Gly Glu Asp
```

```
            210                 215                 220
Asp Arg Val Tyr Phe Phe Thr Glu Val Ser Val Glu Tyr Glu Phe
225                 230                 235                 240

Val Phe Arg Val Leu Ile Pro Arg Ile Ala Arg Val Cys Lys Gly Asp
                    245                 250                 255

Gln Gly Gly Leu Arg Thr Leu Gln Lys Lys Trp Thr Ser Phe Leu Lys
                    260                 265                 270

Ala Arg Leu Ile Cys Ser Arg Pro Asp Ser Gly Leu Val Phe Asn Val
                275                 280                 285

Leu Arg Asp Val Phe Val Leu Arg Ser Pro Gly Leu Lys Val Pro Val
    290                 295                 300

Phe Tyr Ala Leu Phe Thr Pro Gln Leu Asn Asn Val Gly Leu Ser Ala
305                 310                 315                 320

Val Cys Ala Tyr Asn Leu Ser Thr Ala Glu Glu Val Phe Ser His Gly
                    325                 330                 335

Lys Tyr Met Gln Ser Thr Thr Val Glu Gln Ser His Thr Lys Trp Val
                340                 345                 350

Arg Tyr Asn Gly Pro Val Pro Lys Pro Arg Pro Gly Ala Cys Ile Asp
                355                 360                 365

Ser Glu Ala Arg Ala Ala Asn Tyr Thr Ser Ser Leu Asn Leu Pro Asp
    370                 375                 380

Lys Thr Leu Gln Phe Val Lys Asp His Pro Leu Met Asp Asp Ser Val
385                 390                 395                 400

Thr Pro Ile Asp Asn Arg Pro Arg Leu Ile Lys Lys Asp Val Asn Tyr
                    405                 410                 415

Thr Gln Ile Val Val Asp Arg Thr Gln Ala Leu Asp Gly Thr Val Tyr
                420                 425                 430

Asp Val Met Phe Val Ser Thr Asp Arg Gly Ala Leu His Lys Ala Ile
                435                 440                 445

Ser Leu Glu His Ala Val His Ile Ile Glu Glu Thr Gln Leu Phe Gln
    450                 455                 460

Asp Phe Glu Pro Val Gln Thr Leu Leu Leu Ser Ser Lys Lys Gly Asn
465                 470                 475                 480

Arg Phe Val Tyr Ala Gly Ser Asn Ser Gly Val Val Gln Ala Pro Leu
                    485                 490                 495

Ala Phe Cys Gly Lys His Gly Thr Cys Glu Asp Cys Val Leu Ala Arg
                500                 505                 510

Asp Pro Tyr Cys Ala Trp Ser Pro Pro Thr Ala Thr Cys Val His Gln
                515                 520                 525

Thr Glu Ser Pro Ser Arg Gly Leu Ile Gln Glu Met Ser Gly Asp Ala
    530                 535                 540

Ser Val Cys Pro Asp Lys Ser Lys Gly Ser Tyr Arg Gln His Phe Phe
545                 550                 555                 560

Lys His Gly Gly Thr Ala Glu Leu Lys Cys Ser Gln Lys Ser Asn Leu
                    565                 570                 575

Ala Arg Val Phe Trp Lys Phe Gln Asn Gly Val Leu Lys Ala Glu Ser
                580                 585                 590

Pro Lys Tyr Gly Leu Met Gly Arg Lys Asn Leu Leu Ile Phe Asn Leu
                595                 600                 605

Ser Glu Gly Asp Ser Gly Val Tyr Gln Cys Leu Ser Glu Glu Arg Val
    610                 615                 620

Lys Asn Lys Thr Val Phe Gln Val Val Ala Lys His Val Leu Glu Val
625                 630                 635                 640
```

```
Lys Val Val Pro Lys Pro Val Ala Pro Thr Leu Ser Val Val Gln
            645                 650                 655

Thr Glu Gly Ser Arg Ile Ala Thr Lys Val Leu Val Ala Ser Thr Gln
            660                 665                 670

Gly Ser Ser Pro Pro Thr Pro Ala Val Gln Ala Thr Ser Ser Gly Ala
            675                 680                 685

Ile Thr Leu Pro Pro Lys Pro Ala Pro Thr Gly Thr Ser Cys Glu Pro
            690                 695                 700

Lys Ile Val Ile Asn Thr Val Pro Gln Leu His Ser Glu Lys Thr Met
705                 710                 715                 720

Tyr Leu Lys Ser Ser Asp Asn Arg Leu Leu Met Ser Leu Phe Leu Phe
                725                 730                 735

Phe Phe Val Leu Phe Leu Cys Leu Phe Phe Tyr Asn Cys Tyr Lys Gly
            740                 745                 750

Tyr Leu Pro Arg Gln Cys Leu Lys Phe Arg Ser Ala Leu Leu Ile Gly
            755                 760                 765

Lys Lys Lys Pro Lys Ser Asp Phe Cys Asp Arg Glu Gln Ser Leu Lys
            770                 775                 780

Glu Thr Leu Val Glu Pro Gly Ser Phe Ser Gln Gln Asn Gly Glu His
785                 790                 795                 800

Pro Lys Pro Ala Leu Asp Thr Gly Tyr Glu Thr Glu Gln Asp Thr Ile
                805                 810                 815

Thr Ser Lys Val Pro Thr Asp Arg Glu Asp Ser Gln Arg Ile Asp Asp
            820                 825                 830

Leu Ser Ala Arg Asp Lys Pro Phe Asp Val Lys Cys Glu Leu Lys Phe
            835                 840                 845

Ala Asp Ser Asp Ala Asp Gly Asp
            850                 855

<210> SEQ ID NO 10
<211> LENGTH: 856
<212> TYPE: PRT
<213> ORGANISM: Homo sapiens

<400> SEQUENCE: 10

Met Arg Met Cys Thr Pro Ile Arg Gly Leu Leu Met Ala Val Met Phe
1               5                   10                  15

Gly Thr Ala Met Ala Phe Ala Pro Ile Pro Arg Ile Thr Trp Glu His
            20                  25                  30

Arg Glu Val His Leu Val Gln Phe His Glu Pro Asp Ile Tyr Asn Tyr
            35                  40                  45

Ser Ala Leu Leu Leu Ser Glu Asp Lys Asp Thr Leu Tyr Ile Gly Ala
            50                  55                  60

Arg Glu Ala Val Phe Ala Val Asn Ala Leu Asn Ile Ser Glu Lys Gln
65                  70                  75                  80

His Glu Val Tyr Trp Lys Val Ser Glu Asp Lys Lys Ala Lys Cys Ala
                85                  90                  95

Glu Lys Gly Lys Ser Lys Gln Thr Glu Cys Leu Asn Tyr Ile Arg Val
            100                 105                 110

Leu Gln Pro Leu Ser Ala Thr Ser Leu Tyr Val Cys Gly Thr Asn Ala
            115                 120                 125

Phe Gln Pro Ala Cys Asp His Leu Asn Leu Thr Ser Phe Lys Phe Leu
            130                 135                 140

Gly Lys Asn Glu Asp Gly Lys Gly Arg Cys Pro Phe Asp Pro Ala His
145                 150                 155                 160
```

```
Ser Tyr Thr Ser Val Met Val Asp Gly Glu Lys Gly Thr Ser Tyr Asn
                165             170                 175

Phe Leu Gly Ser Glu Pro Ile Ile Ser Arg Asn Ser Ser His Ser Pro
            180                 185                 190

Leu Arg Thr Glu Tyr Ala Ile Pro Trp Leu Asn Glu Pro Ser Phe Val
            195                 200                 205

Phe Ala Asp Val Ile Arg Lys Ser Pro Asp Ser Pro Asp Gly Glu Asp
        210                 215                 220

Asp Arg Val Tyr Phe Phe Thr Glu Val Ser Val Glu Tyr Glu Phe
225                 230                 235                 240

Val Phe Arg Val Leu Ile Pro Arg Ile Ala Arg Val Cys Lys Gly Asp
                245                 250                 255

Gln Gly Gly Leu Arg Thr Leu Gln Lys Lys Trp Thr Ser Phe Leu Lys
            260                 265                 270

Ala Arg Leu Ile Cys Ser Arg Pro Asp Ser Gly Leu Val Phe Asn Val
            275                 280                 285

Leu Arg Asp Val Phe Val Leu Arg Ser Pro Gly Leu Lys Val Pro Val
    290                 295                 300

Phe Tyr Ala Leu Phe Thr Pro Gln Leu Asn Asn Val Gly Leu Ser Ala
305                 310                 315                 320

Val Cys Ala Tyr Asn Leu Ser Thr Ala Glu Glu Val Phe Ser His Gly
                325                 330                 335

Lys Tyr Met Gln Ser Thr Thr Val Glu Gln Ser His Thr Lys Trp Val
            340                 345                 350

Arg Tyr Asn Gly Pro Val Pro Lys Pro Arg Pro Gly Ala Cys Ile Asp
        355                 360                 365

Ser Glu Ala Arg Ala Ala Asn Tyr Thr Ser Ser Leu Asn Leu Pro Asp
370                 375                 380

Lys Thr Leu Gln Phe Val Lys Asp His Pro Leu Met Asp Asp Ser Val
385                 390                 395                 400

Thr Pro Ile Asp Asn Arg Pro Arg Leu Ile Lys Lys Asp Val Asn Tyr
                405                 410                 415

Thr Gln Ile Val Val Asp Arg Thr Gln Ala Leu Asp Gly Thr Val Tyr
            420                 425                 430

Asp Val Met Phe Val Ser Thr Asp Arg Gly Ala Leu His Lys Ala Ile
        435                 440                 445

Ser Leu Glu His Ala Val His Ile Ile Glu Glu Thr Gln Leu Phe Gln
450                 455                 460

Asp Phe Glu Pro Val Gln Thr Leu Leu Leu Ser Lys Lys Gly Asn
465                 470                 475                 480

Arg Phe Val Tyr Ala Gly Ser Asn Ser Gly Val Val Gln Ala Pro Leu
                485                 490                 495

Ala Phe Cys Gly Lys His Gly Thr Cys Glu Asp Cys Val Leu Ala Arg
            500                 505                 510

Asp Pro Tyr Cys Ala Trp Ser Pro Pro Thr Ala Thr Cys Val His Gln
        515                 520                 525

Thr Glu Ser Pro Ser Arg Gly Leu Ile Gln Glu Met Ser Gly Asp Ala
530                 535                 540

Ser Val Cys Pro Asp Lys Ser Lys Gly Ser Tyr Arg Gln His Phe Phe
545                 550                 555                 560

Lys His Gly Gly Thr Ala Glu Leu Lys Cys Ser Gln Lys Ser Asn Leu
                565                 570                 575

Ala Arg Val Phe Trp Lys Phe Gln Asn Gly Val Leu Lys Ala Glu Ser
            580                 585                 590
```

```
Pro Lys Tyr Gly Leu Met Gly Arg Lys Asn Leu Leu Ile Phe Asn Leu
        595                 600                 605

Ser Glu Gly Asp Ser Gly Val Tyr Gln Cys Leu Ser Glu Glu Arg Val
        610                 615                 620

Lys Asn Lys Thr Val Phe Gln Val Val Ala Lys His Val Leu Glu Val
625                 630                 635                 640

Lys Val Val Pro Lys Pro Val Ala Pro Thr Leu Ser Val Val Gln
                645                 650                 655

Thr Glu Gly Ser Arg Ile Ala Thr Lys Val Leu Val Ala Ser Thr Gln
            660                 665                 670

Gly Ser Ser Pro Pro Thr Pro Ala Val Gln Ala Thr Ser Ser Gly Ala
        675                 680                 685

Ile Thr Leu Pro Pro Lys Pro Ala Pro Thr Gly Thr Ser Cys Glu Pro
        690                 695                 700

Lys Ile Val Ile Asn Thr Val Pro Gln Leu His Ser Glu Lys Thr Met
705                 710                 715                 720

Tyr Leu Lys Ser Ser Asp Asn Arg Leu Leu Met Ser Leu Phe Leu Phe
            725                 730                 735

Phe Phe Val Leu Phe Leu Cys Leu Phe Tyr Asn Cys Tyr Lys Gly
        740                 745                 750

Tyr Leu Pro Arg Gln Cys Leu Lys Phe Arg Ser Ala Leu Leu Ile Gly
        755                 760                 765

Lys Lys Lys Pro Lys Ser Asp Phe Cys Asp Arg Glu Gln Ser Leu Lys
    770                 775                 780

Glu Thr Leu Val Glu Pro Gly Ser Phe Ser Gln Gln Asn Gly Glu His
785                 790                 795                 800

Pro Lys Pro Ala Leu Asp Thr Gly Tyr Glu Thr Glu Gln Asp Thr Ile
                805                 810                 815

Thr Ser Lys Val Pro Thr Asp Arg Glu Asp Ser Gln Arg Ile Asp Asp
            820                 825                 830

Leu Ser Ala Arg Asp Lys Pro Phe Asp Val Lys Cys Glu Leu Lys Phe
        835                 840                 845

Ala Asp Ser Asp Ala Asp Gly Asp
        850                 855

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
ggtgcctgtg ttctatgcac tct                                           23

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
gacaggttgt aggcgcacac t                                             21

<210> SEQ ID NO 13
<211> LENGTH: 23
<212> TYPE: DNA
```

```
<213> ORGANISM: Artificial Sequence
<220> FEATURE:
<223> OTHER INFORMATION: Probe sequence

<400> SEQUENCE: 13
accccacagc tgaacaacgt ggg                                            23
```

The invention claimed is:

1. A method for diagnosing cancer comprising detecting evidence of increased gene expression in a patient breast, ovary, or pancreatic sample of SEMA4D wherein evidence of increased gene expression of SEMA4D in said patient sample compared to a normal control of the same tissue type as the patient sample is diagnostic of cancer, wherein the cancer is selected from the group consisting of breast cancer, ovary cancer and pancreatic cancer.

2. The method of claim 1 wherein the increased gene expression is a mRNA.

3. A method of diagnosing cancer selected from the group consisting of breast cancer, colon cancer, ovarian cancer, pancreatic cancer and prostate cancer, the method comprising:
   (a) measuring a level of mRNA of SEMA4D in a first sample, said first sample comprising a first tissue type selected from the group consisting of breast, colon, ovary, pancreatic and prostate tissue of a first individual; and
   (b) comparing the level of mRNA in (a) to:
      (1) a level of the mRNA in a second sample, said second sample comprising a normal tissue type selected from the group consisting of breast, colon, ovary, pancreatic and prostate tissue of said first individual, or
      (2) a level of the mRNA in a third sample, said third sample comprising a normal tissue type selected from the group consisting of breast, colon, ovary, pancreatic and prostate tissue from an unaffected individual;
   wherein at least a two fold increase between the level of mRNA in (a) and the level of the mRNA in the second sample or the third sample indicates that the first individual has breast, colon, ovary, pancreatic or prostate cancer.

4. The method of claim 3 wherein at least a three fold increase between the level of mRNA in (a) and the level of the mRNA in the second sample or the third sample indicates that the first individual has cancer.

* * * * *